US008268793B2

(12) United States Patent
Hedtjarn

(10) Patent No.: US 8,268,793 B2
(45) Date of Patent: Sep. 18, 2012

(54) RNA ANTAGONIST COMPOUNDS FOR THE MODULATION OF HER3

(75) Inventor: Maj Hedtjarn, Copenhagen (DK)

(73) Assignees: Santaris Pharma A/S, Hersholm (DK); Enzon Pharmaceuticals, Inc., Piscataway, NJ (US)

( * ) Notice: Subject to any disclaimer, the term of this patent is extended or adjusted under 35 U.S.C. 154(b) by 433 days.

(21) Appl. No.: 12/118,271

(22) Filed: May 9, 2008

(65) Prior Publication Data

US 2008/0318894 A1 Dec. 25, 2008

Related U.S. Application Data

(60) Provisional application No. 60/917,392, filed on May 11, 2007, provisional application No. 61/023,250, filed on Jan. 24, 2008.

(51) Int. Cl.
*A01N 43/04* (2006.01)
*C12Q 1/68* (2006.01)
*C12P 19/34* (2006.01)
*C07H 21/02* (2006.01)
*C07H 21/04* (2006.01)

(52) U.S. Cl. .......... 514/44; 435/6; 435/91.1; 435/91.31; 435/458; 536/23.1; 536/24.31; 536/24.5

(58) Field of Classification Search .............. 435/6, 91.1, 435/91.31, 455, 458; 514/44; 536/23.1, 536/24.5, 24.31
See application file for complete search history.

(56) References Cited

U.S. PATENT DOCUMENTS

| | | | |
|---|---|---|---|
| 4,914,210 A | 4/1990 | Levenson et al. | |
| 4,962,029 A | 10/1990 | Levenson et al. | |
| 6,133,246 A * | 10/2000 | McKay et al. ............... | 514/44 A |
| 6,277,640 B1 | 8/2001 | Bennett et al. | |
| 7,087,229 B2 | 8/2006 | Zhao et al. | |
| 2003/0143732 A1* | 7/2003 | Fosnaugh et al. ............ | 435/325 |
| 2003/0206887 A1* | 11/2003 | Morrissey et al. .......... | 424/93.2 |
| 2004/0180351 A1* | 9/2004 | Giese et al. ....................... | 435/6 |
| 2004/0235773 A1 | 11/2004 | Zhao et al. | |
| 2005/0176024 A1 | 8/2005 | McSwiggen et al. | |
| 2005/0266409 A1 | 12/2005 | Brown et al. | |
| 2008/0318894 A1 | 12/2008 | Hedtjarn | |

FOREIGN PATENT DOCUMENTS

| | | | |
|---|---|---|---|
| WO | 99/34016 | | 7/1999 |
| WO | WO 02/10409 | | 2/2002 |
| WO | WO 2004/083430 | * | 3/2004 |
| WO | WO 2004/046160 | | 6/2004 |
| WO | WO 2004/070062 | * | 8/2004 |
| WO | 2005/049829 | | 6/2005 |
| WO | 2005/094357 | | 10/2005 |
| WO | WO 2007/031091 | | 3/2007 |
| WO | WO 2007/146511 | | 12/2007 |
| WO | WO 2008/034123 | | 3/2008 |
| WO | WO 2008/053314 | | 5/2008 |
| WO | 2008/112898 | | 9/2008 |
| WO | 2008109361 | | 9/2008 |
| WO | WO 2008/138904 | | 11/2008 |

OTHER PUBLICATIONS

U.S. Appl. No. 60/977,409, Hansen et al.
U.S. Appl. No. 60/917,392, filed May 11, 2007, Hedtjarn, M.
U.S. Appl. No. 61/023,250, filed Jan. 24, 2008, Hedtjarn, M.
Akinc, et al., "A combinatorial library of lipid-like materials for delivery of RNAi therapeutics," *Nature Biotechnology*, vol. 26, No. 5, pp. 561-569 (2008).
Bae, et al., "Patterning of proneuronal and inter-proneuronal domains by hairy- and enhancer of split-related genes in zebrafish neuroectoderm," *Development* 132, 1609, pp. 1375-1385 (2006).
Freier, et al., "The ups and downs of nucleic acid stability: structure-stability studies on chemically-modified DNA:RNA duplexes," *Nucleic Acids Research*, vol. 25, No. 22, pp. 4429-4443 (1997).
International Search Report for family member PCT/EP2008/055779 dated Apr. 9, 2009.
Sergina, et al., "Escape from HER-family tyrosine kinase inhibitor therapy by the kinase-inactive HER3," *Nature*, vol. 445, pp. 437-441 (2007).
Sithanandam, et al., "Cell cycle activation in lung adenocarcinoma cells by the ErbB3/phosphatidylinositol 3-kinase/Akt pathway," *Carcinogenesis*, vol. 24, No. 10, pp. 1581-1592 (2003).
Uhlmann, Eugen, "Recent advances in the medicinal chemistry of antisense oligonucleotides," *Current Opinion in Drug Discovery & Development*, vol. 3, No. 2, pp. 203-213 (2000).
Yarden, et al., "Untangling the ErbB Signalling Network," *Nat. Rev. Mol. Cell. Biol.*, vol. 2, No. 2, pp. 127-137 (2001).
Zhao, et al., "A New Platform for Oligonucleotide Delivery Utilizing the PEG Prodrug Aproach," *Bioconjugate Chem.*, vol. 16, pp. 758-766 (2005).
Zhao, et al., "Delivery of G3139 using releasable PEG-linkers: Impact on pharmacokinetic profile and anti-tumor efficacy," *journal of controlled release*, vol. 119, pp. 143-152 (2007).
Fukumoto et al., Effect of transcriptional downregulation of EGFR on downstream signaling in human cancer cells. Proc. Amer. Assoc. Cancer Res. 2004, vol. 45; Abstract 4651.
Buck et al., Inactivation of Akt by the epidermal growth factor receptor inhibitor erlotinib is mediated by HER-3 in pancreatic and colorectal tumor cell lines and contributes to erlotinib sensitivity. Mol. Cancer Ther. Aug. 2006, 5 (8):2051-2059.
International Search Report issued in PCT/US09/63357 dated Mar. 16, 2010.
European Search Report issued in EP 08 759 503 .9 dated May 11, 2010.
Xu et al., Effective small interfering RNAs and phosphorothioate antisense DNAs have different preferences for target sites in the luciferase mRNAs. Biochemical and Biophysical Research Communications, May 2003, 306, pp. 712-717.

* cited by examiner

*Primary Examiner* — Jane Zara
(74) *Attorney, Agent, or Firm* — Stoel Rives LLP

(57) ABSTRACT

The invention relates to oligomer compounds (oligomers), which target HER3 mRNA in a cell, leading to reduced expression of HER3 and/or HER2 and/or EGFR. Reduction of HER3 and/or HER2 and/or EGFR expression is beneficial for a range of medical disorders, such hyperproliferative disorders (e.g., cancer). The invention provides therapeutic compositions comprising oligomers and methods for modulating the expression of HER3 and/or HER2 and/or EGFR using said oligomers, including methods of treatment.

11 Claims, 11 Drawing Sheets

SEQUENCE LISTING

<160> NUMBER OF SEQ ID NOS: 248

<210> SEQ ID NO 1
<211> LENGTH: 16
<212> TYPE: DNA
<213> ORGANISM: Artificial
<220> FEATURE:
<223> OTHER INFORMATION: Antisense oligonucleotides

<400> SEQUENCE: 1

```
gctccagaca tcactc                                                    16

<210> SEQ ID NO 2
<211> LENGTH: 15
<212> TYPE: DNA
<213> ORGANISM: Artificial
<220> FEATURE:
<223> OTHER INFORMATION: Antisense oligonucleotides

<400> SEQUENCE: 2
gctccagaca tcact                                                     15

<210> SEQ ID NO 3
<211> LENGTH: 15
<212> TYPE: DNA
<213> ORGANISM: Artificial
<220> FEATURE:
<223> OTHER INFORMATION: Antisense oligonucleotides

<400> SEQUENCE: 3
ctccagacat cactc                                                     15

<210> SEQ ID NO 4
<211> LENGTH: 14
<212> TYPE: DNA
<213> ORGANISM: Artificial
<220> FEATURE:
<223> OTHER INFORMATION: Antisense oligonucleotides

<400> SEQUENCE: 4
gctccagaca tcac                                                      14

<210> SEQ ID NO 5
<211> LENGTH: 14
<212> TYPE: DNA
<213> ORGANISM: Artificial
<220> FEATURE:
<223> OTHER INFORMATION: Antisense oligonucleotides

<400> SEQUENCE: 5
ctccagacat cact                                                      14

<210> SEQ ID NO 6
<211> LENGTH: 14
<212> TYPE: DNA
<213> ORGANISM: Artificial
<220> FEATURE:
<223> OTHER INFORMATION: Antisense oligonucleotides

<400> SEQUENCE: 6
tccagacatc actc                                                      14

<210> SEQ ID NO 7
<211> LENGTH: 13
<212> TYPE: DNA
<213> ORGANISM: Artificial
<220> FEATURE:
<223> OTHER INFORMATION: Antisense oligonucleotides

<400> SEQUENCE: 7
gctccagaca tca                                                       13

<210> SEQ ID NO 8
<211> LENGTH: 13
<212> TYPE: DNA
<213> ORGANISM: Artificial
<220> FEATURE:
```

<223> OTHER INFORMATION: Antisense oligonucleotides

<400> SEQUENCE: 8
ctccagacat cac                                                          13

<210> SEQ ID NO 9
<211> LENGTH: 13
<212> TYPE: DNA
<213> ORGANISM: Artificial
<220> FEATURE:
<223> OTHER INFORMATION: Antisense oligonucleotides

<400> SEQUENCE: 9
tccagacatc act                                                          13

<210> SEQ ID NO 10
<211> LENGTH: 13
<212> TYPE: DNA
<213> ORGANISM: Artificial
<220> FEATURE:
<223> OTHER INFORMATION: Antisense oligonucleotides

<400> SEQUENCE: 10
ccagacatca ctc                                                          13

<210> SEQ ID NO 11
<211> LENGTH: 12
<212> TYPE: DNA
<213> ORGANISM: Artificial
<220> FEATURE:
<223> OTHER INFORMATION: Antisense oligonucleotides

<400> SEQUENCE: 11
gctccagaca tc                                                           12

<210> SEQ ID NO 12
<211> LENGTH: 12
<212> TYPE: DNA
<213> ORGANISM: Artificial
<220> FEATURE:
<223> OTHER INFORMATION: Antisense oligonucleotides

<400> SEQUENCE: 12
ctccagacat ca                                                           12

<210> SEQ ID NO 13
<211> LENGTH: 12
<212> TYPE: DNA
<213> ORGANISM: Artificial
<220> FEATURE:
<223> OTHER INFORMATION: Antisense oligonucleotides

<400> SEQUENCE: 13
tccagacatc ac                                                           12

<210> SEQ ID NO 14
<211> LENGTH: 12
<212> TYPE: DNA
<213> ORGANISM: Artificial
<220> FEATURE:
<223> OTHER INFORMATION: Antisense oligonucleotides

<400> SEQUENCE: 14
ccagacatca ct                                                           12

<210> SEQ ID NO 15

```
<211> LENGTH: 12
<212> TYPE: DNA
<213> ORGANISM: Artificial
<220> FEATURE:
<223> OTHER INFORMATION: Antisense oligonucleotides

<400> SEQUENCE: 15
cagacatcac tc                                                            12

<210> SEQ ID NO 16
<211> LENGTH: 16
<212> TYPE: DNA
<213> ORGANISM: Artificial
<220> FEATURE:
<223> OTHER INFORMATION: Antisense oligonucleotides

<400> SEQUENCE: 16
ctccagacat cactct                                                        16

<210> SEQ ID NO 17
<211> LENGTH: 16
<212> TYPE: DNA
<213> ORGANISM: Artificial
<220> FEATURE:
<223> OTHER INFORMATION: Antisense oligonucleotides

<400> SEQUENCE: 17
cagacatcac tctggt                                                        16

<210> SEQ ID NO 18
<211> LENGTH: 16
<212> TYPE: DNA
<213> ORGANISM: Artificial
<220> FEATURE:
<223> OTHER INFORMATION: Antisense oligonucleotides

<400> SEQUENCE: 18
agacatcact ctggtg                                                        16

<210> SEQ ID NO 19
<211> LENGTH: 16
<212> TYPE: DNA
<213> ORGANISM: Artificial
<220> FEATURE:
<223> OTHER INFORMATION: Antisense oligonucleotides

<400> SEQUENCE: 19
atagctccag acatca                                                        16

<210> SEQ ID NO 20
<211> LENGTH: 15
<212> TYPE: DNA
<213> ORGANISM: Artificial
<220> FEATURE:
<223> OTHER INFORMATION: Antisense oligonucleotides

<400> SEQUENCE: 20
atagctccag acatc                                                         15

<210> SEQ ID NO 21
<211> LENGTH: 15
<212> TYPE: DNA
<213> ORGANISM: Artificial
<220> FEATURE:
<223> OTHER INFORMATION: Antisense oligonucleotides

<400> SEQUENCE: 21
```
tagctccaga catca                                                    15

<210> SEQ ID NO 22
<211> LENGTH: 14
<212> TYPE: DNA
<213> ORGANISM: Artificial
<220> FEATURE:
<223> OTHER INFORMATION: Antisense oligonucleotides

<400> SEQUENCE: 22
atagctccag acat                                                     14

<210> SEQ ID NO 23
<211> LENGTH: 14
<212> TYPE: DNA
<213> ORGANISM: Artificial
<220> FEATURE:
<223> OTHER INFORMATION: Antisense oligonucleotides

<400> SEQUENCE: 23
tagctccaga catc                                                     14

<210> SEQ ID NO 24
<211> LENGTH: 14
<212> TYPE: DNA
<213> ORGANISM: Artificial
<220> FEATURE:
<223> OTHER INFORMATION: Antisense oligonucleotides

<400> SEQUENCE: 24
agctccagac atca                                                     14

<210> SEQ ID NO 25
<211> LENGTH: 13
<212> TYPE: DNA
<213> ORGANISM: Artificial
<220> FEATURE:
<223> OTHER INFORMATION: Antisense oligonucleotides

<400> SEQUENCE: 25
atagctccag aca                                                      13

<210> SEQ ID NO 26
<211> LENGTH: 13
<212> TYPE: DNA
<213> ORGANISM: Artificial
<220> FEATURE:
<223> OTHER INFORMATION: Antisense oligonucleotides

<400> SEQUENCE: 26
tagctccaga cat                                                      13

<210> SEQ ID NO 27
<211> LENGTH: 13
<212> TYPE: DNA
<213> ORGANISM: Artificial
<220> FEATURE:
<223> OTHER INFORMATION: Antisense oligonucleotides

<400> SEQUENCE: 27
agctccagac atc                                                      13

<210> SEQ ID NO 28
<211> LENGTH: 13
<212> TYPE: DNA
<213> ORGANISM: Artificial
<220> FEATURE:

-continued

<223> OTHER INFORMATION: Antisense oligonucleotides

<400> SEQUENCE: 28
gctccagaca tca                                                        13

<210> SEQ ID NO 29
<211> LENGTH: 12
<212> TYPE: DNA
<213> ORGANISM: Artificial
<220> FEATURE:
<223> OTHER INFORMATION: Antisense oligonucleotides

<400> SEQUENCE: 29
atagctccag ac                                                         12

<210> SEQ ID NO 30
<211> LENGTH: 12
<212> TYPE: DNA
<213> ORGANISM: Artificial
<220> FEATURE:
<223> OTHER INFORMATION: Antisense oligonucleotides

<400> SEQUENCE: 30
tagctccaga ca                                                         12

<210> SEQ ID NO 31
<211> LENGTH: 12
<212> TYPE: DNA
<213> ORGANISM: Artificial
<220> FEATURE:
<223> OTHER INFORMATION: Antisense oligonucleotides

<400> SEQUENCE: 31
agctccagac at                                                         12

<210> SEQ ID NO 32
<211> LENGTH: 12
<212> TYPE: DNA
<213> ORGANISM: Artificial
<220> FEATURE:
<223> OTHER INFORMATION: Antisense oligonucleotides

<400> SEQUENCE: 32
gctccagaca tc                                                         12

<210> SEQ ID NO 33
<211> LENGTH: 12
<212> TYPE: DNA
<213> ORGANISM: Artificial
<220> FEATURE:
<223> OTHER INFORMATION: Antisense oligonucleotides

<400> SEQUENCE: 33
ctccagacat ca                                                         12

<210> SEQ ID NO 34
<211> LENGTH: 16
<212> TYPE: DNA
<213> ORGANISM: Artificial
<220> FEATURE:
<223> OTHER INFORMATION: Antisense oligonucleotides

<400> SEQUENCE: 34
tcacaccata gctcca                                                     16

<210> SEQ ID NO 35

```
<211> LENGTH: 15
<212> TYPE: DNA
<213> ORGANISM: Artificial
<220> FEATURE:
<223> OTHER INFORMATION: Antisense oligonucleotides

<400> SEQUENCE: 35
tcacaccata gctcc                                                    15

<210> SEQ ID NO 36
<211> LENGTH: 15
<212> TYPE: DNA
<213> ORGANISM: Artificial
<220> FEATURE:
<223> OTHER INFORMATION: Antisense oligonucleotides

<400> SEQUENCE: 36
cacaccatag ctcca                                                    15

<210> SEQ ID NO 37
<211> LENGTH: 14
<212> TYPE: DNA
<213> ORGANISM: Artificial
<220> FEATURE:
<223> OTHER INFORMATION: Antisense oligonucleotides

<400> SEQUENCE: 37
tcacaccata gctc                                                     14

<210> SEQ ID NO 38
<211> LENGTH: 14
<212> TYPE: DNA
<213> ORGANISM: Artificial
<220> FEATURE:
<223> OTHER INFORMATION: Antisense oligonucleotides

<400> SEQUENCE: 38
cacaccatag ctcc                                                     14

<210> SEQ ID NO 39
<211> LENGTH: 14
<212> TYPE: DNA
<213> ORGANISM: Artificial
<220> FEATURE:
<223> OTHER INFORMATION: Antisense oligonucleotides

<400> SEQUENCE: 39
acaccatagc tcca                                                     14

<210> SEQ ID NO 40
<211> LENGTH: 13
<212> TYPE: DNA
<213> ORGANISM: Artificial
<220> FEATURE:
<223> OTHER INFORMATION: Antisense oligonucleotides

<400> SEQUENCE: 40
tcacaccata gct                                                      13

<210> SEQ ID NO 41
<211> LENGTH: 13
<212> TYPE: DNA
<213> ORGANISM: Artificial
<220> FEATURE:
<223> OTHER INFORMATION: Antisense oligonucleotides

<400> SEQUENCE: 41
```

```
cacaccatag ctc                                                    13
```

<210> SEQ ID NO 42
<211> LENGTH: 13
<212> TYPE: DNA
<213> ORGANISM: Artificial
<220> FEATURE:
<223> OTHER INFORMATION: Antisense oligonucleotides

<400> SEQUENCE: 42

```
acaccatagc tcc                                                    13
```

<210> SEQ ID NO 43
<211> LENGTH: 13
<212> TYPE: DNA
<213> ORGANISM: Artificial
<220> FEATURE:
<223> OTHER INFORMATION: Antisense oligonucleotides

<400> SEQUENCE: 43

```
caccatagct cca                                                    13
```

<210> SEQ ID NO 44
<211> LENGTH: 12
<212> TYPE: DNA
<213> ORGANISM: Artificial
<220> FEATURE:
<223> OTHER INFORMATION: Antisense oligonucleotides

<400> SEQUENCE: 44

```
tcacaccata gc                                                     12
```

<210> SEQ ID NO 45
<211> LENGTH: 12
<212> TYPE: DNA
<213> ORGANISM: Artificial
<220> FEATURE:
<223> OTHER INFORMATION: Antisense oligonucleotides

<400> SEQUENCE: 45

```
cacaccatag ct                                                     12
```

<210> SEQ ID NO 46
<211> LENGTH: 12
<212> TYPE: DNA
<213> ORGANISM: Artificial
<220> FEATURE:
<223> OTHER INFORMATION: Antisense oligonucleotides

<400> SEQUENCE: 46

```
acaccatagc tc                                                     12
```

<210> SEQ ID NO 47
<211> LENGTH: 12
<212> TYPE: DNA
<213> ORGANISM: Artificial
<220> FEATURE:
<223> OTHER INFORMATION: Antisense oligonucleotides

<400> SEQUENCE: 47

```
caccatagct cc                                                     12
```

<210> SEQ ID NO 48
<211> LENGTH: 12
<212> TYPE: DNA
<213> ORGANISM: Artificial
<220> FEATURE:

-continued

```
<223> OTHER INFORMATION: Antisense oligonucleotides

<400> SEQUENCE: 48
accatagctc ca                                                          12

<210> SEQ ID NO 49
<211> LENGTH: 16
<212> TYPE: DNA
<213> ORGANISM: Artificial
<220> FEATURE:
<223> OTHER INFORMATION: Antisense oligonucleotides

<400> SEQUENCE: 49
catccaacac ttgacc                                                      16

<210> SEQ ID NO 50
<211> LENGTH: 16
<212> TYPE: DNA
<213> ORGANISM: Artificial
<220> FEATURE:
<223> OTHER INFORMATION: Antisense oligonucleotides

<400> SEQUENCE: 50
atccaacact tgacca                                                      16

<210> SEQ ID NO 51
<211> LENGTH: 16
<212> TYPE: DNA
<213> ORGANISM: Artificial
<220> FEATURE:
<223> OTHER INFORMATION: Antisense oligonucleotides

<400> SEQUENCE: 51
caatcatcca acactt                                                      16

<210> SEQ ID NO 52
<211> LENGTH: 16
<212> TYPE: DNA
<213> ORGANISM: Artificial
<220> FEATURE:
<223> OTHER INFORMATION: Antisense oligonucleotides

<400> SEQUENCE: 52
tcaatcatcc aacact                                                      16

<210> SEQ ID NO 53
<211> LENGTH: 16
<212> TYPE: DNA
<213> ORGANISM: Artificial
<220> FEATURE:
<223> OTHER INFORMATION: Antisense oligonucleotides

<400> SEQUENCE: 53
catgtagaca tcaatt                                                      16

<210> SEQ ID NO 54
<211> LENGTH: 16
<212> TYPE: DNA
<213> ORGANISM: Artificial
<220> FEATURE:
<223> OTHER INFORMATION: Antisense oligonucleotides

<400> SEQUENCE: 54
tagcctgtca cttctc                                                      16

<210> SEQ ID NO 55
```

```
<211> LENGTH: 16
<212> TYPE: DNA
<213> ORGANISM: Artificial
<220> FEATURE:
<223> OTHER INFORMATION: Antisense oligonucleotides

<400> SEQUENCE: 55
agatggcaaa cttccc                                                    16

<210> SEQ ID NO 56
<211> LENGTH: 16
<212> TYPE: DNA
<213> ORGANISM: Artificial
<220> FEATURE:
<223> OTHER INFORMATION: Antisense oligonucleotides

<400> SEQUENCE: 56
caaggctcac acatct                                                    16

<210> SEQ ID NO 57
<211> LENGTH: 16
<212> TYPE: DNA
<213> ORGANISM: Artificial
<220> FEATURE:
<223> OTHER INFORMATION: Antisense oligonucleotides

<400> SEQUENCE: 57
aagtccaggt tgccca                                                    16

<210> SEQ ID NO 58
<211> LENGTH: 16
<212> TYPE: DNA
<213> ORGANISM: Artificial
<220> FEATURE:
<223> OTHER INFORMATION: Antisense oligonucleotides

<400> SEQUENCE: 58
cattcaagtt cttcat                                                    16

<210> SEQ ID NO 59
<211> LENGTH: 16
<212> TYPE: DNA
<213> ORGANISM: Artificial
<220> FEATURE:
<223> OTHER INFORMATION: Antisense oligonucleotides

<400> SEQUENCE: 59
cactaatttc cttcag                                                    16

<210> SEQ ID NO 60
<211> LENGTH: 15
<212> TYPE: DNA
<213> ORGANISM: Artificial
<220> FEATURE:
<223> OTHER INFORMATION: Antisense oligonucleotides

<400> SEQUENCE: 60
cactaatttc cttca                                                     15

<210> SEQ ID NO 61
<211> LENGTH: 15
<212> TYPE: DNA
<213> ORGANISM: Artificial
<220> FEATURE:
<223> OTHER INFORMATION: Antisense oligonucleotides

<400> SEQUENCE: 61
```

```
actaatttcc ttcag                                                    15

<210> SEQ ID NO 62
<211> LENGTH: 14
<212> TYPE: DNA
<213> ORGANISM: Artificial
<220> FEATURE:
<223> OTHER INFORMATION: Antisense oligonucleotides

<400> SEQUENCE: 62
cactaatttc cttc                                                     14

<210> SEQ ID NO 63
<211> LENGTH: 14
<212> TYPE: DNA
<213> ORGANISM: Artificial
<220> FEATURE:
<223> OTHER INFORMATION: Antisense oligonucleotides

<400> SEQUENCE: 63
actaatttcc ttca                                                     14

<210> SEQ ID NO 64
<211> LENGTH: 14
<212> TYPE: DNA
<213> ORGANISM: Artificial
<220> FEATURE:
<223> OTHER INFORMATION: Antisense oligonucleotides

<400> SEQUENCE: 64
ctaatttcct tcag                                                     14

<210> SEQ ID NO 65
<211> LENGTH: 13
<212> TYPE: DNA
<213> ORGANISM: Artificial
<220> FEATURE:
<223> OTHER INFORMATION: Antisense oligonucleotides

<400> SEQUENCE: 65
cactaatttc ctt                                                      13

<210> SEQ ID NO 66
<211> LENGTH: 13
<212> TYPE: DNA
<213> ORGANISM: Artificial
<220> FEATURE:
<223> OTHER INFORMATION: Antisense oligonucleotides

<400> SEQUENCE: 66
actaatttcc ttc                                                      13

<210> SEQ ID NO 67
<211> LENGTH: 13
<212> TYPE: DNA
<213> ORGANISM: Artificial
<220> FEATURE:
<223> OTHER INFORMATION: Antisense oligonucleotides

<400> SEQUENCE: 67
ctaatttcct tca                                                      13

<210> SEQ ID NO 68
<211> LENGTH: 13
<212> TYPE: DNA
<213> ORGANISM: Artificial
<220> FEATURE:
```

```
<223> OTHER INFORMATION: Antisense oligonucleotides

<400> SEQUENCE: 68
taatttcctt cag                                                          13

<210> SEQ ID NO 69
<211> LENGTH: 12
<212> TYPE: DNA
<213> ORGANISM: Artificial
<220> FEATURE:
<223> OTHER INFORMATION: Antisense oligonucleotides

<400> SEQUENCE: 69
cactaatttc ct                                                           12

<210> SEQ ID NO 70
<211> LENGTH: 12
<212> TYPE: DNA
<213> ORGANISM: Artificial
<220> FEATURE:
<223> OTHER INFORMATION: Antisense oligonucleotides

<400> SEQUENCE: 70
actaatttcc tt                                                           12

<210> SEQ ID NO 71
<211> LENGTH: 12
<212> TYPE: DNA
<213> ORGANISM: Artificial
<220> FEATURE:
<223> OTHER INFORMATION: Antisense oligonucleotides

<400> SEQUENCE: 71
ctaatttcct tc                                                           12

<210> SEQ ID NO 72
<211> LENGTH: 12
<212> TYPE: DNA
<213> ORGANISM: Artificial
<220> FEATURE:
<223> OTHER INFORMATION: Antisense oligonucleotides

<400> SEQUENCE: 72
taatttcctt ca                                                           12

<210> SEQ ID NO 73
<211> LENGTH: 12
<212> TYPE: DNA
<213> ORGANISM: Artificial
<220> FEATURE:
<223> OTHER INFORMATION: Antisense oligonucleotides

<400> SEQUENCE: 73
aatttccttc ag                                                           12

<210> SEQ ID NO 74
<211> LENGTH: 16
<212> TYPE: DNA
<213> ORGANISM: Artificial
<220> FEATURE:
<223> OTHER INFORMATION: Antisense oligonucleotides

<400> SEQUENCE: 74
gcccagcact aatttc                                                       16

<210> SEQ ID NO 75
```

```
<211> LENGTH: 16
<212> TYPE: DNA
<213> ORGANISM: Artificial
<220> FEATURE:
<223> OTHER INFORMATION: Antisense oligonucleotides

<400> SEQUENCE: 75
ctttgccctc tgccac                                                    16

<210> SEQ ID NO 76
<211> LENGTH: 16
<212> TYPE: DNA
<213> ORGANISM: Artificial
<220> FEATURE:
<223> OTHER INFORMATION: Antisense oligonucleotides

<400> SEQUENCE: 76
cacacacttt gccctc                                                    16

<210> SEQ ID NO 77
<211> LENGTH: 15
<212> TYPE: DNA
<213> ORGANISM: Artificial
<220> FEATURE:
<223> OTHER INFORMATION: Antisense oligonucleotides

<400> SEQUENCE: 77
cacacacttt gccct                                                     15

<210> SEQ ID NO 78
<211> LENGTH: 15
<212> TYPE: DNA
<213> ORGANISM: Artificial
<220> FEATURE:
<223> OTHER INFORMATION: Antisense oligonucleotides

<400> SEQUENCE: 78
acacactttg ccctc                                                     15

<210> SEQ ID NO 79
<211> LENGTH: 14
<212> TYPE: DNA
<213> ORGANISM: Artificial
<220> FEATURE:
<223> OTHER INFORMATION: Antisense oligonucleotides

<400> SEQUENCE: 79
cacacacttt gccc                                                      14

<210> SEQ ID NO 80
<211> LENGTH: 14
<212> TYPE: DNA
<213> ORGANISM: Artificial
<220> FEATURE:
<223> OTHER INFORMATION: Antisense oligonucleotides

<400> SEQUENCE: 80
acacactttg ccct                                                      14

<210> SEQ ID NO 81
<211> LENGTH: 14
<212> TYPE: DNA
<213> ORGANISM: Artificial
<220> FEATURE:
<223> OTHER INFORMATION: Antisense oligonucleotides

<400> SEQUENCE: 81
```

```
cacactttgc cctc                                                     14

<210> SEQ ID NO 82
<211> LENGTH: 13
<212> TYPE: DNA
<213> ORGANISM: Artificial
<220> FEATURE:
<223> OTHER INFORMATION: Antisense oligonucleotides

<400> SEQUENCE: 82
cacacacttt gcc                                                      13

<210> SEQ ID NO 83
<211> LENGTH: 13
<212> TYPE: DNA
<213> ORGANISM: Artificial
<220> FEATURE:
<223> OTHER INFORMATION: Antisense oligonucleotides

<400> SEQUENCE: 83
acacactttg ccc                                                      13

<210> SEQ ID NO 84
<211> LENGTH: 13
<212> TYPE: DNA
<213> ORGANISM: Artificial
<220> FEATURE:
<223> OTHER INFORMATION: Antisense oligonucleotides

<400> SEQUENCE: 84
cacactttgc cct                                                      13

<210> SEQ ID NO 85
<211> LENGTH: 13
<212> TYPE: DNA
<213> ORGANISM: Artificial
<220> FEATURE:
<223> OTHER INFORMATION: Antisense oligonucleotides

<400> SEQUENCE: 85
acactttgcc ctc                                                      13

<210> SEQ ID NO 86
<211> LENGTH: 12
<212> TYPE: DNA
<213> ORGANISM: Artificial
<220> FEATURE:
<223> OTHER INFORMATION: Antisense oligonucleotides

<400> SEQUENCE: 86
cacacacttt gc                                                       12

<210> SEQ ID NO 87
<211> LENGTH: 12
<212> TYPE: DNA
<213> ORGANISM: Artificial
<220> FEATURE:
<223> OTHER INFORMATION: Antisense oligonucleotides

<400> SEQUENCE: 87
acacactttg cc                                                       12

<210> SEQ ID NO 88
<211> LENGTH: 12
<212> TYPE: DNA
<213> ORGANISM: Artificial
<220> FEATURE:
```

<223> OTHER INFORMATION: Antisense oligonucleotides

<400> SEQUENCE: 88
cacactttgc cc                                                            12

<210> SEQ ID NO 89
<211> LENGTH: 12
<212> TYPE: DNA
<213> ORGANISM: Artificial
<220> FEATURE:
<223> OTHER INFORMATION: Antisense oligonucleotides

<400> SEQUENCE: 89
acactttgcc ct                                                            12

<210> SEQ ID NO 90
<211> LENGTH: 12
<212> TYPE: DNA
<213> ORGANISM: Artificial
<220> FEATURE:
<223> OTHER INFORMATION: Antisense oligonucleotides

<400> SEQUENCE: 90
cactttgccc tc                                                            12

<210> SEQ ID NO 91
<211> LENGTH: 16
<212> TYPE: DNA
<213> ORGANISM: Artificial
<220> FEATURE:
<223> OTHER INFORMATION: Antisense oligonucleotides

<400> SEQUENCE: 91
cagttccaaa gacacc                                                        16

<210> SEQ ID NO 92
<211> LENGTH: 16
<212> TYPE: DNA
<213> ORGANISM: Artificial
<220> FEATURE:
<223> OTHER INFORMATION: Antisense oligonucleotides

<400> SEQUENCE: 92
tggcaatttg tactcc                                                        16

<210> SEQ ID NO 93
<211> LENGTH: 15
<212> TYPE: DNA
<213> ORGANISM: Artificial
<220> FEATURE:
<223> OTHER INFORMATION: Antisense oligonucleotides

<400> SEQUENCE: 93
tggcaatttg tactc                                                         15

<210> SEQ ID NO 94
<211> LENGTH: 15
<212> TYPE: DNA
<213> ORGANISM: Artificial
<220> FEATURE:
<223> OTHER INFORMATION: Antisense oligonucleotides

<400> SEQUENCE: 94
ggcaatttgt actcc                                                         15

<210> SEQ ID NO 95

```
<211> LENGTH: 14
<212> TYPE: DNA
<213> ORGANISM: Artificial
<220> FEATURE:
<223> OTHER INFORMATION: Antisense oligonucleotides

<400> SEQUENCE: 95
tggcaatttg tact                                                    14

<210> SEQ ID NO 96
<211> LENGTH: 14
<212> TYPE: DNA
<213> ORGANISM: Artificial
<220> FEATURE:
<223> OTHER INFORMATION: Antisense oligonucleotides

<400> SEQUENCE: 96
ggcaatttgt actc                                                    14

<210> SEQ ID NO 97
<211> LENGTH: 14
<212> TYPE: DNA
<213> ORGANISM: Artificial
<220> FEATURE:
<223> OTHER INFORMATION: Antisense oligonucleotides

<400> SEQUENCE: 97
gcaatttgta ctcc                                                    14

<210> SEQ ID NO 98
<211> LENGTH: 13
<212> TYPE: DNA
<213> ORGANISM: Artificial
<220> FEATURE:
<223> OTHER INFORMATION: Antisense oligonucleotides

<400> SEQUENCE: 98
tggcaatttg tac                                                     13

<210> SEQ ID NO 99
<211> LENGTH: 13
<212> TYPE: DNA
<213> ORGANISM: Artificial
<220> FEATURE:
<223> OTHER INFORMATION: Antisense oligonucleotides

<400> SEQUENCE: 99
ggcaatttgt act                                                     13

<210> SEQ ID NO 100
<211> LENGTH: 13
<212> TYPE: DNA
<213> ORGANISM: Artificial
<220> FEATURE:
<223> OTHER INFORMATION: Antisense oligonucleotides

<400> SEQUENCE: 100
gcaatttgta ctc                                                     13

<210> SEQ ID NO 101
<211> LENGTH: 13
<212> TYPE: DNA
<213> ORGANISM: Artificial
<220> FEATURE:
<223> OTHER INFORMATION: Antisense oligonucleotides

<400> SEQUENCE: 101
```

```
caatttgtac tcc                                                     13

<210> SEQ ID NO 102
<211> LENGTH: 12
<212> TYPE: DNA
<213> ORGANISM: Artificial
<220> FEATURE:
<223> OTHER INFORMATION: Antisense oligonucleotides

<400> SEQUENCE: 102
tggcaatttg ta                                                      12

<210> SEQ ID NO 103
<211> LENGTH: 12
<212> TYPE: DNA
<213> ORGANISM: Artificial
<220> FEATURE:
<223> OTHER INFORMATION: Antisense oligonucleotides

<400> SEQUENCE: 103
ggcaatttgt ac                                                      12

<210> SEQ ID NO 104
<211> LENGTH: 12
<212> TYPE: DNA
<213> ORGANISM: Artificial
<220> FEATURE:
<223> OTHER INFORMATION: Antisense oligonucleotides

<400> SEQUENCE: 104
gcaatttgta ct                                                      12

<210> SEQ ID NO 105
<211> LENGTH: 12
<212> TYPE: DNA
<213> ORGANISM: Artificial
<220> FEATURE:
<223> OTHER INFORMATION: Antisense oligonucleotides

<400> SEQUENCE: 105
caatttgtac tc                                                      12

<210> SEQ ID NO 106
<211> LENGTH: 12
<212> TYPE: DNA
<213> ORGANISM: Artificial
<220> FEATURE:
<223> OTHER INFORMATION: Antisense oligonucleotides

<400> SEQUENCE: 106
aatttgtact cc                                                      12

<210> SEQ ID NO 107
<211> LENGTH: 16
<212> TYPE: DNA
<213> ORGANISM: Artificial
<220> FEATURE:
<223> OTHER INFORMATION: Antisense oligonucleotides

<400> SEQUENCE: 107
gtgtgtgtat ttccca                                                  16

<210> SEQ ID NO 108
<211> LENGTH: 15
<212> TYPE: DNA
<213> ORGANISM: Artificial
<220> FEATURE:
```

```
<223> OTHER INFORMATION: Antisense oligonucleotides

<400> SEQUENCE: 108
gtgtgtgtat ttccc                                                    15

<210> SEQ ID NO 109
<211> LENGTH: 15
<212> TYPE: DNA
<213> ORGANISM: Artificial
<220> FEATURE:
<223> OTHER INFORMATION: Antisense oligonucleotides

<400> SEQUENCE: 109
tgtgtgtatt tccca                                                    15

<210> SEQ ID NO 110
<211> LENGTH: 14
<212> TYPE: DNA
<213> ORGANISM: Artificial
<220> FEATURE:
<223> OTHER INFORMATION: Antisense oligonucleotides

<400> SEQUENCE: 110
gtgtgtgtat ttcc                                                     14

<210> SEQ ID NO 111
<211> LENGTH: 14
<212> TYPE: DNA
<213> ORGANISM: Artificial
<220> FEATURE:
<223> OTHER INFORMATION: Antisense oligonucleotides

<400> SEQUENCE: 111
tgtgtgtatt tccc                                                     14

<210> SEQ ID NO 112
<211> LENGTH: 14
<212> TYPE: DNA
<213> ORGANISM: Artificial
<220> FEATURE:
<223> OTHER INFORMATION: Antisense oligonucleotides

<400> SEQUENCE: 112
gtgtgtattt ccca                                                     14

<210> SEQ ID NO 113
<211> LENGTH: 13
<212> TYPE: DNA
<213> ORGANISM: Artificial
<220> FEATURE:
<223> OTHER INFORMATION: Antisense oligonucleotides

<400> SEQUENCE: 113
gtgtgtgtat ttc                                                      13

<210> SEQ ID NO 114
<211> LENGTH: 13
<212> TYPE: DNA
<213> ORGANISM: Artificial
<220> FEATURE:
<223> OTHER INFORMATION: Antisense oligonucleotides

<400> SEQUENCE: 114
tgtgtgtatt tcc                                                      13

<210> SEQ ID NO 115
```

```
<211> LENGTH: 13
<212> TYPE: DNA
<213> ORGANISM: Artificial
<220> FEATURE:
<223> OTHER INFORMATION: Antisense oligonucleotides

<400> SEQUENCE: 115
gtgtgtattt ccc                                                          13

<210> SEQ ID NO 116
<211> LENGTH: 13
<212> TYPE: DNA
<213> ORGANISM: Artificial
<220> FEATURE:
<223> OTHER INFORMATION: Antisense oligonucleotides

<400> SEQUENCE: 116
tgtgtatttc cca                                                          13

<210> SEQ ID NO 117
<211> LENGTH: 12
<212> TYPE: DNA
<213> ORGANISM: Artificial
<220> FEATURE:
<223> OTHER INFORMATION: Antisense oligonucleotides

<400> SEQUENCE: 117
gtgtgtgtat tt                                                           12

<210> SEQ ID NO 118
<211> LENGTH: 12
<212> TYPE: DNA
<213> ORGANISM: Artificial
<220> FEATURE:
<223> OTHER INFORMATION: Antisense oligonucleotides

<400> SEQUENCE: 118
tgtgtgtatt tc                                                           12

<210> SEQ ID NO 119
<211> LENGTH: 12
<212> TYPE: DNA
<213> ORGANISM: Artificial
<220> FEATURE:
<223> OTHER INFORMATION: Antisense oligonucleotides

<400> SEQUENCE: 119
gtgtgtattt cc                                                           12

<210> SEQ ID NO 120
<211> LENGTH: 12
<212> TYPE: DNA
<213> ORGANISM: Artificial
<220> FEATURE:
<223> OTHER INFORMATION: Antisense oligonucleotides

<400> SEQUENCE: 120
tgtgtatttc cc                                                           12

<210> SEQ ID NO 121
<211> LENGTH: 12
<212> TYPE: DNA
<213> ORGANISM: Artificial
<220> FEATURE:
<223> OTHER INFORMATION: Antisense oligonucleotides

<400> SEQUENCE: 121
```

-continued

```
gtgtatttcc ca                                                            12

<210> SEQ ID NO 122
<211> LENGTH: 16
<212> TYPE: DNA
<213> ORGANISM: Artificial
<220> FEATURE:
<223> OTHER INFORMATION: Antisense oligonucleotides

<400> SEQUENCE: 122
ccctctgatg actctg                                                        16

<210> SEQ ID NO 123
<211> LENGTH: 15
<212> TYPE: DNA
<213> ORGANISM: Artificial
<220> FEATURE:
<223> OTHER INFORMATION: Antisense oligonucleotides

<400> SEQUENCE: 123
ccctctgatg actct                                                         15

<210> SEQ ID NO 124
<211> LENGTH: 15
<212> TYPE: DNA
<213> ORGANISM: Artificial
<220> FEATURE:
<223> OTHER INFORMATION: Antisense oligonucleotides

<400> SEQUENCE: 124
cctctgatga ctctg                                                         15

<210> SEQ ID NO 125
<211> LENGTH: 14
<212> TYPE: DNA
<213> ORGANISM: Artificial
<220> FEATURE:
<223> OTHER INFORMATION: Antisense oligonucleotides

<400> SEQUENCE: 125
ccctctgatg actc                                                          14

<210> SEQ ID NO 126
<211> LENGTH: 14
<212> TYPE: DNA
<213> ORGANISM: Artificial
<220> FEATURE:
<223> OTHER INFORMATION: Antisense oligonucleotides

<400> SEQUENCE: 126
cctctgatga ctct                                                          14

<210> SEQ ID NO 127
<211> LENGTH: 14
<212> TYPE: DNA
<213> ORGANISM: Artificial
<220> FEATURE:
<223> OTHER INFORMATION: Antisense oligonucleotides

<400> SEQUENCE: 127
ctctgatgac tctg                                                          14

<210> SEQ ID NO 128
<211> LENGTH: 13
<212> TYPE: DNA
<213> ORGANISM: Artificial
<220> FEATURE:
```

```
<223> OTHER INFORMATION: Antisense oligonucleotides

<400> SEQUENCE: 128
ccctctgatg act                                                           13

<210> SEQ ID NO 129
<211> LENGTH: 13
<212> TYPE: DNA
<213> ORGANISM: Artificial
<220> FEATURE:
<223> OTHER INFORMATION: Antisense oligonucleotides

<400> SEQUENCE: 129
cctctgatga ctc                                                           13

<210> SEQ ID NO 130
<211> LENGTH: 13
<212> TYPE: DNA
<213> ORGANISM: Artificial
<220> FEATURE:
<223> OTHER INFORMATION: Antisense oligonucleotides

<400> SEQUENCE: 130
ctctgatgac tct                                                           13

<210> SEQ ID NO 131
<211> LENGTH: 13
<212> TYPE: DNA
<213> ORGANISM: Artificial
<220> FEATURE:
<223> OTHER INFORMATION: Antisense oligonucleotides

<400> SEQUENCE: 131
tctgatgact ctg                                                           13

<210> SEQ ID NO 132
<211> LENGTH: 12
<212> TYPE: DNA
<213> ORGANISM: Artificial
<220> FEATURE:
<223> OTHER INFORMATION: Antisense oligonucleotides

<400> SEQUENCE: 132
ccctctgatg ac                                                            12

<210> SEQ ID NO 133
<211> LENGTH: 12
<212> TYPE: DNA
<213> ORGANISM: Artificial
<220> FEATURE:
<223> OTHER INFORMATION: Antisense oligonucleotides

<400> SEQUENCE: 133
cctctgatga ct                                                            12

<210> SEQ ID NO 134
<211> LENGTH: 12
<212> TYPE: DNA
<213> ORGANISM: Artificial
<220> FEATURE:
<223> OTHER INFORMATION: Antisense oligonucleotides

<400> SEQUENCE: 134
ctctgatgac tc                                                            12

<210> SEQ ID NO 135
```

```
<211> LENGTH: 12
<212> TYPE: DNA
<213> ORGANISM: Artificial
<220> FEATURE:
<223> OTHER INFORMATION: Antisense oligonucleotides

<400> SEQUENCE: 135
tctgatgact ct                                                              12

<210> SEQ ID NO 136
<211> LENGTH: 12
<212> TYPE: DNA
<213> ORGANISM: Artificial
<220> FEATURE:
<223> OTHER INFORMATION: Antisense oligonucleotides

<400> SEQUENCE: 136
ctgatgactc tg                                                              12

<210> SEQ ID NO 137
<211> LENGTH: 16
<212> TYPE: DNA
<213> ORGANISM: Artificial
<220> FEATURE:
<223> OTHER INFORMATION: Antisense oligonucleotides

<400> SEQUENCE: 137
catactcctc atcttc                                                          16

<210> SEQ ID NO 138
<211> LENGTH: 16
<212> TYPE: DNA
<213> ORGANISM: Artificial
<220> FEATURE:
<223> OTHER INFORMATION: Antisense oligonucleotides

<400> SEQUENCE: 138
ccaccacaaa gttatg                                                          16

<210> SEQ ID NO 139
<211> LENGTH: 16
<212> TYPE: DNA
<213> ORGANISM: Artificial
<220> FEATURE:
<223> OTHER INFORMATION: Antisense oligonucleotides

<400> SEQUENCE: 139
catcactctg gtgtgt                                                          16

<210> SEQ ID NO 140
<211> LENGTH: 16
<212> TYPE: DNA
<213> ORGANISM: Artificial
<220> FEATURE:
<223> OTHER INFORMATION: Antisense oligonucleotides

<400> SEQUENCE: 140
gacatcactc tggtgt                                                          16

<210> SEQ ID NO 141
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
```

```
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 141
gctccagaca tcactc                                                   16

<210> SEQ ID NO 142
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 142
ctccagacat cactct                                                   16

<210> SEQ ID NO 143
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 143
cagacatcac tctggt                                                   16

<210> SEQ ID NO 144
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 144
agacatcact ctggtg                                                   16

<210> SEQ ID NO 145
<211> LENGTH: 16
<212> TYPE: DNA
<213> ORGANISM: Artificial
<220> FEATURE:
```

```
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 145
atagctccag acatca                                                    16

<210> SEQ ID NO 146
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 146
tcacaccata gctcca                                                    16

<210> SEQ ID NO 147
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 147
catccaacac ttgacc                                                    16

<210> SEQ ID NO 148
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 148
atccaacact tgacca                                                    16

<210> SEQ ID NO 149
```

```
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 149
caatcatcca acactt                                                    16

<210> SEQ ID NO 150
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 150
tcaatcatcc aacact                                                    16

<210> SEQ ID NO 151
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 151
catgtagaca tcaatt                                                    16

<210> SEQ ID NO 152
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 152
```

-continued tagcctgtca cttctc                                              16

<210> SEQ ID NO 153
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 153
agatggcaaa cttccc                                              16

<210> SEQ ID NO 154
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 154
caaggctcac acatct                                              16

<210> SEQ ID NO 155
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 155
aagtccaggt tgccca                                              16

<210> SEQ ID NO 156
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues

<222> LOCATION: (14)..(16)

<400> SEQUENCE: 156
cattcaagtt cttcat					16

<210> SEQ ID NO 157
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 157
cactaatttc cttcag					16

<210> SEQ ID NO 158
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 158
gcccagcact aatttc					16

<210> SEQ ID NO 159
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 159
ctttgccctc tgccac					16

<210> SEQ ID NO 160
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:

-continued

```
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 160 cacacactttt gccctc                                                    16

<210> SEQ ID NO 161
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 161
cagttccaaa gacacc                                                     16

<210> SEQ ID NO 162
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 162
tggcaatttg tactcc                                                     16

<210> SEQ ID NO 163
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 163
gtgtgtgtat ttccca                                                     16

<210> SEQ ID NO 164
<211> LENGTH: 16
<212> TYPE: DNA
<213> ORGANISM: Artificial
<220> FEATURE:
<223> OTHER INFORMATION: Oligonucleotide designs
```

```
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 164
ccctctgatg actctg                                                          16

<210> SEQ ID NO 165
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 165
catactcctc atcttc                                                          16

<210> SEQ ID NO 166
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 166
ccaccacaaa gttatg                                                          16

<210> SEQ ID NO 167
<211> LENGTH: 16
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 167
catcactctg gtgtgt                                                          16

<210> SEQ ID NO 168
<211> LENGTH: 16
```

```
<212> TYPE: DNA
<213> ORGANISM: Artificial
<220> FEATURE:
<223> OTHER INFORMATION: Oligonucleotide designs
<220> FEATURE:
<221> NAME/KEY: phosphorothiate linkage
<222> LOCATION: (1)..(15)
<220> FEATURE:
<221> NAME/KEY: nucleotide analogues
<222> LOCATION: (1)..(3)
<220> FEATURE:
<221> NAME/KEY: nucleotide analogues
<222> LOCATION: (14)..(16)

<400> SEQUENCE: 168
gacatcactc tggtgt                                              16

<210> SEQ ID NO 169
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 169
gctccagaca tcactc                                              16

<210> SEQ ID NO 170
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 170
ctccagacat cactct                                              16

<210> SEQ ID NO 171
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 171
cagacatcac tctggt                                              16
```

```
<210> SEQ ID NO 172
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 172
agacatcact ctggtg                                                     16

<210> SEQ ID NO 173
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 173
atagctccag acatca                                                     16

<210> SEQ ID NO 174
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 174
tcacaccata gctcca                                                     16

<210> SEQ ID NO 175
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)
```

-continued

<400> SEQUENCE: 175
catccaacac ttgacc                                                        16

<210> SEQ ID NO 176
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 176
atccaacact tgacca                                                        16

<210> SEQ ID NO 177
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 177
caatcatcca acactt                                                        16

<210> SEQ ID NO 178
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 178
tcaatcatcc aacact                                                        16

<210> SEQ ID NO 179
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases

```
<222> LOCATION: (1)..(3)
<220> FEATURE:
<221> NAME/KEY: LNA nucleobases
<222> LOCATION: (14)..(16)

<400> SEQUENCE: 179
catgtagaca tcaatt                                                      16

<210> SEQ ID NO 180
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 180
tagcctgtca cttctc                                                      16

<210> SEQ ID NO 181
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 181
agatggcaaa cttccc                                                      16

<210> SEQ ID NO 182
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 182
caaggctcac acatct                                                      16

<210> SEQ ID NO 183
<211> LENGTH: 16
<212> TYPE: DNA
<213> ORGANISM: Artificial
<220> FEATURE:
<223> OTHER INFORMATION: LNA oligomers
<220> FEATURE:
```

```
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 183
aagtccaggt tgccca                                              16

<210> SEQ ID NO 184
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 184
cattcaagtt cttcat                                              16

<210> SEQ ID NO 185
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 185
cactaatttc cttcag                                              16

<210> SEQ ID NO 186
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 186
gcccagcact aatttc                                              16

<210> SEQ ID NO 187
<211> LENGTH: 16
<212> TYPE: DNA
```

```
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 187
ctttgccctc tgccac                                                    16

<210> SEQ ID NO 188
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 188
cacacacttt gccctc                                                    16

<210> SEQ ID NO 189
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 189
cagttccaaa gacacc                                                    16

<210> SEQ ID NO 190
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 190
tggcaatttg tactcc                                                    16
```

```
<210> SEQ ID NO 191
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 191
gtgtgtgtat ttccca                                               16

<210> SEQ ID NO 192
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 192
ccctctgatg actctg                                               16

<210> SEQ ID NO 193
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 193
catactcctc atcttc                                               16

<210> SEQ ID NO 194
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)
```

<400> SEQUENCE: 194
ccaccacaaa gttatg                                                          16

<210> SEQ ID NO 195
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 195
catcactctg gtgtgt                                                          16

<210> SEQ ID NO 196
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
<220> FEATURE:
<221> NAME/KEY: LNA nucleobases
<222> LOCATION: (14)..(16)

<400> SEQUENCE: 196
gacatcactc tggtgt                                                          16

<210> SEQ ID NO 197
<211> LENGTH: 5511
<212> TYPE: DNA
<213> ORGANISM: homo sapiens

<400> SEQUENCE: 197
acacacacac acccctcccc tgccatccct ccccggactc cggctccggc tccgattgca      60
atttgcaacc tccgctgccg tcgccgcagc agccaccaat tcgccagcgg ttcaggtggc     120
tcttgcctcg atgtcctagc ctaggggccc ccgggccgga cttggctggg ctcccttcac     180
cctctgcgga gtcatgaggg cgaacgacgc tctgcaggtg ctgggcttgc ttttcagcct     240
ggcccggggc tccgaggtgg gcaactctca ggcagtgtgt cctgggactc tgaatggcct     300
gagtgtgacc ggcgatgctg agaaccaata ccagacactg tacaagctct acgagaggtg     360
tgaggtggtg atggggaacc ttgagattgt gctcacggga cacaatgccg acctctcctt     420
cctgcagtgg attcgagaag tgacaggcta tgtcctcgtg gccatgaatg aattctctac     480
tctaccattg cccaacctcc gcgtggtgcg agggacccag gtctacgatg ggaagtttgc     540
catcttcgtc atgttgaact ataacaccaa ctccagccac gctctgcgcc agctccgctt     600
gactcagctc accgagattc tgtcaggggg tgtttatatt gagaagaacg ataagctttg     660
tcacatggac acaattgact ggagggacat cgtgagggac cgagatgctg agatagtggt     720
gaaggacaat ggcagaagct gtccccctg tcatgaggtt tgcaagggc gatgctgggg    780

```
tcctggatca gaagactgcc agacattgac caagaccatc tgtgctcctc agtgtaatgg      840
tcactgcttt gggcccaacc ccaaccagtg ctgccatgat gagtgtgccg ggggctgctc      900
aggccctcag gacacagact gctttgcctg ccggcacttc aatgacagtg agcctgtgt       960 acctcgctgt ccacagcctc ttgtctacaa caagctaact ttccagctgg aacccaatcc     1020
ccacaccaag tatcagtatg gaggagtttg tgtagccagc tgtccccata actttgtggt     1080
ggatcaaaca tcctgtgtca gggcctgtcc tcctgacaag atggaagtag ataaaaatgg     1140
gctcaagatg tgtgagcctt gtggggact atgtcccaaa gcctgtgagg aacaggctc       1200 tgggagccgc ttccagactg tggactcgag caacattgat ggatttgtga actgcaccaa     1260
gatcctgggc aacctggact ttctgatcac cggcctcaat ggagacccct ggcacaagat     1320
ccctgccctg gacccagaga agctcaatgt cttccggaca gtacgggaga tcacaggtta     1380
cctgaacatc cagtcctggc cgccccacat gcacaacttc agtgtttttt ccaatttgac     1440
aaccattgga ggcagaagcc tctacaaccg gggcttctca ttgttgatca tgaagaactt     1500
gaatgtcaca tctctgggct tccgatccct gaaggaaatt agtgctgggc gtatctatat     1560
aagtgccaat aggcagctct gctaccacca ctctttgaac tggaccaagg tgcttcgggg     1620
gcctacggaa gagcgactag acatcaagca taatcggccg cgcagagact gcgtggcaga     1680
gggcaaagtg tgtgacccac tgtgctcctc tggggatgc tggggcccag gcctggtca      1740 gtgcttgtcc tgtcgaaatt atagccgagg aggtgtctgt gtgacccact gcaactttct     1800
gaatggggag cctcgagaat ttgcccatga ggccgaatgc ttctcctgcc acccggaatg     1860
ccaacccatg gagggcactg ccacatgcaa tggctcgggc tctgatactt gtgctcaatg     1920
tgcccatttt cgagatgggc cccactgtgt gagcagctgc ccccatgag tcctaggtgc       1980 caagggccca atctacaagt acccagatgt tcagaatgaa tgtcggccct gccatgagaa     2040
ctgcacccag gggtgtaaag gaccagagct tcaagactgt ttaggacaaa cactggtgct     2100
gatcggcaaa acccatctga caatggcttt gacagtgata gcaggattgg tagtgatttt     2160
catgatgctg gcggcacttt ttctctactg gcgtgggcgc cggattcaga ataaaagggc     2220
tatgaggcga tacttggaac ggggtgagag catagagcct ctggacccca gtgagaaggc     2280
taacaaagtc ttggccagaa tcttcaaaga gacagagcta aggaagctta aagtgcttgg     2340
ctcgggtgtc tttggaactg tgcacaaagg agtgtggatc cctgagggtg aatcaatcaa     2400
gattccagtc tgcattaaag tcattgagga caagagtgga cggcagagtt ttcaagctgt     2460
gacagatcat atgctggcca ttggcagcct ggaccatgcc cacattgtaa ggctgctggg     2520
actatgccca gggtcatctc tgcagcttgt cactcaatat ttgcctctgg gttctctgct     2580
ggatcatgtg agacaacacc gggggcact ggggccacag ctgctgctca actggggagt      2640
acaaattgcc aagggaatgt actaccttga ggaacatggt atggtgcata gaaacctggc     2700
tgcccgaaac gtgctactca agtcacccag tcaggttcag gtggcagatt ttggtgtggc     2760
tgacctgctg cctcctgatg ataagcagct gctatacagt gaggccaaga ctccaattaa     2820
gtggatggcc cttgagagta tccactttgg gaaatacaca caccagagtg atgtctggag     2880
ctatggtgtg acagtttggg agttgatgac cttcggggca gagccctatg cagggctacg     2940
attggctgaa gtaccagacc tgctagaaa ggggagcgg ttggcacagc cccagatctg        3000
cacaattgat gtctacatgg tgatggtcaa gtgttggatg attgatgaga acattcgccc     3060 aaccttt aaa gaactagcca atgagttcac caggatggcc cgagacccac acgggtatct    3120
ggtcataaag agagagagtg ggcctggaat agcccctggg ccagagcccc atggtctgac     3180
```

-continued

```
aaacaagaag ctagaggaag tagagctgga gccagaacta gacctagacc tagacttgga    3240
agcagaggag gacaacctgg caaccaccac actgggctcc gccctcagcc taccagttgg    3300
aacacttaat cggccacgtg ggagccagag ccttttaagt ccatcatctg gatacatgcc    3360
catgaaccag ggtaatcttg gggagtcttg ccaggagtct gcagtttctg ggagcagtga    3420
acggtgcccc cgtccagtct ctctacaccc aatgccacgg ggatgcctgg catcagagtc    3480
atcagagggg catgtaacag gctctgaggc tgagctccag gagaaagtgt caatgtgtag    3540
gagccggagc aggagccgga gcccacggcc acgcggagat agcgcctacc attcccagcg    3600
ccacagtctg ctgactcctg ttaccccact ctccccaccc gggttagagg aagaggatgt    3660
caacggttat gtcatgccag atacacacct caaaggtact ccctcctccc gggaaggcac    3720
cctttcttca gtgggtctca gttctgtcct gggtactgaa gaagaagatg aagatgagga    3780
gtatgaatac atgaaccgga ggagaaggca cagtccacct catcccccta ggccaagttc    3840
ccttgaggag ctgggttatg agtacatgga tgtggggtca gacctcagtg cctctctggg    3900
cagcacacag agttgcccac tccaccctgt acccatcatg cccactgcag gcacaactcc    3960
agatgaagac tatgaatata tgaatcggca acgagatgga ggtggtcctg ggggtgatta    4020
tgcagccatg ggggcctgcc cagcatctga gcaagggtat gaagagatga gagcttttca    4080
ggggcctgga catcaggccc cccatgtcca ttatgcccgc ctaaaaactc tacgtagctt    4140
agaggctaca gactctgcct ttgataaccc tgattactgg catagcaggc ttttccccaa    4200
ggctaatgcc cagagaacgt aactcctgct ccctgtggca ctcagggagc atttaatggc    4260
agctagtgcc tttagagggt accgtcttct ccctattccc tctctctccc aggtcccagc    4320
ccctttcccc cagtcccaga caattccatt caatctttgg aggcttttaa acattttgac    4380
acaaaattct tatggtatgt agccagctgt gcactttctt ctctttccca accccaggaa    4440
aggttttcct tattttgtgt gctttcccag tcccattcct cagcttcttc acaggcactc    4500
ctggagatat gaaggattac tctccatatc ccttcctctc aggctcttga ctacttggaa    4560
ctaggctctt atgtgtgcct tgtttcccca tcagactgtc aagaagagga aagggaggaa    4620
acctagcaga ggaaagtgta attttggttt atgactctta acccctaga aagacagaag    4680
cttaaaatct gtgaagaaag aggttaggag tagatattga ttactatcat aattcagcac    4740
ttaactatga gccaggcatc atactaaact tcacctacat tatctcactt agtccttat    4800
catccttaaa acaattctgt gacatacata ttatctcatt ttacacaaag ggaagtcggg    4860
catggtggct catgcctgta atctcagcac tttgggaggc tgaggcagaa ggattacctg    4920
aggcaaggag tttgagacca gcttagccaa catagtaaga ccccatctc tttaaaaaaa    4980
aaaaaaaaaa aaaaaaaaa actttagaac tgggtgcagt ggctcatgcc tgtaatccca    5040
gccagcactt tgggaggctg agatgggaag atcacttgag cccagaatta gagataagcc    5100
tatgaaaaca tagcaagaca ctgtctctac aggggaaaaa aaaaaagaa actgagcctt    5160
aaagagatga aataaattaa gcagtagatc caggatgcaa aatcctccca attcctgtgc    5220
atgtgctctt attgtaaggt gccaagaaaa actgatttaa gttacagccc ttgtttaagg    5280
ggcactgttt cttgtttttg cactgaatca agtctaaccc caacagccac atcctcctat    5340
acctagacat ctcatctcag gaagtggtgg tgggggtagt cagaaggaaa aataactgga    5400
catctttgtg taaaccataa tccacatgtg ccgtaaatga tcttcactcc ttatccgagg    5460
gcaaattcac aaggatcccc aagatccact tttagaagcc attctcatcc a             5511
```

<210> SEQ ID NO 198

```
<211> LENGTH: 5616
<212> TYPE: DNA
<213> ORGANISM: homo sapiens

<400> SEQUENCE: 198
ccccggcgca gcgcggccgc agcagcctcc gcccccgca cggtgtgagc gcccgacgcg      60
gccgaggcgg ccggagtccc gagctagccc cggcggccgc cgccgcccag accggacgac     120
aggccacctc gtcggcgtcc gcccgagtcc ccgcctcgcc gccaacgcca caaccaccgc     180
gcacggcccc ctgactccgt ccagtattga tcgggagagc cggagcgagc tcttcgggga     240
gcagcgatgc gaccctccgg gacggccggg gcagcgctcc tggcgctgct ggctgcgctc     300
tgcccggcga gtcgggctct ggaggaaaag aaagtttgcc aaggcacgag taacaagctc     360
acgcagttgg gcacttttga agatcatttt ctcagcctcc agaggatgtt caataactgt     420
gaggtggtcc ttgggaattt ggaaattacc tatgtgcaga ggaattatga tctttccttc     480
ttaaagacca tccaggaggt ggctggttat gtcctcattg ccctcaacac agtggagcga     540
attcctttgg aaaacctgca gatcatcaga ggaaatatgt actacgaaaa ttcctatgcc     600
ttagcagtct tatctaacta tgatgcaaat aaaaccggac tgaaggagct gcccatgaga     660
aatttacagg aaatcctgca tggcgccgtg cggttcagca caaccctgc cctgtgcaac     720
gtggagagca tccagtggcg ggacatagtc agcagtgact ttctcagcaa catgtcgatg     780
gacttccaga accacctggg cagctgccaa aagtgtgatc caagctgtcc aatgggagc     840
tgctggggtg caggagagga gaactgccag aaactgacca aaatcatctg tgcccagcag     900
tgctccgggc gctgccgtgg caagtccccc agtgactgct gccacaacca gtgtgctgca     960
ggctgcacag gccccgga gagcgactgc ctggtctgcc gcaaattccg agacgaagcc    1020
acgtgcaagg acacctgccc cccactcatg ctctacaacc ccaccacgta ccagatggat    1080
gtgaacccg agggcaaata cagctttggt gccacctgcg tgaagaagtg tccccgtaat    1140
tatgtggtga cagatcacgg ctcgtgcgtc cgagcctgtg gggccgacag ctatgagatg    1200
gaggaagacg gcgtccgcaa gtgtaagaag tgcgaagggc cttgccgcaa agtgtgtaac    1260
ggaataggta ttggtgaatt taaagactca ctctccataa atgctacgaa tattaaacac    1320
ttcaaaaact gcacctccat cagtggcgat ctccacatcc tgccggtggc atttagggt    1380
gactccttca cacatactcc tcctctggat ccacaggaac tggatattct gaaaaccgta    1440
aaggaaatca cagggttttt gctgattcag gcttggcctg aaaacaggac ggacctccat    1500
gcctttgaga acctagaaat catacgcggc aggaccaagc aacatggtca gttttctctt    1560
gcagtcgtca gcctgaacat aacatccttg ggattacgct ccctcaagga gataagtgat    1620
ggagatgtga taatttcagg aaacaaaaat ttgtgctatg caaatacaat aaactggaaa    1680
aaactgtttg ggacctccgg tcagaaaacc aaaattataa gcaacagagg tgaaaacagc    1740
tgcaaggcca caggccaggt ctgccatgcc ttgtgctccc ccgagggctg ctgggcccg    1800
gagcccaggg actgcgtctc ttgccggaat gtcagccgag caggaatg cgtggacaag    1860
tgcaaccttc tggagggtga gccaagggag tttgtggaga ctctgagtg catacagtgc    1920
cacccagagt gcctgcctca ggccatgaac atcacctgca caggacgggg accagacaac    1980
tgtatccagt gtgcccacta cattgacggc ccccactgcg tcaagacctg cccggcagga    2040
gtcatgggag aaaacaacac cctggtctgg aagtacgcag acgccggcca tgtgtgccac    2100
ctgtgccatc caaactgcac ctacggatgc actgggccag gtcttgaagg ctgtccaacg    2160
aatgggccta agatcccgtc catcgccact gggatggtgg gggccctcct cttgctgctg    2220
```

```
gtggtggccc tggggatcgg cctcttcatg cgaaggcgcc acatcgttcg gaagcgcacg    2280
ctgcggaggc tgctgcagga gagggagctt gtggagcctc ttacacccag tggagaagct    2340
cccaaccaag ctctcttgag gatcttgaag gaaactgaat tcaaaaagat caaagtgctg    2400
ggctccggtg cgttcggcac ggtgtataag ggactctgga tcccagaagg tgagaaagtt    2460
aaaattcccg tcgctatcaa ggaattaaga gaagcaacat ctccgaaagc caacaaggaa    2520
atcctcgatg aagcctacgt gatggccagc gtggacaacc ccacgtgtg ccgcctgctg     2580 ggcatctgcc tcacctccac cgtgcagctc atcacgcagc tcatgccctt cggctgcctc    2640
ctggactatg tccgggaaca caagacaat attggctccc agtacctgct caactggtgt     2700
gtgcagatcg caaagggcat gaactacttg gaggaccgtc gcttggtgca ccgcgacctg    2760
gcagccagga acgtactggt gaaaacaccg cagcatgtca agatcacaga ttttgggctg    2820
gccaaactgc tgggtgcgga agagaaagaa taccatgcag aaggaggcaa agtgcctatc    2880
aagtggatgg cattggaatc aattttacac agaatctata cccaccagag tgatgtctgg    2940
agctacgggg tgaccgtttg ggagttgatg acctttggat ccaagccata tgacggaatc    3000
cctgccagcg agatcctctc catcctggag aaaggagaac gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc agggggatga agaatgcat ttgccaagtc ctacagactc caacttctac     3240
cgtgccctga tggatgaaga agacatggac gacgtggtgg atgccgacga gtacctcatc    3300
ccacagcagg gcttcttcag cagcccctcc acgtcacgga ctccctcct gagctctctg     3360 agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcagag acccacacta ccaggacccc cacagcactg cagtgggcaa ccccgagtat    3660
ctcaacactg tccagcccac ctgtgtcaac agcacattcg acagccctgc ccactgggcc    3720
cagaaaggca gccaccaaat tagcctggac aaccctgact accagcagga cttctttccc    3780
aaggaagcca agcaaatgg catctttaag gctccacag ctgaaaatgc agaataccta      3840
agggtcgcgc cacaaagcag tgaatttatt ggagcatgac cacggaggat agtatgagcc    3900
ctaaaaatcc agactctttc gatacccagg accaagccac agcaggtcct ccatcccaac    3960
agccatgccc gcattagctc ttagacccac agactggttt tgcaacgttt acaccgacta    4020
gccaggaagt acttccacct cgggcacatt ttgggaagtt gcattccttt gtcttcaaac    4080
tgtgaagcat ttacagaaac gcatccagca agaatattgt cccttttgagc agaaatttat   4140 ctttcaaaga ggtatatttg aaaaaaaaaa aagtatatg tgaggatttt tattgattgg     4200
ggatcttgga gttttcatt gtcgctattg attttacttt caatgggctc ttccaacaag     4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
agaaacggag gggatggaat tcttccttag acttactttt gtaaaaatgt ccccacggta    4560
cttactcccc actgatggac cagtggtttc cagtcatgag cgttagactg acttgtttgt    4620
```

```
cttccattcc attgttttga aactcagtat gctgccsctg tcttgctgtc atgaaatcag      4680
caagagagga tgacacatca ataataact cggattccag cccacattgg attcatcagc      4740
atttggacca atagcccaca gctgagaatg tggaatacct aaggatagca ccgcttttgt      4800
tctcgcaaaa acgtatctcc taatttgagg ctcagatgaa atgcatcagg tcctttgggg      4860
catagatcag aagactacaa aaatgaagct gctctgaaat ctcctttagc catcacccca      4920 acccccaaa attagtttgt gttacttatg aagatagtt ttctccttt acttcacttc        4980 aaaagctttt tactcaaaga gtatatgttc cctccaggtc agctgccccc aaaccccctc     5040
cttacgcttt gtcacacaaa aagtgtctct gccttgagtc atctattcaa gcacttacag     5100
ctctggccac aacagggcat tttacaggtg cgaatgacag tagcattatg agtagtgtgg     5160
aattcaggta gtaaatatga aactagggtt tgaaattgat aatgctttca caacatttgc     5220
agatgtttta gaaggaaaaa agttccttcc taaaataatt tctctacaat tggaagattg     5280
gaagattcag ctagttagga gcccacccttt tttcctaatc tgtgtgtgcc ctgtaacctg    5340
actggttaac agcagtcctt tgtaaacagt gttttaaact ctcctagtca atatccaccc    5400
catccaattt atcaaggaag aaatggttca gaaatatttt tcagcctaca gttatgttca    5460
gtcacacaca catacaaaat gttccttttg cttttaaagt aattttttgac tcccagatca   5520 gtcagagccc ctacagcatt gttaagaaag tatttgattt ttgtctcaat gaaaataaaa    5580
ctatattcat ttccactcta aaaaaaaaaa aaaaaa                              5616
```

<210> SEQ ID NO 199
<211> LENGTH: 4624
<212> TYPE: DNA
<213> ORGANISM: homo sapiens

<400> SEQUENCE: 199

```
ggaggaggtg gaggaggagg gctgcttgag gaagtataag aatgaagttg tgaagctgag       60
attcccctcc attgggaccg gagaaaccag gggagccccc cgggcagccg cgcgcccctt      120
cccacggggc cctttactgc gccgcgcgcc cggcccccac ccctcgcagc acccgcgcc      180 ccgcgccctc ccagccgggt ccagccggag ccatgggggcc ggagccgcag tgagcaccat    240
ggagctggcg gccttgtgcc gctgggggct cctcctcgcc ctcttgcccc ccggagccgc     300
gagcacccaa gtgtgcaccg gcacagacat gaagctgcgg ctccctgcca gtcccgagac    360
ccacctggac atgctccgcc acctctacca gggctgccag gtggtgcagg gaaacctgga    420
actcacctac ctgccaccaa atgccagcct gtccttcctg caggatatcc aggaggtgca    480
gggctacgtg ctcatcgctc acaaccaagt gaggcaggtc ccactgcaga ggctgcggat    540
tgtgcgaggc acccagctct ttgaggacaa ctatgccctg gccgtgctag acaatggaga    600
cccgctgaac aataccaccc ctgtcacagg ggcctcccca ggaggcctgc gggagctgca    660
gcttcgaagc ctcacagaga tcttgaaagg aggggtcttg atccagcgga acccccagct    720
ctgctaccag gacacgattt tgtggaagga catcttccac aagaacaacc agctggctct   780
cacactgata gacaccaacc gctctcgggc ctgccacccc tgttctccga tgtgtaaggg    840
ctcccgctgc tggggagaga gttctgagga ttgtcagagc ctgacgcgca ctgtctgtgc    900
cggtggctgt gcccgctgca aggggccact gcccactgac tgctgccatg agcagtgtgc    960
tgccggctgc acgggcccca agcactctga ctgcctggcc tgcctccact caaccacag   1020 tggcatctgt gagctgcact gcccagccct ggtcacctac aacacagaca cgtttgagtc   1080
catgcccaat cccgagggcc ggtatacatt cggcgccagc tgtgtgactg cctgtcccta  1140
```

```
caactacctt tctacggacg tgggatcctg caccctcgtc tgcccctgc acaaccaaga    1200 ggtgacagca gaggatggaa cacagcggtg tgagaagtgc agcaagccct gtgcccgagt   1260
gtgctatggt ctgggcatgg agcacttgcg agaggtgagg gcagttacca gtgccaatat   1320
ccaggagttt gctggctgca agaagatctt tgggagcctg gcatttctgc cggagagctt   1380
tgatggggac ccagcctcca acactgcccc gctccagcca gagcagctcc aagtgtttga   1440
gactctggaa gagatcacag gttacctata catctcagca tggccggaca gcctgcctga   1500
cctcagcgtc ttccagaacc tgcaagtaat ccggggacga attctgcaca atggcgccta   1560
ctcgctgacc ctgcaaggc tgggcatcag ctggctgggg ctgcgctcac tgagggaact   1620
gggcagtgga ctggccctca tccaccataa cacccacctc tgcttcgtgc acacggtgcc   1680
ctgggaccag ctctttcgga acccgcacca agctctgctc cacactgcca accggccaga   1740
ggacgagtgt gtgggcgagg gcctggcctg ccaccagctg tgcgcccgag ggcactgctg   1800
gggtccaggg cccacccagt gtgtcaactg cagccagttc cttcggggcc aggagtgcgt   1860
ggaggaatgc cgagtactgc aggggctccc cagggagtat gtgaatgcca ggcactgttt   1920
gccgtgccac cctgagtgtc agccccagaa tggctcagtg acctgttttg accggaggc   1980 tgaccagtgt gtggcctgtg cccactataa ggaccctccc ttctgcgtgg cccgctgccc   2040
cagcggtgtg aaacctgacc tctcctacat gcccatctgg aagtttccag atgaggaggg   2100
cgcatgccag ccttgcccca tcaactgcac ccactcctgt gtggacctgg atgacaaggg   2160
ctgccccgcc gagcagagag ccagccctct gacgtccatc atctctgcgg tggttggcat   2220
tctgctggtc gtggtcttgg gggtggtctt tgggatcctc atcaagcgac ggcagcagaa   2280
gatccggaag tacacgatgc ggagactgct gcaggaaacg gagctggtgg agccgctgac   2340
acctagcgga gcgatgccca accaggcgca gatgcgggatc ctgaaagaga cggagctgag   2400
gaaggtgaag gtgcttggat ctggcgcttt tggcacagtc tacaagggca tctggatccc   2460
tgatggggag aatgtgaaaa ttccagtggc catcaaagtg ttgagggaaa acacatcccc   2520
caaagccaac aaagaaatct tagacgaagc atacgtgatg gctggtgtgg gctcccata    2580 tgtctcccgc cttctgggca tctgcctgac atccacggtg cagctggtga cacagcttat   2640
gccctatggc tgcctcttag accatgtccg ggaaaaccgc ggacgcctgg ctcccagga    2700 cctgctgaac tggtgtatgc agattgccaa ggggatgagc tacctggagg atgtgcggct   2760
cgtacacagg gacttggccg ctcggaacgt gctggtcaag agtcccaacc atgtcaaaat   2820
tacagacttc gggctggctc ggctgctgga cattgacgag acagagtacc atgcagatgg   2880
gggcaaggtg cccatcaagt ggatggcgct ggagtccatt ctccgccggc ggttcaccca   2940
ccagagtgat gtgtggagtt atggtgtgac tgtgtgggag ctgatgactt ttggggccaa   3000
accttacgat gggatcccag cccggagat ccctgacctg ctggaaaagg gggagcggct   3060
gccccagccc cccatctgca ccattgatgt ctacatgatc atggtcaaat gttgatgat   3120 tgactctgaa tgtcggccaa gattccggga gttggtgtct gaattctccc gcatggccag   3180 ggaccccag cgctttgtgg tcatccagaa tgaggacttg ggcccagcca gtcccttgga   3240
cagcaccttc taccgctcac tgctggagga cgatgacatg ggggacctgg tggatgctga   3300
ggagtatctg gtaccccagc agggcttctt ctgtccagac cctgcccgg cgctggggg    3360 catggtccac cacaggcacc gcagctcatc taccaggagt ggcggtgggg acctgacact   3420
agggctggag ccctctgaag aggaggcccc caggtctcca ctggcaccct ccgaaggggc   3480
tggctccgat gtatttgatg gtgacctggg aatgggggca gccaagggc tgcaaagcct   3540
```

```
cccacacat gaccccagcc ctctacagcg gtacagtgag gaccccacag taccctgcc    3600
ctctgagact gatggctacg ttgccccct gacctgcagc cccagcctg aatatgtgaa     3660
ccagccagat gttcggcccc agccccttc gccccgagag ggccctctgc ctgctgcccg    3720
acctgctggt gccactctgg aaaggcccaa gactctctcc caggaagga atggggtcgt    3780
caaagacgtt tttgcctttg ggggtgccgt ggagaacccc gagtacttga cacccaggg    3840
aggagctgcc cctcagcccc accctcctcc tgccttcagc ccagccttcg acaacctcta   3900
ttactgggac caggacccac cagagcgggg ggctccaccc agcaccttca aaggggacacc  3960
tacggcagag aacccagagt acctgggtct ggacgtgcca gtgtgaacca gaaggccaag   4020
tccgcagaag ccctgatgtg tcctcaggga gcagggaagg cctgacttct gctggcatca   4080
agaggtggga gggccctccg accacttcca ggggaacctg ccatgccagg aacctgtcct   4140
aaggaacctt ccttcctgct tgagttccca gatggctgga aggggtccag cctcgttgga   4200
agaggaacag cactggggag tctttgtgga ttctgaggcc ctgcccaatg agactctagg   4260
gtccagtgga tgccacagcc cagcttggcc ctttccttcc agatcctggg tactgaaagc   4320
cttagggaag ctggcctgag aggggaagcg gccctaaggg agtgtctaag aacaaaagcg   4380
acccattcag agactgtccc tgaaacctag tactgcccc catgaggaag gaacagcaat    4440
ggtgtcagta tccaggcttt gtacagagtg cttttctgtt tagtttttac ttttttttgtt 4500
ttgttttttt aaagatgaaa taaagaccca gggggagaat gggtgttgta tggggaggca  4560
agtgtggggg gtccttctcc acccacctt tgtccatttg caaatatatt ttggaaaaca   4620
gcta                                                               4624

<210> SEQ ID NO 200
<211> LENGTH: 24
<212> TYPE: DNA
<213> ORGANISM: Artificial
<220> FEATURE:
<223> OTHER INFORMATION: 24mers Sequence motif

<400> SEQUENCE: 200
catagctcca gacatcactc tggt                                         24

<210> SEQ ID NO 201
<211> LENGTH: 24
<212> TYPE: DNA
<213> ORGANISM: Artificial
<220> FEATURE:
<223> OTHER INFORMATION: 24mers Sequence motif

<400> SEQUENCE: 201
atagctccag acatcactct ggtg                                         24

<210> SEQ ID NO 202
<211> LENGTH: 24
<212> TYPE: DNA
<213> ORGANISM: Artificial
<220> FEATURE:
<223> OTHER INFORMATION: 24mers Sequence motif

<400> SEQUENCE: 202
gctccagaca tcactctggt gtgt                                         24

<210> SEQ ID NO 203
<211> LENGTH: 24
<212> TYPE: DNA
<213> ORGANISM: Artificial
<220> FEATURE:
```

```
<223> OTHER INFORMATION: 24mers Sequence motif

<400> SEQUENCE: 203
ctccagacat cactctggtg tgtg                                          24

<210> SEQ ID NO 204
<211> LENGTH: 24
<212> TYPE: DNA
<213> ORGANISM: Artificial
<220> FEATURE:
<223> OTHER INFORMATION: 24mers Sequence motif

<400> SEQUENCE: 204
caccatagct ccagacatca ctct                                          24

<210> SEQ ID NO 205
<211> LENGTH: 24
<212> TYPE: DNA
<213> ORGANISM: Artificial
<220> FEATURE:
<223> OTHER INFORMATION: 24mers Sequence motif

<400> SEQUENCE: 205
actgtcacac catagctcca gaca                                          24

<210> SEQ ID NO 206
<211> LENGTH: 24
<212> TYPE: DNA
<213> ORGANISM: Artificial
<220> FEATURE:
<223> OTHER INFORMATION: 24mers Sequence motif

<400> SEQUENCE: 206
caatcatcca cacttgacc atca                                           24

<210> SEQ ID NO 207
<211> LENGTH: 24
<212> TYPE: DNA
<213> ORGANISM: Artificial
<220> FEATURE:
<223> OTHER INFORMATION: 24mers Sequence motif

<400> SEQUENCE: 207
aatcatccaa cacttgacca tcac                                          24

<210> SEQ ID NO 208
<211> LENGTH: 24
<212> TYPE: DNA
<213> ORGANISM: Artificial
<220> FEATURE:
<223> OTHER INFORMATION: 24mers Sequence motif

<400> SEQUENCE: 208
tcatcaatca tccaacactt gacc                                          24

<210> SEQ ID NO 209
<211> LENGTH: 24
<212> TYPE: DNA
<213> ORGANISM: Artificial
<220> FEATURE:
<223> OTHER INFORMATION: 24mers Sequence motif

<400> SEQUENCE: 209
ctcatcaatc atccaacact tgac                                          24

<210> SEQ ID NO 210
```

```
<211> LENGTH: 24
<212> TYPE: DNA
<213> ORGANISM: Artificial
<220> FEATURE:
<223> OTHER INFORMATION: 24mers Sequence motif

<400> SEQUENCE: 210
tcaccatgta gacatcaatt gtgc                                         24

<210> SEQ ID NO 211
<211> LENGTH: 24
<212> TYPE: DNA
<213> ORGANISM: Artificial
<220> FEATURE:
<223> OTHER INFORMATION: 24mers Sequence motif

<400> SEQUENCE: 211
gacatagcct gtcacttctc gaat                                         24

<210> SEQ ID NO 212
<211> LENGTH: 24
<212> TYPE: DNA
<213> ORGANISM: Artificial
<220> FEATURE:
<223> OTHER INFORMATION: 24mers Sequence motif

<400> SEQUENCE: 212
acgaagatgg caaacttccc atcg                                         24

<210> SEQ ID NO 213
<211> LENGTH: 24
<212> TYPE: DNA
<213> ORGANISM: Artificial
<220> FEATURE:
<223> OTHER INFORMATION: 24mers Sequence motif

<400> SEQUENCE: 213
cccacaaggc tcacacatct tgag                                         24

<210> SEQ ID NO 214
<211> LENGTH: 24
<212> TYPE: DNA
<213> ORGANISM: Artificial
<220> FEATURE:
<223> OTHER INFORMATION: 24mers Sequence motif

<400> SEQUENCE: 214
cagaaagtcc aggttgccca ggat                                         24

<210> SEQ ID NO 215
<211> LENGTH: 24
<212> TYPE: DNA
<213> ORGANISM: Artificial
<220> FEATURE:
<223> OTHER INFORMATION: 24mers Sequence motif

<400> SEQUENCE: 215
gtgacattca agttcttcat gatc                                         24

<210> SEQ ID NO 216
<211> LENGTH: 24
<212> TYPE: DNA
<213> ORGANISM: Artificial
<220> FEATURE:
<223> OTHER INFORMATION: 24mers Sequence motif

<400> SEQUENCE: 216
```

```
ccagcactaa tttccttcag ggat                                              24

<210> SEQ ID NO 217
<211> LENGTH: 24
<212> TYPE: DNA
<213> ORGANISM: Artificial
<220> FEATURE:
<223> OTHER INFORMATION: 24mers Sequence motif

<400> SEQUENCE: 217
atacgcccag cactaatttc cttc                                              24

<210> SEQ ID NO 218
<211> LENGTH: 24
<212> TYPE: DNA
<213> ORGANISM: Artificial
<220> FEATURE:
<223> OTHER INFORMATION: 24mers Sequence motif

<400> SEQUENCE: 218
cacactttgc cctctgccac gcag                                              24

<210> SEQ ID NO 219
<211> LENGTH: 24
<212> TYPE: DNA
<213> ORGANISM: Artificial
<220> FEATURE:
<223> OTHER INFORMATION: 24mers Sequence motif

<400> SEQUENCE: 219
gggtcacaca ctttgccctc tgcc                                              24

<210> SEQ ID NO 220
<211> LENGTH: 24
<212> TYPE: DNA
<213> ORGANISM: Artificial
<220> FEATURE:
<223> OTHER INFORMATION: 24mers Sequence motif

<400> SEQUENCE: 220
tgcacagttc caaagacacc cgag                                              24

<210> SEQ ID NO 221
<211> LENGTH: 24
<212> TYPE: DNA
<213> ORGANISM: Artificial
<220> FEATURE:
<223> OTHER INFORMATION: 24mers Sequence motif

<400> SEQUENCE: 221
cccttggcaa tttgtactcc ccag                                              24

<210> SEQ ID NO 222
<211> LENGTH: 24
<212> TYPE: DNA
<213> ORGANISM: Artificial
<220> FEATURE:
<223> OTHER INFORMATION: 24mers Sequence motif

<400> SEQUENCE: 222
tctggtgtgt gtatttccca aagt                                              24

<210> SEQ ID NO 223
<211> LENGTH: 24
<212> TYPE: DNA
<213> ORGANISM: Artificial
<220> FEATURE:
```

<223> OTHER INFORMATION: 24mers Sequence motif

<400> SEQUENCE: 223
atgcccctct gatgactctg atgc                                              24

<210> SEQ ID NO 224
<211> LENGTH: 24
<212> TYPE: DNA
<213> ORGANISM: Artificial
<220> FEATURE:
<223> OTHER INFORMATION: 24mers Sequence motif

<400> SEQUENCE: 224
tattcatact cctcatcttc atct                                              24

<210> SEQ ID NO 225
<211> LENGTH: 24
<212> TYPE: DNA
<213> ORGANISM: Artificial
<220> FEATURE:
<223> OTHER INFORMATION: 24mers Sequence motif

<400> SEQUENCE: 225
tgatccacca caaagttatg ggga                                              24

<210> SEQ ID NO 226
<211> LENGTH: 24
<212> TYPE: DNA
<213> ORGANISM: Artificial
<220> FEATURE:
<223> OTHER INFORMATION: 24mers Sequence motif

<400> SEQUENCE: 226
cagacatcac tctggtgtgt gtat                                              24

<210> SEQ ID NO 227
<211> LENGTH: 24
<212> TYPE: DNA
<213> ORGANISM: Artificial
<220> FEATURE:
<223> OTHER INFORMATION: 24mers Sequence motif

<400> SEQUENCE: 227
tccagacatc actctggtgt gtgt                                              24

<210> SEQ ID NO 228
<211> LENGTH: 15
<212> TYPE: DNA
<213> ORGANISM: Artificial
<220> FEATURE:
<223> OTHER INFORMATION: Antisense oligonucleotides

<400> SEQUENCE: 228
tagcctgtca cttct                                                        15

<210> SEQ ID NO 229
<211> LENGTH: 15
<212> TYPE: DNA
<213> ORGANISM: Artificial
<220> FEATURE:
<223> OTHER INFORMATION: Antisense oligonucleotides

<400> SEQUENCE: 229
agcctgtcac ttctc                                                        15

<210> SEQ ID NO 230

```
<211> LENGTH: 14
<212> TYPE: DNA
<213> ORGANISM: Artificial
<220> FEATURE:
<223> OTHER INFORMATION: Antisense oligonucleotides

<400> SEQUENCE: 230
tagcctgtca cttc                                                         14

<210> SEQ ID NO 231
<211> LENGTH: 14
<212> TYPE: DNA
<213> ORGANISM: Artificial
<220> FEATURE:
<223> OTHER INFORMATION: Antisense oligonucleotides

<400> SEQUENCE: 231
agcctgtcac ttct                                                         14

<210> SEQ ID NO 232
<211> LENGTH: 13
<212> TYPE: DNA
<213> ORGANISM: Artificial
<220> FEATURE:
<223> OTHER INFORMATION: Antisense oligonucleotides

<400> SEQUENCE: 232
tagcctgtca ctt                                                          13

<210> SEQ ID NO 233
<211> LENGTH: 12
<212> TYPE: DNA
<213> ORGANISM: Artificial
<220> FEATURE:
<223> OTHER INFORMATION: Antisense oligonucleotides

<400> SEQUENCE: 233
tagcctgtca ct                                                           12

<210> SEQ ID NO 234
<211> LENGTH: 13
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(12)
<220> FEATURE:
<221> NAME/KEY: LNA nucleobases
<222> LOCATION: (1)..(2)
<220> FEATURE:
<221> NAME/KEY: LNA nucleobases
<222> LOCATION: (11)..(13)

<400> SEQUENCE: 234
tagcctgtca ctt                                                          13

<210> SEQ ID NO 235
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(3)
```

```
<220> FEATURE:
<221> NAME/KEY: LNA nucleobases
<222> LOCATION: (13)..(15)

<400> SEQUENCE: 235
cgtcagtatg cgaatc                                                  16

<210> SEQ ID NO 236
<211> LENGTH: 16
<212> TYPE: DNA
<213> ORGANISM: Artificial
<220> FEATURE:
<223> OTHER INFORMATION: LNA oligomers
<220> FEATURE:
<221> NAME/KEY: phosphorothiate linkage
<222> LOCATION: (1)..(15)
<220> FEATURE:
<221> NAME/KEY: LNA nucleobases
<222> LOCATION: (1)..(4)
<220> FEATURE:
<221> NAME/KEY: LNA nucleobases
<222> LOCATION: (13)..(15)

<400> SEQUENCE: 236
cgcagattag aaacct                                                  16

<210> SEQ ID NO 237
<211> LENGTH: 22
<212> TYPE: DNA
<213> ORGANISM: Artificial
<220> FEATURE:
<223> OTHER INFORMATION: probe sequence

<400> SEQUENCE: 237
ccacacctgg tcatagcggt ga                                           22

<210> SEQ ID NO 238
<211> LENGTH: 20
<212> TYPE: DNA
<213> ORGANISM: Artificial
<220> FEATURE:
<223> OTHER INFORMATION: probe sequence

<400> SEQUENCE: 238
ctgtttaggc caagcagagg                                              20

<210> SEQ ID NO 239
<211> LENGTH: 20
<212> TYPE: DNA
<213> ORGANISM: Artificial
<220> FEATURE:
<223> OTHER INFORMATION: probe sequence

<400> SEQUENCE: 239
attctgaatc ctgcgtccac                                              20

<210> SEQ ID NO 240
<211> LENGTH: 20
<212> TYPE: DNA
<213> ORGANISM: Artificial
<220> FEATURE:
<223> OTHER INFORMATION: probe sequence

<400> SEQUENCE: 240
cattgcccaa cctccgcgtg                                              20

<210> SEQ ID NO 241
<211> LENGTH: 20
```

```
<212> TYPE: DNA
<213> ORGANISM: Artificial
<220> FEATURE:
<223> OTHER INFORMATION: probe sequence

<400> SEQUENCE: 241
tgcagtggat tcgagaagtg                                         20

<210> SEQ ID NO 242
<211> LENGTH: 20
<212> TYPE: DNA
<213> ORGANISM: Artificial
<220> FEATURE:
<223> OTHER INFORMATION: probe sequence

<400> SEQUENCE: 242
ggcaaacttc ccatcgtaga                                         20

<210> SEQ ID NO 243
<211> LENGTH: 20
<212> TYPE: DNA
<213> ORGANISM: Artificial
<220> FEATURE:
<223> OTHER INFORMATION: probe sequence

<400> SEQUENCE: 243
actggcgctg ccaaggctgt                                         20

<210> SEQ ID NO 244
<211> LENGTH: 20
<212> TYPE: DNA
<213> ORGANISM: Artificial
<220> FEATURE:
<223> OTHER INFORMATION: probe sequence

<400> SEQUENCE: 244
ccacccagaa gactgtggat                                         20

<210> SEQ ID NO 245
<211> LENGTH: 20
<212> TYPE: DNA
<213> ORGANISM: Artificial
<220> FEATURE:
<223> OTHER INFORMATION: probe sequence

<400> SEQUENCE: 245
ttcagctcag ggatgacctt                                         20

<210> SEQ ID NO 246
<211> LENGTH: 20
<212> TYPE: DNA
<213> ORGANISM: Artificial
<220> FEATURE:
<223> OTHER INFORMATION: probe sequence

<400> SEQUENCE: 246
agctgtggcg tgatggccgt                                         20

<210> SEQ ID NO 247
<211> LENGTH: 20
<212> TYPE: DNA
<213> ORGANISM: Artificial
<220> FEATURE:
<223> OTHER INFORMATION: probe sequence

<400> SEQUENCE: 247
aactttggca ttgtggaagg                                         20
```

```
<210> SEQ ID NO 248
<211> LENGTH: 20
<212> TYPE: DNA
<213> ORGANISM: Artificial
<220> FEATURE:
<223> OTHER INFORMATION: probe sequence

<400> SEQUENCE: 248
ggatgcaggg atgatgttct                                          20
```

RNA ANTAGONIST COMPOUNDS FOR THE MODULATION OF HER3

CROSS REFERENCE TO RELATED APPLICATIONS

This application claims the benefit under 35 U.S.C. §119 (e) of U.S. Provisional Application Ser. No. 60/917,392, filed May 11, 2007, and U.S. Provisional Application Ser. No. 61/023,250, filed Jan. 24, 2008, the disclosures of which are incorporated herein by reference in their entireties.

FIELD OF THE INVENTION

The invention relates to oligomeric compounds (oligomers), which target HER3 mRNA in a cell, leading to reduced expression of HER3. Reduction of HER3 expression is beneficial for a range medical disorders, such as hyperproliferative diseases, including cancer. The invention provides therapeutic compositions comprising oligomers and methods for modulating the expression of HER3 using said oligomers, including methods of treatment.

BACKGROUND

HER3 belongs to the ErbB family of receptor tyrosine kinases, which includes four different receptors: ErbB-1 (EGFR, HER1), ErbB-2 (neu, HER2), ErbB-3 (HER3) and ErbB-4 (HER4) (Yarden et al, Nat. Rev. Mol. Cell. Biol, 2001, 2(2): 127-137). The receptor proteins of this family are composed of an extracellular ligand-binding domain, a hydrophobic transmembrane domain and a cytoplasmic tyrosine kinase-containing domain. Growth factors of the EGF family bind to most of the ErbB receptors and activate them. HER3 (ErbB3) is characterized by a lack of tyrosine kinase activity. EGFR, HER2 and recently HER3 have been associated with tumour formation. Recent studies, for example, have shown that EGFR is over expressed in a number of malignant human tissues when compared to their normal tissue counterparts. A high incidence of over expression, amplification, deletion and structural rearrangement of the gene coding for the EGFR has been found in biopsies of brain tumours. Amplification of the EGFR gene in glioblastoma multiforme tumours is one of the most consistent genetic alterations known. Elevated levels of HER3 mRNA have been detected in human mammary carcinomas. Recently, it has been shown that inhibition of Her2 and EGFR tyrosine kinase activity using tyrosine kinase inhibitors show limited effect on HER2-driven breast cancers due to a compensatory increase in HER3 expression and subsequent signalling through the PI3K/Akt pathway (Sergina et al., Nature, 2007, 445:437-441).

U.S. Pat. No. 6,277,640 to Bennett et al. discloses antisense compounds, compositions and methods for inhibiting the expression of HER3.

There is a need for agents capable of effectively inhibiting HER3 function.

SUMMARY OF INVENTION

The invention provides an oligomer of 10-50 monomers, such as 10-30 monomers, which comprises a first region of between 10-50 monomers, or 10-30 monomers, wherein the sequence of said first region is at least 80% identical to the reverse complement of a target region of a mammalian HER3 gene or mRNA, such as SEQ ID NO: 197, or a naturally occurring variant thereof.

The invention provides oligomer of 10-50 monomers which comprises a first region of 10-50 monomers, wherein the sequence of said first region is at least 80% identical to a sequence of an oligomer as shown in SEQ ID NOs:200-226 or 227.

The invention provides an oligomer of 10-50 monomers which comprises a first region of 10-50 monomers, wherein said the sequence of said first region is at least 80% identical to a sequence of an oligomer as shown in SEQ ID NOS:1-140, 228-232 or 233.

The invention further provides a conjugate comprising an oligomer according to the invention, which is covalently attached to one or more moieties that are not themselves nucleic acids or monomers ("conjugated moiety"). The conjugated moiety may comprise a sterol group such as cholesterol, or other chemical moiety that facilitates entry into the cell.

The invention provides for a conjugate comprising the oligomer according to the invention, which is covalently linked to a polymeric conjugated moiety containing positively charged groups, such as polyethylene glycol (PEG)—i.e. the oligomer according to the invention may, optionally, be pegylated.

The invention provides for a pharmaceutical composition comprising an oligomer of the invention or a conjugate thereof, and a pharmaceutically acceptable diluent, carrier, salt or adjuvant.

The invention provides for use of an oligomer of the invention or conjugate thereof as a medicament for the treatment of one or more of diseases, such as a hyperproliferative disease, such as cancer.

The invention further provides for an oligomer according to the invention for use in medicine.

The invention provides for the use of an oligomer of the invention or a conjugate thereof, for the preparation or manufacture of a medicament for the treatment of hyperproliferative diseases, such as cancer.

The invention provides for a method of treating hyperproliferative diseases such as cancer, said method comprising administering to a patient in need thereof an effective amount of an oligomer of the invention, or a conjugate or a pharmaceutical composition according to the invention.

The invention provides for a method of inhibiting (e.g., by down-regulating) the expression of HER3 in a cell which is expressing HER3, said method comprising administering an effective amount of an oligomer according to the invention, or a conjugate thereof, to said cell so as to effect the inhibition of HER3 expression in said cell.

Further provided are methods of inhibiting (e.g., by down-regulating) the expression of HER3, and/or EGFR and/or HER2, in cells or tissues comprising contacting said cells or tissues, in vitro or in vivo, with an effective amount of one or more oligomers of the invention, or conjugates or compositions thereof, to effect down-regulation of the expression of HER3 and/or EGFR and/or HER2.

Also disclosed are methods of treating a non-human animal or a human suspected of having, or being prone to, a disease or condition associated with expression, or over-expression, of HER3 (and/or EGFR and/or HER2), comprising administering to said non-human animal or human a therapeutically or prophylactically effective amount of one or more of oligomers of the invention, or conjugates or compositions thereof.

Methods of using one or more oligomers of the invention for the inhibition of expression of HER3 and/or EGFR and/or HER2, and for treating diseases associated with activity of HER3 (and/or EGFR and/or HER2) are also provided.

The invention provides for a method of triggering apoptosis in a cell or tissue, such as a cancer cell, said method comprising the step of contacting said cell or tissue with an effective amount of oligomer of the invention, or a conjugate, or a pharmaceutical composition thereof so that expression of HER3, and/or EGFR and/or HER2, is inhibited or reduced and apoptosis is triggered.

The invention further provides for an oligomer which comprises or consists of a first region, wherein the sequence of said first region is at least 80% identical to the sequence of a region of an oligomer having a sequence selected from the group consisting of SEQ ID NOs: 1-140, 200-232 and 233, such as a sequence selected from the group consisting of SEQ ID NOs: 200, 211, 54 and 1.

The invention further provides for an oligomer which comprises or consists of a first region, the sequence of said first region being identically present in an oligomer having a sequence selected from the group consisting of SEQ ID NO 169-196 and 234, such as SEQ ID NO: 169 or SEQ ID NO: 180.

The invention further provides for an oligomer which has a sequence selected from the group consisting of SEQ ID NOs: 169-196 and 234, such as the sequence of SEQ ID NO: 169 or 180, or which comprises or consists of a first region, the sequence of said first region being identically present in an oligomer selected from the group consisting of SEQ ID NOs: 169-196 and 234.

BRIEF DESCRIPTION OF THE FIGURES

FIG. 1. The HER3 target sequences that are targeted by the oligomers having the sequence of SEQ ID NOS: 1, 16, 17, 18, 19, 34, 49, 50, 51, 52, 53, 54, 55, 56, 57, 58, 59, 74, 75, 76, 91, 92, 107, 122, 137, 138, 139, and 140, respectively, are shown in bold and underlined, indicating their position in the HER3 transcript (GenBank Accession number NM_001982—SEQ ID NO:197).

DETAILED DESCRIPTION

Figure 2:
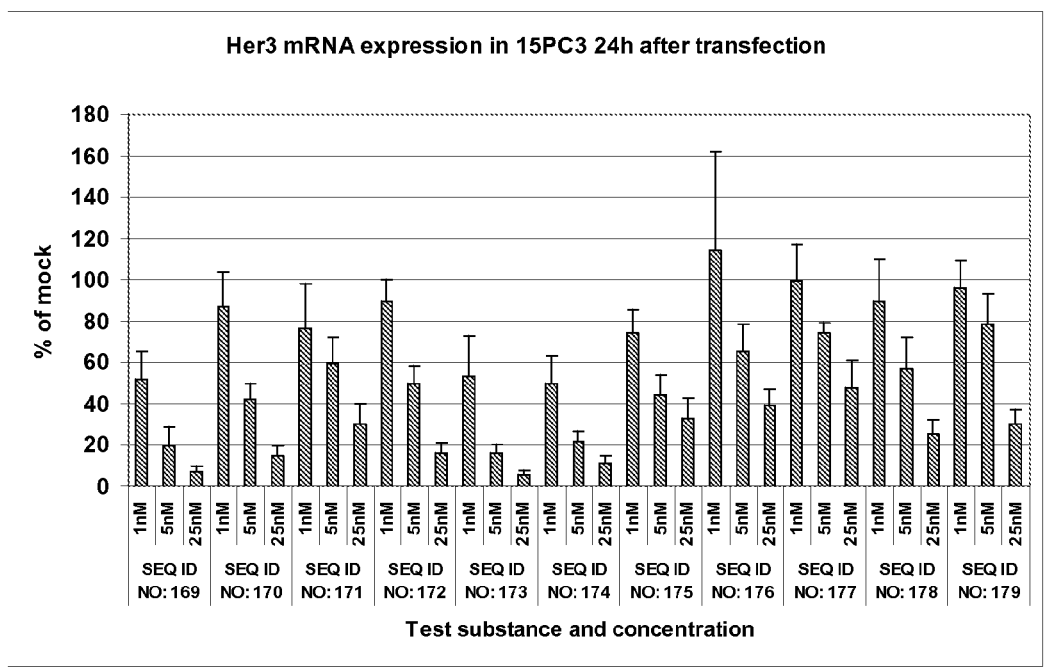
FIG. 2. HER3 mRNA expression in 15PC3, 24 hours after transfection, SEQ ID NOS:169-179
Figure 3:
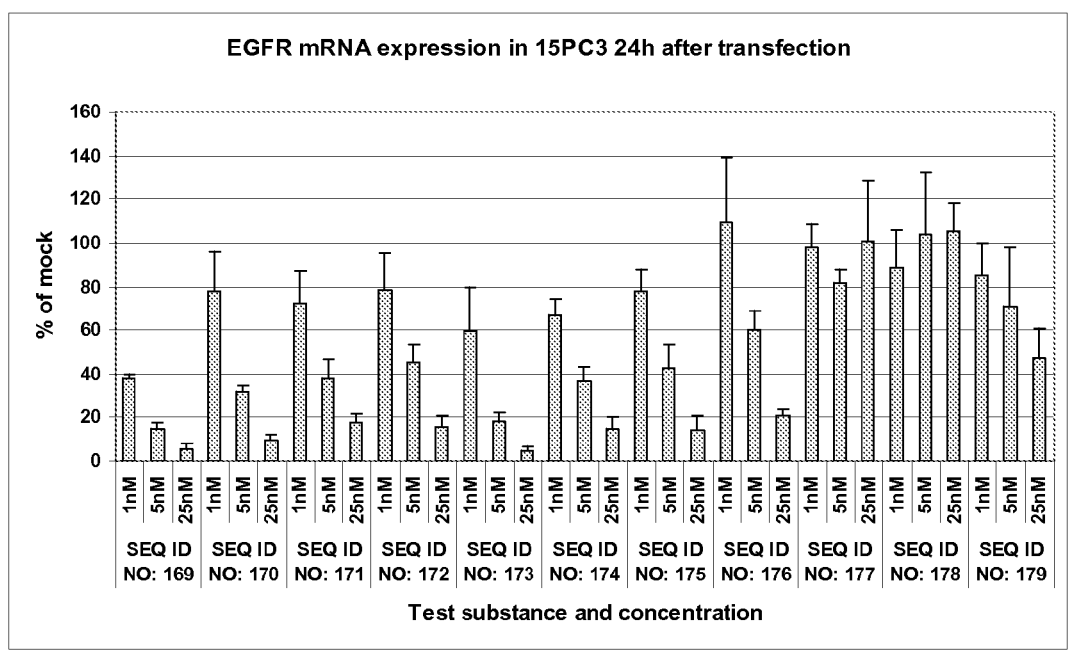
FIG. 3. EGFR mRNA expression in 15PC3, 24 hours after transfection, SEQ ID NOS:169-179
Figure 4:
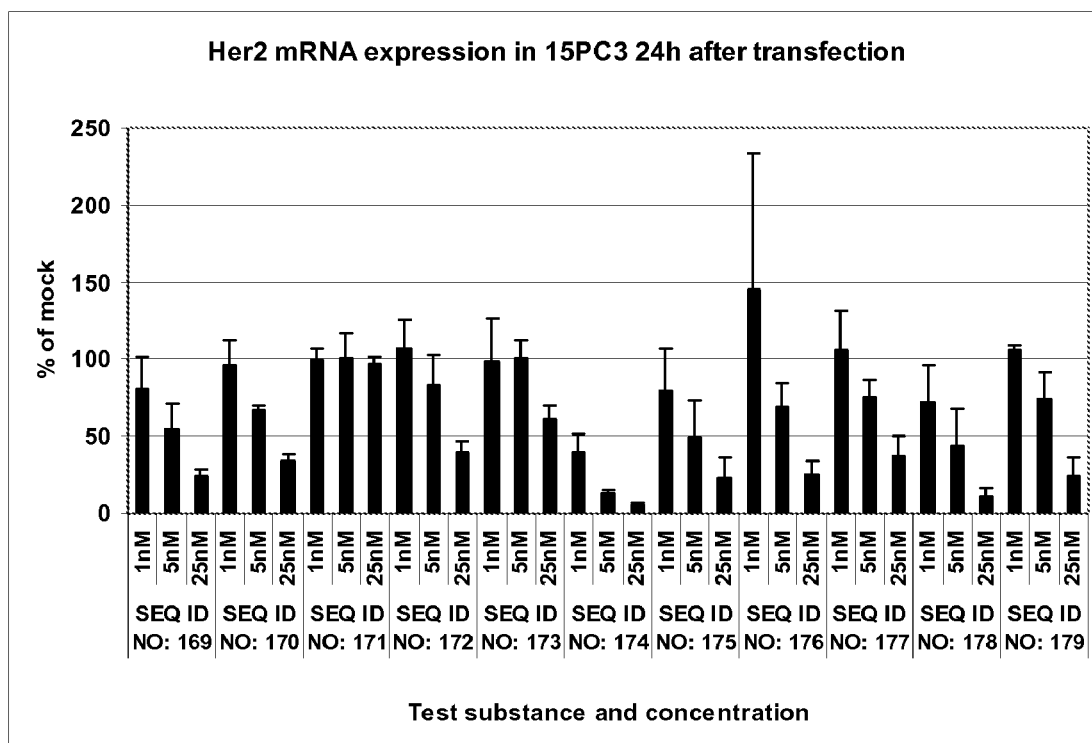
FIG. 4. HER-2 mRNA expression in 15PC3, 24 hours after transfection, SEQ ID NOS:169-179
Figure 5:
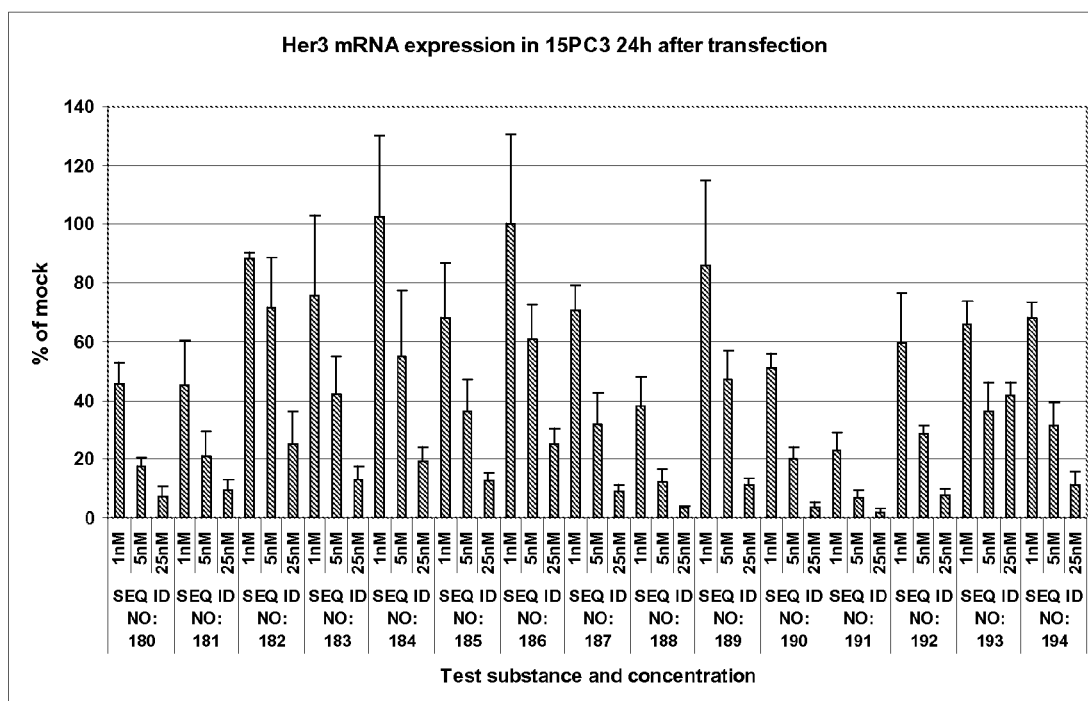
FIG. 5: HER3 mRNA expression in 15PC3, 24 hours after transfection, SEQ ID NOS:180-194

In some embodiments, the invention provides sequences, compositions and methods for modulating the expression of HER3 (and/or EGFR and/or HER2). In particular, this invention relates to target sequences in the HER3 gene, the sequence information of which in some embodiments is used to generate complementary antisense oligonucleotides capable of down-regulating the expression of HER3. In various embodiments, the invention further provides oligonucleotides (oligomers) which specifically hybridise under intracellular conditions to nucleic acids encoding HER3, and their uses to treat or prevent diseases associated with HER3 overexpression, e.g., cancer. In some embodiments, oligonucleotides of the invention down-regulate the expression of HER3. In other embodiments, oligonucleotides of the invention down-regulate the expression of HER3, HER2 and/or EGFR.

The term "HER3" is used herein interchangeably with the term "ErbB3".

The Oligomer

In a first aspect, oligomeric compounds (referred to herein as oligomers), are provided that are useful, e.g., in modulating the function of nucleic acid molecules encoding mammalian HER3, such as the HER3 nucleic acid shown in SEQ ID No: 197, and naturally occurring allelic variants of such nucleic acid molecules encoding mammalian HER3. The oligomers of the invention are composed of covalently linked monomers.

The term "monomer" includes both nucleosides and deoxynucleosides (collectively, "nucleosides") that occur naturally in nucleic acids and that do not contain either modified sugars or modified nucleobases, i.e., compounds in which a ribose sugar or deoxyribose sugar is covalently bonded to a naturally-occurring, unmodified nucleobase (base) moiety (i.e., the purine and pyrimidine heterocycles adenine, guanine, cytosine, thymine or uracil) and "nucleoside analogues," which are nucleosides that either do occur naturally in nucleic acids or do not occur naturally in nucleic acids, wherein either the sugar moiety is other than a ribose or a deoxyribose sugar (such as bicyclic sugars or 2' modified sugars, such as 2' substituted sugars), or the base moiety is modified (e.g., 5-methylcytosine), or both.

An "RNA monomer" is a nucleoside containing a ribose sugar and an unmodified nucleobase.

A "DNA monomer" is a nucleoside containing a deoxyribose sugar and an unmodified nucleobase.

A "Locked Nucleic Acid monomer," "locked monomer," or "LNA monomer" is a nucleoside analogue having a bicyclic sugar, as further described herein below.

The terms "corresponding nucleoside analogue" and "corresponding nucleoside" indicate that the base moiety in the nucleoside analogue and the base moiety in the nucleoside are identical. For example, when the "nucleoside" contains a 2-deoxyribose sugar linked to an adenine, the "corresponding nucleoside analogue" contains, for example, a modified sugar linked to an adenine base moiety.

The terms "oligomer," "oligomeric compound," and "oligonucleotide" are used interchangeably in the context of the invention, and refer to a molecule formed by covalent linkage of two or more contiguous monomers by, for example, a phosphate group (forming a phosphodiester linkage between nucleosides) or a phosphorothioate group (forming a phosphorothioate linkage between nucleosides). The oligomer consists of, or comprises, 10-50 monomers, such as 10-30 monomers.

In some embodiments, an oligomer comprises nucleosides, or nucleoside analogues, or mixtures thereof as referred to herein. An "LNA oligomer" or "LNA oligonucleotide" refers to an oligonucleotide containing one or more LNA monomers.

Nucleoside analogues that are optionally included within oligomers may function similarly to corresponding nucleosides, or may have specific improved functions. Oligomers wherein some or all of the monomers are nucleoside analogues are often preferred over native forms because of several desirable properties of such oligomers, such as the ability to penetrate a cell membrane, good resistance to extra- and/or intracellular nucleases and high affinity and specificity for the nucleic acid target. LNA monomers are particularly preferred, for example, for conferring several of the above-mentioned properties.

In various embodiments, one or more nucleoside analogues present within the oligomer are "silent" or "equivalent" in function to the corresponding natural nucleoside, i.e., have no functional effect on the way the oligomer functions to inhibit target gene expression. Such "equivalent" nucleoside analogues are nevertheless useful if, for example, they are easier or cheaper to manufacture, or are more stable under storage or manufacturing conditions, or can incorporate a tag or label. Typically, however, the analogues will have a functional effect on the way in which the oligomer functions to inhibit expression; for example, by producing increased binding affinity to the target region of the target nucleic acid and/or increased resistance to intracellular nucleases and/or increased ease of transport into the cell.

Thus, in various embodiments, oligomers according to the invention comprise nucleoside monomers and at least one nucleoside analogue monomer, such as an LNA monomer, or other nucleoside analogue monomers.

The term "at least one" comprises the integers larger than or equal to 1, such as 1, 2, 3, 4, 5, 6, 7, 8, 9, 10, 11, 12, 13, 14, 15, 16, 17, 18, 19, 20 and so forth. In various embodiments, such as when referring to the nucleic acid or protein targets of the compounds of the invention, the term "at least one" includes the terms "at least two" and "at least three" and "at least four." Likewise, in some embodiments, the term "at least two" comprises the terms "at least three" and "at least four."

In some embodiments, the oligomer consists of 10-50 contiguous monomers, such as 10, 11, 12, 13, 14, 15, 16, 17, 18, 19, 20, 21, 22, 23, 24, 25, 26, 27, 28, 29 or 30 contiguous monomers.

In some embodiments, the oligomer consists of 10-25 monomers, preferably, 10-16 monomers, and more preferably, 12-16 monomers.

In various embodiments, the oligomers comprise or consist of 10-25 contiguous monomers, 10-24 contiguous monomers, 12-25 or 12-24 or 10-22 contiguous monomers, such as 12-18 contiguous monomers, such as 13-17 or 12-16 contiguous monomers, such as 13, 14, 15, 16 contiguous monomers.

In various embodiments, the oligomers comprise or consist of 10-22 contiguous monomers, or 10-18, such as 12-18 or 13-17 or 12-16, such as 13, 14, 15 or 16 contiguous monomers.

In some embodiments, the oligomers comprise or consist of 10-16 or 12-16 or 12-14 contiguous monomers. In other embodiments, the oligomers comprise or consist of 14-18 or 14-16 contiguous monomers.

In various embodiments, the oligomers comprise or consist of 10, 11, 12, 13, or 14 contiguous monomers.

In various embodiments, the oligomer according to the invention consists of no more than 22 contiguous monomers, such as no more than 20 contiguous monomers, such as no more than 18 contiguous monomers, such as 15, 16 or 17 contiguous monomers. In certain embodiments, the oligomer of the invention comprises less than 20 contiguous monomers.

In various embodiments, the oligomer of the invention does not comprise RNA monomers.

It is preferred that the oligomers according to the invention are linear molecules or are linear as synthesized. The oligomer is, in such embodiments, a single stranded molecule, and typically does not comprise a short region of, for example, at least 3, 4 or 5 contiguous monomers, which are complementary to another region within the same oligomer such that the oligomer forms an internal duplex. In various embodiments, the oligomer is not substantially double-stranded, i.e., is not a siRNA.

In some embodiments, the oligomer of the invention consists of a contiguous stretch of monomers, the sequence of which is identified by a SEQ ID NO. disclosed herein (see, e.g., Tables 1-4). In other embodiments, the oligomer comprises a first region, the region consisting of a contiguous stretch of monomers, and one or more additional regions which consist of at least one additional monomer. In some embodiments, the sequence of the first region is identified by a SEQ ID NO. disclosed herein.

Gapmer Design

Typically, the oligomer of the invention is a gapmer.

A "gapmer" is an oligomer which comprises a contiguous stretch of monomers capable of recruiting an RNAse (e.g. RNAseH) as further described herein below, such as a region of at least 6 or 7 DNA monomers, referred to herein as region B, wherein region B is flanked both on its 5' and 3' ends by regions respectively referred to as regions A and C, each of regions A and C comprising or consisting of nucleoside analogues, such as affinity-enhancing nucleoside analogues, such as 1-6 nucleoside analogues.

Typically, the gapmer comprises regions, from 5' to 3', A-B-C, or optionally A-B-C-D or D-A-B-C, wherein: region A consists of or comprises at least one nucleoside analogue, such as at least one LNA monomer, such as 1-6 nucleoside analogues, such as LNA monomers; and region B consists of or comprises at least five contiguous monomers which are capable of recruiting RNAse (when formed in a duplex with a complementary target region of the target RNA molecule, such as the mRNA target), such as DNA monomers; and region C consists of or comprises at least one nucleoside analogue, such as at least one LNA monomer, such as 1-6 nucleoside analogues, such as LNA monomers, and; region D, when present, consists of or comprises 1, 2 or 3 monomers, such as DNA monomers.

In various embodiments, region A consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers; and/or region C consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers.

In certain embodiments, region B consists of or comprises 5, 6, 7, 8, 9, 10, 11 or 12 contiguous monomers which are capable of recruiting RNAse, or 6-10, or 7-9, such as 8 contiguous monomers which are capable of recruiting RNAse. In certain embodiments, region B consists of or comprises at least one DNA monomer, such as 1-12 DNA monomers, preferably 4-12 DNA monomers, more preferably 6-10 DNA monomers, such as 7-10 DNA monomers, most preferably 8, 9 or 10 DNA monomers.

In certain embodiments, region A consists of 3 or 4 nucleoside analogues, such as LNA monomers, region B consists of 7, 8, 9 or 10 DNA monomers, and region C consists of 3 or 4 nucleoside analogues, such as LNA monomers. Such designs include (A-B-C) 3-10-3, 3-10-4, 4-10-3, 3-9-3, 3-9-4, 4-9-3, 3-8-3, 3-8-4, 4-8-3, 3-7-3, 3-7-4, 4-7-3, and may further include region D, which may have one or 2 monomers, such as DNA monomers.

Further gapmer designs are disclosed in WO 2004/046160, which is hereby incorporated by reference.

U.S. provisional application, 60/977,409, hereby incorporated by reference, refers to "shortmer" gapmer oligomers. In some embodiments, oligomers presented here may be such shortmer gapmers.

In certain embodiments, the oligomer consists of 10, 11, 12, 13 or 14 contiguous monomers, wherein the regions of the oligomer have the pattern (5'-3'), A-B-C, or optionally A-B-C-D or D-A-B-C, wherein; region A consists of 1, 2 or 3 nucleoside analogue monomers, such as LNA monomers; region B consists of 7, 8 or 9 contiguous monomers which are capable of recruiting RNAse when formed in a duplex with a complementary RNA molecule (such as a mRNA target); and region C consists of 1, 2 or 3 nucleoside analogue monomers, such as LNA monomers. When present, region D consists of a single DNA monomer.

In certain embodiments, region A consists of 1 LNA monomer. In certain embodiments, region A consists of 2 LNA monomers. In certain embodiments, region A consists of 3 LNA monomers. In certain embodiments, region C consists of 1 LNA monomer. In certain embodiments, region C consists of 2 LNA monomers. In certain embodiments, region C consists of 3 LNA monomers. In certain embodiments, region B consists of 7 nucleoside monomers. In certain embodiments, region B consists of 8 nucleoside monomers. In certain embodiments, region B consists of 9 nucleoside monomers. In certain embodiments, region B comprises 1-9 DNA monomers, such as 2, 3, 4, 5, 6, 7 or 8 DNA monomers. In certain embodiments, region B consists of DNA monomers. In certain embodiments, region B comprises at least one LNA monomer which is in the alpha-L configuration, such as 2, 3, 4, 5, 6, 7, 8 or 9 LNA monomers in the alpha-L-configuration. In certain embodiments, region B comprises at least one alpha-L-oxy LNA monomer. In certain embodiments, all the LNA monomers in region B that are in the alpha-L-configuration are alpha-L-oxy LNA monomers. In certain embodiments, the number of monomers present in the A-B-C regions of the oligomers is selected from the group consisting of (nucleotide analogue monomers—region B—nucleoside analogue monomers): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, and 3-10-1. In certain embodiments, the number of monomers present in the A-B-C regions of the oligomers of the invention is selected from the group consisting of: 2-7-1, 1-7-2, 2-7-2, 3-7-3, 2-7-3, 3-7-2, 3-7-4, and 4-7-3. In certain embodiments, each of regions A and C consists of two LNA monomers, and region B consists of 8 or 9 nucleoside monomers, preferably DNA monomers.

In various embodiments, other gapmer designs include those where regions A and/or C consists of 3, 4, 5 or 6 nucleoside analogues, such as monomers containing a 2'-O-methoxyethyl-ribose sugar (2'MOE) or monomers containing a 2'-fluoro-deoxyribose sugar, and region B consists of 8, 9, 10, 11 or 12 nucleosides, such as DNA monomers, where regions A-B-C have 5-10-5 or 4-12-4 monomers. Further gapmer designs are disclosed in WO 2007/146511A2, hereby incorporated by reference.

Linkage Groups

The monomers of the oligomers described herein are coupled together via linkage groups. Suitably, each monomer is linked to the 3' adjacent monomer via a linkage group.

The terms "linkage group" or "internucleoside linkage" mean a group capable of covalently coupling together two contiguous monomers. Specific and preferred examples include phosphate groups (forming a phosphodiester between adjacent nucleoside monomers) and phosphorothioate groups (forming a phosphorothioate linkage between adjacent nucleoside monomers).

Suitable linkage groups include those listed in WO 2007/031091, for example the linkage groups listed on the first paragraph of page 34 of WO 2007/031091 (hereby incorporated by reference).

It is, in various embodiments, preferred to modify the linkage group from its normal phosphodiester to one that is more resistant to nuclease attack, such as phosphorothioate or boranophosphate—these two, being cleavable by RNase H, permitting RNase-mediated antisense inhibition of expression of the target gene.

In some embodiments, suitable sulphur (S) containing linkage groups as provided herein are preferred. In various embodiments, phosphorothioate linkage groups are preferred, particularly for the gap region (B) of gapmers. In certain embodiments, phosphorothioate linkages are used to link together monomers in the flanking regions (A and C). In various embodiments, phosphorothioate linkages are used for linking regions A or C to region D, and for linking together monomers within region D.

In various embodiments, regions A, B and C comprise linkage groups other than phosphorothioate, such as phosphodiester linkages, particularly, for instance when the use of nucleoside analogues protects the linkage groups within regions A and C from endo-nuclease degradation—such as when regions A and C comprise LNA monomers.

In various embodiments, adjacent monomers of the oligomer are linked to each other by means of phosphorothioate groups.

It is recognised that the inclusion of phosphodiester linkages, such as one or two linkages, into an oligomer with a phosphorothioate backbone, particularly with phosphorothioate linkage groups between or adjacent to nucleoside analogue monomers (typically in region A and/or C), can modify the bioavailability and/or bio-distribution of an oligomer—see WO 2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleoside linkage groups are phosphorothioate.

When referring to specific gapmer oligonucleotide sequences, such as those provided herein, it will be understood that, in various embodiments, when the linkages are phosphorothioate linkages, alternative linkages, such as those disclosed herein, may be used, for example phosphate (phosphodiester) linkages may be used, particularly for linkages between nucleoside analogues, such as LNA monomers.

Target Nucleic Acid

The terms "nucleic acid" and "polynucleotide" are used interchangeably herein, and are defined as a molecule formed by covalent linkage of two or more monomers, as above-described. Including 2 or more monomers, "nucleic acids" may be of any length, and the term is generic to "oligomers", which have the lengths described herein. The terms "nucleic acid" and "polynucleotide" include single-stranded, double-stranded, partially double-stranded, and circular molecules.

In various embodiments, the term "target nucleic acid", as used herein, refers to the nucleic acid (such as DNA or RNA) encoding mammalian HER3 polypeptide (e.g., such as human HER3 mRNA having the sequence in SEQ ID NO 197, or mammalian mRNAs having GenBank Accession numbers NM_001005915, NM_001982 and alternatively-spliced forms NP_001973.2 and NP_001005915.1 (human); NM_017218 (rat); NM_010153 (mouse); NM_001103105 (cow); or predicted mRNA sequences having GenBank Accession numbers XM_001491896 (horse), XM_001169469 and XM_509131 (chimpanzee)).

In various embodiments, "target nucleic acid" also includes a nucleic acid encoding a mammalian HER2 polypeptide (e.g., such mammalian mRNAs having GenBank Accession numbers NM_001005862 and NM_004448 (human); NM_017003 and NM_017218 (rat); NM_001003817 (mouse); NM_001003217 (dog); and NM_001048163 (cat)).

In various embodiments, "target nucleic acid" also includes a nucleic acid encoding a mammalian EGFR polypeptide (e.g., such as mammalian mRNAs having GenBank Accession numbers NM_201284, NM_201283, NM_201282 and NM_005228 (human); NM_007912 and NM_207655 (mouse); NM_031507 (rat); and NM_214007 (pig)).

It is recognized that the above-disclosed GenBank Accession numbers refer to cDNA sequences and not to mRNA sequences per se. The sequence of a mature mRNA can be derived directly from the corresponding cDNA sequence, with thymine bases (T) being replaced by uracil bases (U).

In various embodiments, "target nucleic acid" also includes HER3 (or HER2 or EGFR) encoding nucleic acids or naturally occurring variants thereof, and RNA nucleic acids derived therefrom, preferably mRNA, such as pre-mRNA, although preferably mature mRNA. In various embodiments, for example when used in research or diagnostics the "target nucleic acid" is a cDNA or a synthetic oligonucleotide derived from the above DNA or RNA target nucleic acids. The oligomers according to the invention are typically capable of hybridising to the target nucleic acid.

The term "naturally occurring variant thereof" refers to variants of the HER3 (or HER2 or EGFR) polypeptide or nucleic acid sequence which exist naturally within the defined taxonomic group, such as mammalian, such as mouse, monkey, and preferably human. Typically, when referring to "naturally occurring variants" of a polynucleotide the term also may encompass any allelic variant of the HER3 (or HER2 or EGFR) encoding genomic DNA which is found at the Chromosome Chr 12: 54.76-54.78 Mb by chromosomal translocation or duplication, and the RNA, such as mRNA derived therefrom. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

In certain embodiments, oligomers described herein bind to a region of the target nucleic acid (the "target region") by either Watson-Crick base pairing, Hoogsteen hydrogen bonding, or reversed Hoogsteen hydrogen bonding, between the monomers of the oligomer and monomers of the target nucleic acid. Such binding is also referred to as "hybridisation." Unless otherwise indicated, binding is by Watson-Crick pairing of complementary bases (i.e., adenine with thymine (DNA) or uracil (RNA), and guanine with cytosine), and the oligomer binds to the target region because the sequence of the oligomer is identical to, or partially-identical to, the sequence of the reverse complement of the target region; for purposes herein, the oligomer is said to be "complementary" or "partially complementary" to the target region, and the percentage of "complementarity" of the oligomer sequence to that of the target region is the percentage "identity" to the reverse complement of the sequence of the target region.

Unless otherwise made clear by context, the "target region" herein will be the region of the target nucleic acid having the sequence that best aligns with the reverse complement of the sequence of the specified oligomer (or region thereof), using the alignment program and parameters described herein below.

In determining the degree of "complementarity" between oligomers of the invention (or regions thereof) and the target region of the nucleic acid which encodes mammalian HER3 (or HER2 or EGFR), such as those disclosed herein, the degree of "complementarity" (also, "homology") is expressed as the percentage identity between the sequence of the oligomer (or region thereof) and the reverse complement of the sequence of the target region that best aligns therewith. The percentage is calculated by counting the number of aligned bases that are identical as between the 2 sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the invention and the target region.

Amino acid and polynucleotide alignments, percentage sequence identity, and degree of complementarity may be determined for purposes of the invention using the ClustalW algorithm using standard settings: see http://www.ebi.ac.uk/emboss/align/index.html, Method: EMBOSS::water (local): Gap Open=10.0, Gap extend=0.5, using Blosum 62 (protein), or DNAfull for nucleotide/nucleobase sequences.

As will be understood, depending on context, "mismatch" refers to a nonidentity in sequence (as, for example, between the nucleobase sequence of an oligomer and the reverse complement of the target region to which it binds; as for example, between the base sequence of two aligned HER3 encoding nucleic acids), or to noncomplementarity in sequence (as, for example, between an oligomer and the target region to which binds).

Suitably, the oligomer (or conjugate, as further described, below) is capable of inhibiting (such as, by down-regulating) expression of the HER3 (or HER2 or EGFR) gene.

In various embodiments, the oligomers of the invention effect inhibition of HER3 (or HER2 or EGFR) mRNA expression of at least 10% as compared to the normal expression level, at least 20%, more preferably at least 30%, 40%, 50%, 60%, 70%, 80%, 90% or 95% as compared to the normal expression level. In various embodiments, the oligomers of the invention effect inhibition of HER3 (or HER2 or EGFR) protein expression of at least 10% as compared to the normal expression level, at least 20%, more preferably at least 30%, 40%, 50%, 60%, 70%, 80%, 90% or 95% as compared to the normal expression level. In some embodiments, such inhibition is seen when using 1 nM of the oligomer or conjugate of the invention. In various embodiments, such inhibition is seen when using 25 nM of the oligomer or conjugate.

In various embodiments, the inhibition of mRNA expression is less than 100% (i.e., less than complete inhibition of expression), such as less than 98%, inhibition, less than 95% inhibition, less than 90% inhibition, less than 80% inhibition, such as less than 70% inhibition. In various embodiments, the inhibition of protein expression is less than 100% (i.e., less than complete inhibition of expression), such as less than 98%, inhibition, less than 95% inhibition, less than 90% inhibition, less than 80% inhibition, such as less than 70% inhibition.

Alternatively, modulation of expression levels can be determined by measuring levels of mRNA, e.g. by northern blotting or quantitative RT-PCR. When measuring via mRNA levels, the level of inhibition when using an appropriate dosage, such as 1 and 25 nM, is, in various embodiments, typically to a level of 10-20% of the normal levels in the absence of the compound of the invention.

Modulation (i.e., inhibition or increase) of expression level may also be determined by measuring protein levels, e.g. by methods such as SDS-PAGE followed by western blotting using suitable antibodies raised against the target protein.

In some embodiments, the invention provides oligomers that inhibit (e.g., down-regulate) the expression of one or more alternatively-spliced isoforms of HER3 mRNA and/or proteins derived therefrom. In some embodiments, the invention provides oligomers that inhibit expression of one or more of the alternatively-spliced protein isoforms of HER3 (GenBank Accession nos. NP_001973.2 and NP_001005915.1) and/or expression of the nucleic acids that encode the HER3 protein isoforms (GenBank Accession nos. NM_001982 and NM_001005915.1). In some embodiments, the mRNA encoding HER3 isoform 1 is the target nucleic acid. In other embodiments, the mRNA encoding HER3 isoform 2 is the target nucleic acid. In certain embodiments, the nucleic acids encoding HER3 isoform 1 and HER3 isoform 2 are target nucleic acids, for example, the oligomer having the sequence of SEQ ID NO: 180.

In various embodiments, the invention provides oligomers, or a first region thereof, having a base sequence that is complementary to the sequence of a target region in a HER3 nucleic acid, which oligomers down-regulate HER3 mRNA and/or HER3 protein expression and down-regulate the expression of mRNA and/or protein of one or more other ErbB receptor tyrosine kinase family members, such as HER2 and/or EGFR. Oligomers, or a first region thereof, that effectively bind to the target regions of two different ErbB receptor family nucleic acids (e.g., HER2 and HER3 mRNA) and that down-regulating the mRNA and/or protein expression of both targets are termed "bispecific." Oligomers, or a first region thereof, that bind to the target regions of three different ErbB receptor family members and are capable of effectively down-regulating all three genes are termed "trispecific". In various embodiments, an antisense oligonucleotide of the invention may be polyspecific, i.e. capable of binding to target regions of target nucleic acids of multiple members of the ErbB family of receptor tyrosine kinases and down-regulating their expression. As used herein, the terms "bispecific" and "trispecific" are understood not to be limiting in any way. For example, a "bispecific oligomer" may have some effect on a third target nucleic acid, while a "trispecific oligomer" may have a very weak and therefore insignificant effect on one of its three target nucleic acids.

In various embodiments, bispecific oligomers, or a first region thereof, are capable of binding to a target region in a HER3 nucleic acid and a target region in a HER2 target nucleic acid and effectively down-regulating the expression of HER3 and HER2 mRNA and/or protein. In certain embodiments, the bispecific oligomers do not down-regulate expression of HER3 mRNA and/or protein and HER2 mRNA and/or protein to the same extent. In other preferred embodiments, the bispecific oligomers of the invention, or a first region thereof, are capable of binding to a target region in a HER3 target nucleic acid and a target region in an EGFR target nucleic acid and effectively down-regulating the expression of HER3 mRNA and/or protein and EGFR mRNA and/or protein. In various embodiments, the bispecific oligomers do not down-regulate expression of HER3 mRNA and/or protein and EGFR mRNA and/or protein to the same extent. In still other embodiments, trispecific oligomers, or a first region thereof, are capable of binding to a target region in a HER3 target nucleic acid, and to target regions in two other ErbB family of receptor tyrosine kinase target nucleic acids and effectively down-regulating the expression of HER3 mRNA and/or protein and mRNA and/or protein of the two other members of the ErbB family of receptor tyrosine kinases. In various preferred embodiments, the trispecific oligomers, or a first region thereof, are capable of effectively down-regulating the expression of HER3 mRNA and/or protein, the expression of HER2 mRNA and/or protein, and the expression of EGFR mRNA and/or protein. In various embodiments, the trispecific oligomers do not down-regulate expression of HER3 mRNA and/or protein, HER2 mRNA and/or protein and EGFR mRNA and/or protein to the same extent.

In various embodiments, the invention therefore provides a method of inhibiting (e.g., by down-regulating) the expression of HER3 protein and/or mRNA in a cell which is expressing HER3 protein and/or mRNA, the method comprising contacting the cell with an amount of an oligomer or conjugate according to the invention effective to inhibit (e.g., to down-regulate) the expression of HER3 protein and/or mRNA in said cell. Suitably the cell is a mammalian cell, such as a human cell. The contacting may occur, in certain embodiments, in vitro. In other embodiments, the contacting may be effected in vivo, by administering the compound or conjugate of the invention to a mammal. In various embodiments, the invention provides a method of inhibiting (e.g., by down-regulating) the expression of HER3 protein and/or mRNA and the expression of HER2 protein and/or mRNA in a cell. The sequence of the human HER2 mRNA is shown in SEQ ID NO: 199. In still further embodiments, the invention provides a method of inhibiting (e.g., by down-regulating) the expression of HER3 protein and/or mRNA and the expression of EGFR protein and/or mRNA in a cell. The sequence of the human EGFR mRNA is shown in SEQ ID NO: 198. In yet further embodiments, the invention provides a method of inhibiting (e.g., by down-regulating) the expression of HER3, HER2 and EGFR mRNA and/or protein in a cell.

An oligomer of the invention typically binds to a target region of the human HER3 and/or the human HER2 and/or the human EGFR mRNA, and as such, comprises or consists of a region having a base sequence that is complementary or partially complementary to the base sequence of, e.g., SEQ ID NO 197, SEQ ID NO: 198 and/or SEQ ID NO: 199. In certain embodiments, the sequence of the oligomers of the invention may optionally comprise 1, 2, 3, 4 or more base mismatches when compared to the sequence of the best-aligned target region of SEQ ID NOs: 197, 198 or 199.

In some embodiments, the oligomers of the invention have sequences that are identical to a sequence selected from the group consisting of SEQ ID NOs: 200-227, 1-140 and 228-233 (see Table 1 herein below). In other embodiments, the oligomers of the invention have sequences that differ in one, two, or three bases when compared to a sequence selected from the group consisting of SEQ ID NOs: 200-227, 1-140 and 228-233. In some embodiments, the oligomers consist of or comprise 10-16 contiguous monomers. Examples of the sequences of oligomers consisting of 16 contiguous monomers are SEQ ID NOs: 1, 16, 17, 18, 19, 34, 49, 50, 51, 52, 53, 54, 55, 56, 57, 58, 59, 74, 75, 76, 91, 92, 107, 122, 137, 138, 139, and 140. Shorter sequences can be derived therefrom, e.g., the sequence of the shorter oligomer may be identically present in a region of an oligomer selected from those having base sequences of SEQ ID NOs: 200-227, 1-140 and 228-233. Longer oligomers may include a region having a sequence of at least 10 contiguous monomers that is identically present in SEQ ID NOs: 200-227, 1-140 and 228-233.

Figure 1A:
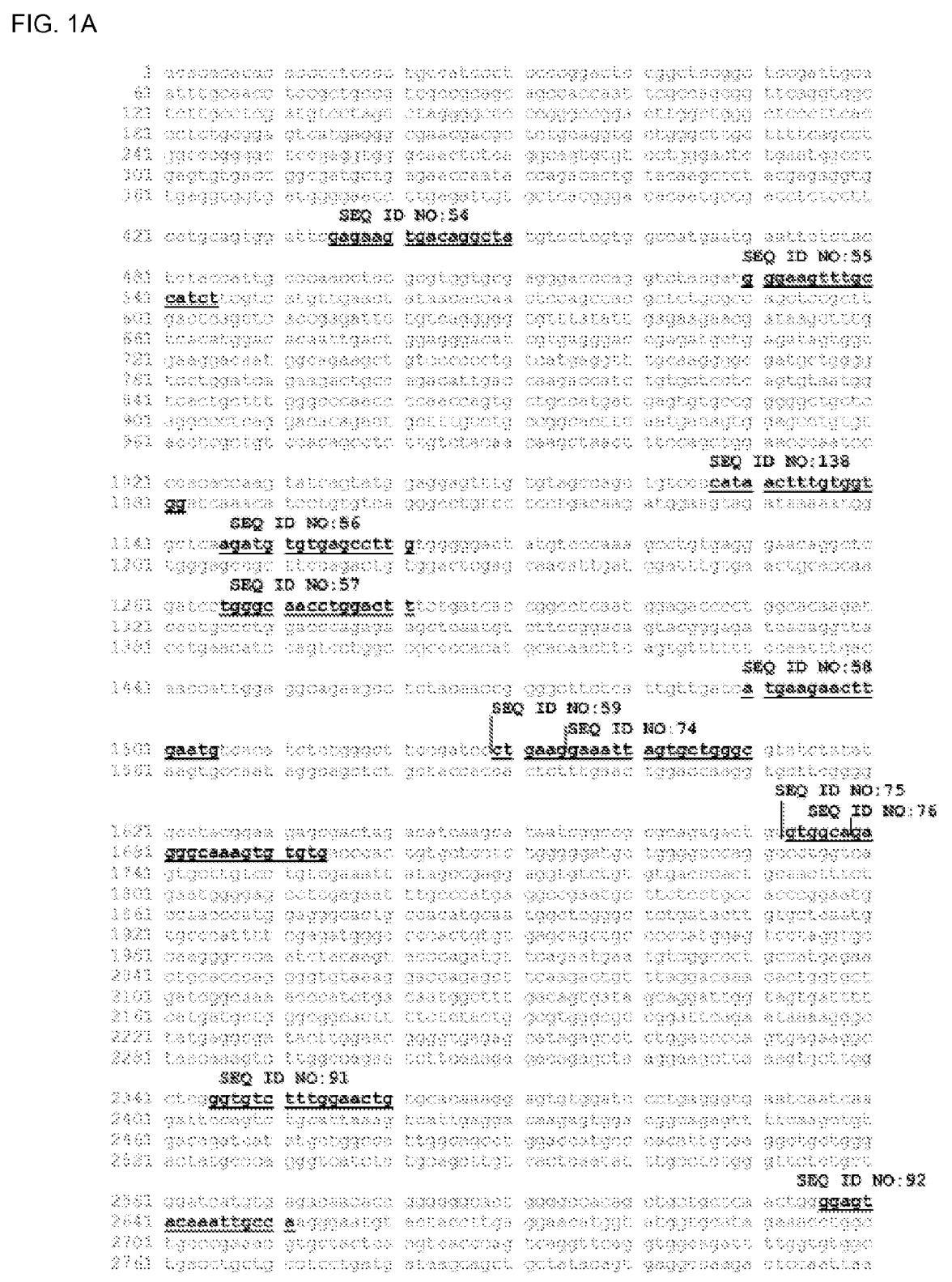
Figure 1B:
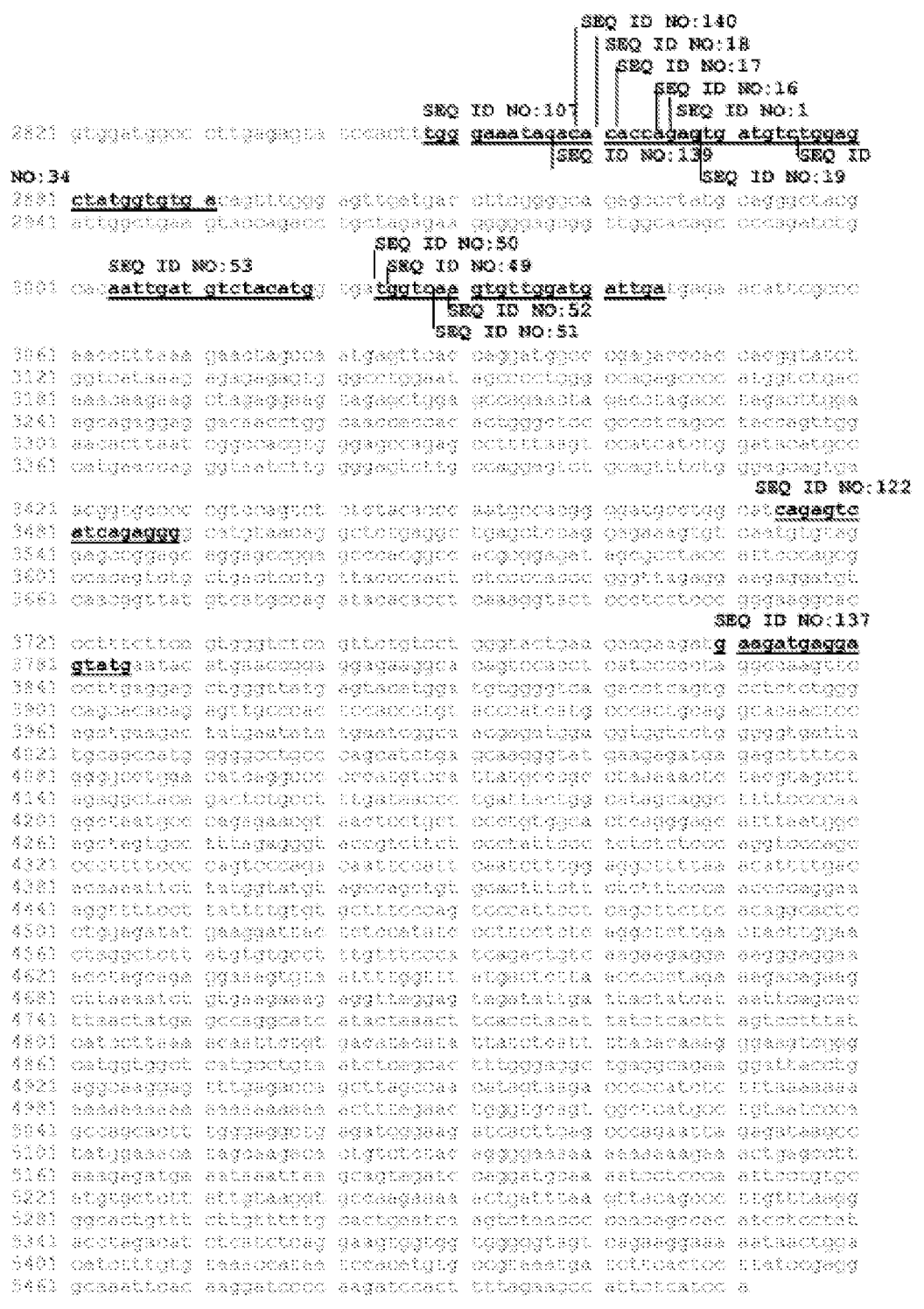

Further provided are target nucleic acids (e.g., DNA or mRNA encoding HER3), that contain target regions that are complementary or partially-complementary to one or more of the oligomers of SEQ ID NOs: 1-140, wherein the oligomers are capable of inhibiting expression (e.g., by down-regulation) of HER3 protein or mRNA. For example, target regions of human HER3 mRNA which are complementary to the antisense oligomers having sequences of SEQ ID NOs: 1, 16, 17, 18, 19, 34, 49, 50, 51, 52, 53, 54, 55, 56, 57, 58, 59, 74, 75, 76, 91, 92, 107, 122, 137, 138, 139, and 140 are shown in FIG. 1 (bold and underlined, with the corresponding oligomer SEQ ID NOs indicated above).

In various embodiments, the oligomers have the base sequences shown in SEQ ID NOs: 141-168. In certain embodiments, the oligomers are LNA oligomers, for example, those having the sequences of SEQ ID NOS: 169-196 and 234, in particular those having the base sequences of SEQ ID NOs: 169, 170, 173, 174, 180, 181, 183, 185, 187, 188, 189, 190, 191, 192 and 194. In various embodiments, the oligomers are LNA oligomers such as those having base sequences of SEQ ID NOs: 169, 170, 172, 174, 175, 176 and 179. In some embodiments, the oligomers or a region thereof consist of or comprise a base sequence as shown in SEQ ID NOs: 169, 180 or 234. In some embodiments, conjugates of the invention include an oligomer having a base sequence as shown in SEQ ID NOs: 169, 180 or 234.

In certain embodiments, the oligomer of the invention may, suitably, comprise a region having a particular sequence, such as a sequence selected from SEQ ID NOs: 200-227, that is identically present in a shorter oligomer of the invention. Preferably, the region comprises 10-16 monomers. For example, the oligomers having the base sequences of SEQ ID NOs: 200-227 each comprise a region wherein the sequence of the region is identically present in shorter oligomers having sequences of SEQ ID NOs: 1, 16, 17, 18, 19, 34, 49, 50, 51, 52, 53, 54, 55, 56, 57, 58, 59, 74, 75, 76, 91, 92, 107, 122, 137, 138, 139, and 140, respectively. In some embodiments, oligomers which have fewer than 16 monomers, such as 10, 11, 12, 13, 14, or 15 monomers, have a region of at least 8, at least 9, at least 10, at least 11, at least 12, at least 13, at least 14 or 15, contiguous monomers of which the sequence is identically present in oligomers having sequences of SEQ ID NOS: 1, 16, 17, 18, 19, 34, 49, 50, 51, 52, 53, 54, 55, 56, 57, 58, 59, 74, 75, 76, 91, 92, 107, 122, 137, 138, 139, or 140. Hence, in various embodiments, the sequences of shorter oligomers are derived from the sequences of longer oligomers. In some embodiments, the sequences of oligomers having SEQ ID NOs disclosed herein, or the sequences of at least 10 contiguous monomers thereof, are identically present in longer oligomers. Typically an oligomer of the invention comprises a first region having a sequence that is identically present in SEQ ID NOs: 1, 16, 17, 18, 19, 34, 49, 50, 51, 52, 53, 54, 55, 56, 57, 58, 59, 74, 75, 76, 91, 92, 107, 122, 137, 138, 139, or 140, and if the oligomer is longer than the first region that is identically present in SEQ ID NOs: 1, 16, 17, 18, 19, 34, 49, 50, 51, 52, 53, 54, 55, 56, 57, 58, 59, 74, 75, 76, 91, 92, 107, 122, 137, 138, 139, or 140, the flanking regions of the oligomer have sequences that are complementary to the sequences flanking the target region of the target nucleic acid. Two such oligomers are SEQ ID NO: 1 and SEQ ID NO: 54.

In various embodiments, the oligomer comprises or consists of a sequence of monomers which is fully complementary (perfectly complementary) to a target region of a target nucleic acid which encodes a mammalian HER3.

However, in some embodiments, the sequence of the oligomer includes 1, 2, 3, or 4 (or more) mismatches as compared to the best-aligned target region of a HER3 target nucleic acid, and still sufficiently binds to the target region to effect inhibition of HER3 mRNA or protein expression. The destabilizing effect of mismatches on the Watson-Crick hydrogen-bonded duplex may, for example, be compensated by increased length of the oligomer and/or an increased number of nucleoside analogues, such as LNA monomers, present within the oligomer.

In various embodiments, the oligomer base sequence comprises no more than 3, such as no more than 2 mismatches compared to the base sequence of the best-aligned target region of, for example, a target nucleic acid which encodes a mammalian HER3.

The base sequences of the oligomers of the invention or of a region thereof are preferably at least 80% identical to a sequence selected from the group consisting of SEQ ID NOS: 200-227, 1-140 and 228-233, such as at least 85%, at least 90%, at least 91%, at least 92%, at least 93%, at least 94%, at least 95%, at least 96%, at least 97%, at least 98%, at least 99%, even 100% identical.

The base sequences of the oligomers of the invention or of a first region thereof are preferably at least 80% complementary to a sequence of a target region present in SEQ ID NOs: 197, 198 and/or 199 such as at least 85%, at least 90%, at least 91%, at least 92%, at least 93%, at least 94%, at least 95%, at least 96%, at least 97%, at least 98%, at least 99%, even 100% complementary.

In various embodiments, the sequence of the oligomer (or a first region thereof) is selected from the group consisting of SEQ ID NOs: 200-227, 1-140 and 228-233, or is selected from the group consisting of at least 10 contiguous monomers of SEQ ID NOs: 200-227, 1-140 and 228-233. In other embodiments, the sequence of the oligomer of the invention or a first region thereof optionally comprises 1, 2 or 3 base moieties that differ from those in oligomers having sequences of SEQ ID NOs: 200-227, 1-140 and 228-233, or the sequences of at least 10 contiguous monomers thereof, when optimally aligned with said selected sequence or region thereof.

In certain embodiments, the monomer region consists of 11, 12, 13, 14, 15, 16, 17, 18, 19, 20, 21, 22, 23, 24, 25, 26, 27, 28, or 29 contiguous monomers, such as between 10-15, 12-25, 12-22, such as between 12-18 monomers. Suitably, in various embodiments, the region is of the same length as the oligomer of the invention.

In some embodiments, the oligomer comprises additional monomers at the 5' or 3' ends, such as, independently, 1, 2, 3, 4 or 5 additional monomers 5' end and/or 3' end of the oligomer, which are non-complementary to the sequence of the target region. In various embodiments, the oligomer of the invention comprises a region that is complementary to the target, which is flanked 5' and/or 3' by additional monomers. In various embodiments, the 3' end of the region is flanked by 1, 2 or 3 DNA or RNA monomers. 3' DNA monomers are frequently used during solid state synthesis of oligomers. In various embodiments, which may be the same or different, the 5' end of the oligomer is flanked by 1, 2 or 3 DNA or RNA monomers. In certain embodiments, the additional 5' or 3' monomers are nucleosides, such as DNA or RNA monomers.

In various embodiments, the 5' or 3' monomers may represent region D as referred to in the context of gapmer oligomers herein.

In certain embodiments, the oligomer according to the invention consists of, or comprises, contiguous monomers having a nucleobase sequence according to SEQ ID NO:200, or according to a region thereof.

In certain embodiments, the oligomer according to the invention consists of, or comprises, contiguous monomers having a nucleobase sequence according to SEQ ID NO:201, or according to a region thereof.

In certain embodiments, the oligomer according to the invention consists of, or comprises, contiguous monomers having a nucleobase sequence according to SEQ ID NO:202, or according to a region thereof.

In certain embodiments, the oligomer according to the invention consists of, or comprises, contiguous monomers having a nucleobase sequence according to SEQ ID NO:203, or according to a region thereof.

In certain embodiments, the oligomer according to the invention consists of, or comprises, contiguous monomers having a nucleobase sequence according to SEQ ID NO:204, or according to a region thereof.

In certain embodiments, the oligomer according to the invention consists of, or comprises, contiguous monomers having a nucleobase sequence according to SEQ ID NO:205, or according to a region thereof.

In certain embodiments, the oligomer according to the invention consists of, or comprises, contiguous monomers having a nucleobase sequence according to SEQ ID NO:206, or according to a region thereof.

In certain embodiments, the oligomer according to the invention consists of, or comprises, contiguous monomers having a nucleobase sequence according to SEQ ID NO:207, or according to a region thereof.

In certain embodiments, the oligomer according to the invention consists of, or comprises, contiguous monomers having a nucleobase sequence according to SEQ ID NO:208, or according to a region thereof.

In certain embodiments, the oligomer according to the invention consists of, or comprises, contiguous monomers having a nucleobase sequence according to SEQ ID NO:209, or according to a region thereof.

In certain embodiments, the oligomer according to the invention consists of, or comprises, contiguous monomers having a nucleobase sequence according to SEQ ID NO:210, or according to a region thereof.

In certain embodiments, the oligomer according to the invention consists of, or comprises, contiguous monomers having a nucleobase sequence according to SEQ ID NO:211, or according to a region thereof.

In certain embodiments, the oligomer according to the invention consists of, or comprises, contiguous monomers having a nucleobase sequence according to SEQ ID NO:212, or according to a region thereof.

In certain embodiments, the oligomer according to the invention consists of, or comprises, contiguous monomers having a nucleobase sequence according to SEQ ID NO:213, or according to a region thereof.

In certain embodiments, the oligomer according to the invention consists of, or comprises, contiguous monomers having a nucleobase sequence according to SEQ ID NO:214, or according to a region thereof.

In certain embodiments, the oligomer according to the invention consists of, or comprises, contiguous monomers having a nucleobase sequence according to SEQ ID NO:215, or according to a region thereof.

In certain embodiments, the oligomer according to the invention consists of, or comprises, contiguous monomers having a nucleobase sequence according to SEQ ID NO:216, or according to a region thereof.

In certain embodiments, the oligomer according to the invention consists of, or comprises, contiguous monomers having a nucleobase sequence according to SEQ ID NO:217, or according to a region thereof.

In certain embodiments, the oligomer according to the invention consists of, or comprises, contiguous monomers having a nucleobase sequence according to SEQ ID NO:218, or according to a region thereof.

In certain embodiments, the oligomer according to the invention consists of, or comprises, contiguous monomers having a nucleobase sequence according to SEQ ID NO:219, or according to a region thereof.

In certain embodiments, the oligomer according to the invention consists of, or comprises, contiguous monomers having a nucleobase sequence according to SEQ ID NO:220, or according to a region thereof.

In certain embodiments, the oligomer according to the invention consists of, or comprises, contiguous monomers having a nucleobase sequence according to SEQ ID NO:221, or according to a region thereof.

In certain embodiments, the oligomer according to the invention consists of, or comprises, contiguous monomers having a nucleobase sequence according to SEQ ID NO:222, or according to a region thereof.

In certain embodiments, the oligomer according to the invention consists of, or comprises, contiguous monomers having a nucleobase sequence according to SEQ ID NO:223, or according to a region thereof.

In certain embodiments, the oligomer according to the invention consists of, or comprises, contiguous monomers having a nucleobase sequence according to SEQ ID NO:224, or according to a region thereof.

In certain embodiments, the oligomer according to the invention consists of, or comprises, contiguous monomers having a nucleobase sequence according to SEQ ID NO:225, or according to a region thereof.

In certain embodiments, the oligomer according to the invention consists of, or comprises, contiguous monomers having a nucleobase sequence according to SEQ ID NO:226, or according to a region thereof.

In certain embodiments, the oligomer according to the invention consists of, or comprises, contiguous monomers having a nucleobase sequence according to SEQ ID NO:227, or according to a region thereof.

Sequence alignments (such as those described above) can be used to identify regions of the nucleic acids encoding HER3 (or HER2 or EGFR) from human and one or more different mammalian species, such as monkey, mouse and/or rat, where there are sufficient stretches of nucleic acid identity between or among the species to allow the design of oligonucleotides which target (that is, which bind with sufficient specificity to inhibit expression of) both the human HER3 (or HER2 or EGFR) target nucleic acid and the corresponding nucleic acids present in the different mammalian species.

In some embodiments, such oligomers consist of or comprise regions of at least 10, such as at least 12, such as at least 14, such as at least 16, such as at least 18, such as 11, 12, 13, 14, 15, 16, 17 or 18 contiguous monomers which are 100% complementary in sequence to the sequence of the target regions of the nucleic acid encoding HER3 (or HER2 or EGFR) from humans and of the nucleic acid(s) encoding HER3 (or HER2 or EGFR) from a different mammalian species.

In some embodiments, the oligomer of the invention comprises or consists of a region of contiguous monomers having a sequence that is at least 80%, such as at least 85%, such as at least 90%, such as at least 95%, such as at least 98% or 100% complementary to the sequence of the target regions of both the nucleic acid encoding human HER3 (or HER2 or EGFR) and a nucleic acid(s) encoding HER3 (or HER2 or EGFR) from a different mammalian species, such as the mouse nucleic acid encoding HER3 (or HER2 or EGFR). It is preferable that the contiguous nucleobase sequence of the oligomer is 100% complementary to the target region of the human HER3 (or HER2 or EGFR) mRNA.

In some embodiments, oligomers of the invention bind to a target region of a HER3 target nucleic acid and down-regulate the expression of HER3 mRNA and/or protein. In various embodiments, oligomers of the invention that bind to a target region of a HER3 nucleic acid have the sequences shown, for example, in SEQ ID NOs:169-196 and 234.

In some embodiments, a first region of a bispecific oligomer of the invention binds to a target region of a HER 3 nucleic acid and a second region of the bispecific oligomer binds to a target region of a HER2 nucleic acid and said oligomer down-regulates the expression of HER3 and HER2. In various embodiments, the bispecific oligomer down-regulates the expression of HER 3 and HER2 to a different extent. In some embodiments, the first region and the second region of the oligomer are the same. In various embodiments, the first region and the second region of the oligomer overlap. In certain embodiments, the bispecific oligomers of the invention that bind to a target region of HER3 nucleic acid and a target region of HER2 nucleic acid have the sequences shown, for example, in SEQ ID NOs:177 and 178. In still other embodiments, a bispecific oligomer of the invention binds to a target region of HER3 nucleic acid and to a target region of EGFR nucleic acid and down-regulates the expression of HER3 and EGFR. In some embodiments, bispecific oligomers of the invention that bind to a target region of HER3 nucleic acid and to a target region of EGFR nucleic acid have the sequences shown, for example, in SEQ ID NOs: 171 and 173. In some embodiments, a first region of a bispecific oligomer of the invention binds to a target region of HER 3 nucleic acid and a second region of the bispecific oligomer binds to a target region of EGFR nucleic acid and said oligomer down-regulates the expression of HER3 and EGFR. In various embodiments, the bispecific oligomer down-regulates the expression of HER 3 and EGFR to a different extent. In some embodiments, the first region and the second region of the oligomer are the same. In various embodiments, the first region and the second region of the oligomer overlap. In yet further embodiments, trispecific oligomers of the invention bind to a target region of HER3 nucleic acid, to a target region of HER2 nucleic acid and to a target region of EGFR nucleic acid and down-regulate the expression of all three genes. In some embodiments, trispecific oligomers of the invention that bind to HER3, HER2 and EGFR have the sequences shown, for example, in SEQ ID NOs:169, 170, 172, 174-176 and 179. In some embodiments, a first region of a trispecific oligomer of the invention binds to a target region of HER 3 nucleic acid, a second region of the trispecific oligomer binds to a target region of EGFR nucleic acid, and a third region of the trispecific oligomer binds to a target region of HER2 nucleic acid, and said oligomers down-regulate the expression of HER3, HER2 and EGFR. In various embodiments, the trispecific oligomer down-regulates the expression of HER 3, HER2 and EGFR to different extents. In some embodiments, the first, second and third regions of the oligomer are the same. In various embodiments, the first, second and third regions of the oligomer overlap. In various embodiments, bispecific or trispecific oligomers have 1, 2, 3, 4, 5 or more mismatches when compared to the best-aligned target regions of, e.g., target nucleic acids having sequences shown in SEQ ID NO: 197, 198 and/or 199.

Nucleosides and Nucleoside Analogues

In various embodiments, at least one of the monomers present in the oligomer is a nucleoside analogue that contains a modified base, such as a base selected from 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In various embodiments, at least one of the monomers present in the oligomer is a nucleoside analogue that contains a modified sugar.

In some embodiments, the linkage between at least 2 contiguous monomers of the oligomer is other than a phosphodiester linkage.

In certain embodiments, the oligomer includes at least one monomer that has a modified base, at least one monomer (which may be the same monomer) that has a modified sugar, and at least one inter-monomer linkage that is non-naturally occurring.

Specific examples of nucleoside analogues useful in the oligomers described herein are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1 (in which some nucleoside analogues are shown as nucleotides):

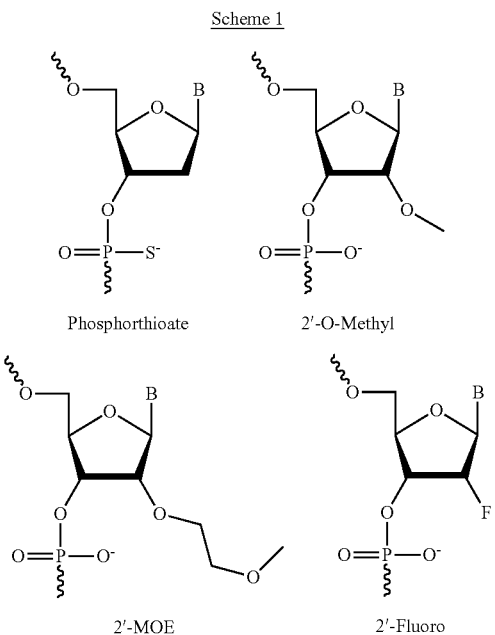

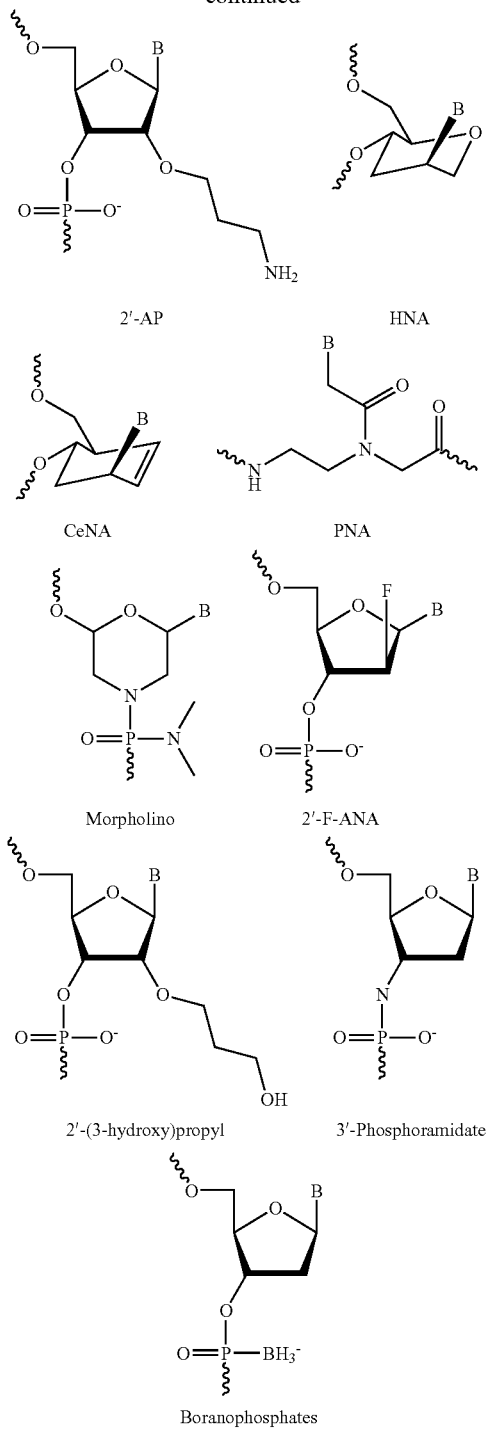

The oligomer may thus comprise or consist of a simple sequence of nucleosides—preferably DNA monomers, but also possibly RNA monomers, or a combination of nucleosides and one or more nucleoside analogues. In some embodiments, such nucleoside analogues suitably enhance the affinity of the oligomer for the target region of the target nucleic acid.

Examples of suitable and preferred nucleoside analogues are described in WO 2007/031091, incorporated herein by reference in its entirety, or are referenced therein.

In some embodiments, the nucleoside analogue comprises a sugar moiety modified to provide a 2'-substituent group, such as 2'-O-alkyl-ribose sugars, 2'-amino-deoxyribose sugars, and 2'-fluoro-deoxyribose sugars.

In some embodiments, the nucleoside analogue comprises a sugar in which a bridged structure, creating a bicyclic sugar (LNA), is present, which enhances binding affinity and may also provide some increased nuclease resistance. In various embodiments, the LNA monomer is selected from oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). In certain embodiments, the LNA monomers are beta-D-oxy-LNA. LNA monomers are further described below.

In various embodiments, incorporation of affinity-enhancing nucleoside analogues in the oligomer, such as LNA monomers or monomers containing 2'-substituted sugars, or incorporation of modified linkage groups provides increased nuclease resistance. In various embodiments, incorporation of such affinity-enhancing nucleoside analogues allows the size of the oligomer to be reduced, and also reduce the upper limit to the size of the oligomer before non-specific or aberrant binding takes place.

In certain embodiments, the oligomer comprises at least 2 nucleoside analogues. In some embodiments, the oligomer comprises from 3-8 nucleoside analogues, e.g. 6 or 7 nucleoside analogues. In preferred embodiments, at least one of the nucleoside analogues is a locked nucleic acid (LNA) monomer; for example at least 3 or at least 4, or at least 5, or at least 6, or at least 7, or 8 nucleoside analogues are LNA monomers. In some embodiments all the nucleosides analogues are LNA monomers.

It will be recognised that when referring to a preferred oligomer base sequence, in certain embodiments the oligomers comprise a corresponding nucleoside analogue, such as a corresponding LNA monomer or other corresponding nucleoside analogue, which raises the duplex stability ($T_m$) of the oligomer/target region duplex (i.e. affinity enhancing nucleoside analogues).

In various preferred embodiments, any mismatches (that is, noncomplementarities) between the base sequence of the oligomer and the base sequence of the target region, if present, are located other than in the regions of the oligomer that contain affinity-enhancing nucleoside analogues (e.g., regions A or C), such as within region B as referred to herein, and/or within region D as referred to herein, and/or in regions which are 5' or 3' to the region of the oligomer that is complementary to the target region.

In some embodiments the nucleoside analogues present within the oligomer of the invention (such as in regions A and C mentioned herein) are independently selected from, for example: monomers containing 2'-O-alkyl-ribose sugars, monomers containing 2'-amino-deoxyribose sugars, monomers containing 2'-fluoro-deoxyribose sugars, LNA monomers, monomers containing arabinose sugars ("ANA monomers"), monomers containing 2'-fluoro-arabinose sugars, monomers containing d-arabino-hexitol sugars ("HNA monomers"), intercalating monomers as defined in Christensen, Nucl. Acids. Res. 30: 4918-4925 (2002), hereby incorporated by reference, and monomers containing 2'MOE sugars. In certain embodiments, there is only one of the above types of nucleoside analogues present in the oligomer of the invention, or region thereof.

In certain embodiments, the nucleoside analogues contain 2'-O-methoxyethyl-ribose sugars (2'MOE), or 2'-fluorodeoxyribose sugars or LNA sugars, and as such the oligonucleotide of the invention may comprise nucleoside analogues which are independently selected from these three types. In certain oligomer embodiments containing nucleoside analogues, at least one of said nucleoside analogues contains a 2'-MOE-ribose sugar, such as 2, 3, 4, 5, 6, 7, 8, 9 or 10 nucleoside analogues containing 2'-MOE-ribose sugars. In certain embodiments, at least one of said nucleoside analogues contains a 2'-fluoro-deoxyribose sugar, such as 2, 3, 4, 5, 6, 7, 8, 9 or 10 nucleoside analogues containing 2'-fluoro-deoxyribose sugars.

In various embodiments, the oligomer according to the invention comprises at least one Locked Nucleic Acid (LNA) monomer, such as 1, 2, 3, 4, 5, 6, 7, or 8 LNA monomers, such as 3-7 or 4-8 LNA monomers, or 3, 4, 5, 6 or 7 LNA monomers. In various embodiments, all of the nucleoside analogues are LNA monomers. In some embodiments, the oligomer comprises both beta-D-oxy-LNA monomers, and one or more of the following LNA monomers: thio-LNA monomers, amino-LNA monomers, oxy-LNA monomers, and/or ENA monomers in either the beta-D or alpha-L configuration, or combinations thereof. In certain embodiments, the cytosine base moieties of all LNA monomers in the oligomer are 5-methylcytosines. In certain embodiments of the invention, the oligomer comprises both LNA and DNA monomers. Typically, the combined total of LNA and DNA monomers is 10-25, preferably 10-20, even more preferably 12-16. In certain embodiments of the invention, the oligomer or region thereof consists of at least one LNA monomer, and the remaining monomers are DNA monomers. In certain embodiments, the oligomer comprises only LNA monomers and nucleosides (such as RNA or DNA monomers, most preferably DNA monomers) optionally linked with modified linkage groups such as phosphorothioate.

In various embodiments, at least one of the nucleoside analogues present in the oligomer has a modified base selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA monomer" refers to a nucleoside analogue containing a bicyclic sugar (an "LNA sugar"). The terms "LNA oligonucleotide" and "LNA oligomer" refer to an oligomer containing one or more LNA monomers.

The LNA used in the oligonucleotide compounds of the invention preferably has the structure of the general formula I

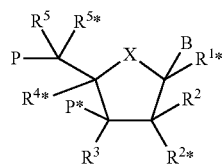

wherein X is selected from —O—, —S—, —N($R^{N*}$)—, —C($R^6R^{6*}$)—;

B is selected from hydrogen, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$ or equally applicable the substituent $R^{5*}$;

P* designates an internucleoside linkage to a preceding monomer, or a 3'-terminal group;

$R^{4*}$ and $R^{2*}$ together designate a biradical consisting of 1-4 groups/atoms selected from —C($R^aR^b$)—, —C($R^a$)=C($R^b$)—, —C($R^a$)=N—, —O—, —Si($R^a$)$_2$—, —S—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$), and each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —(N$R^N$)— where $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof;

In certain embodiments, $R^{5*}$ is selected from H, —$CH_3$, —$CH_2$—$CH_3$, —$CH_2$—O—$CH_3$, and —CH=$CH_2$.

In various embodiments, $R^{4*}$ and $R^{2*}$ together designate a biradical selected from —C($R^aR^b$)—O—, —C($R^aR^b$)—C($R^cR^d$)—O—, —C($R^aR^b$)—C($R^cR^d$)—C($R^eR^f$)—O—, —C($R^aR^b$)—O—C($R^cR^d$)—, —C($R^aR^b$)—O—C($R^cR^d$)—O—, —C($R^aR^b$)—C($R^cR^d$)—, —C($R^aR^b$)—C($R^cR^d$)—C($R^eR^f$)—, —C($R^a$)=C($R^b$)—C($R^cR^d$)—, —C($R^aR^b$)—N($R^c$)—, —C($R^aR^b$)—C($R^cR^d$)—N($R^e$)—, —C($R^aR^b$)—N ($R^c$)—O—, and —C($R^aR^b$)—S—, —C($R^aR^b$)—C($R^cR^d$)—S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkylamino, carbamoyl, mono- and di($C_{1-6}$-alkyl)-amino-carbonyl, amino-$C_{1-6}$-alkyl-aminocarbonyl, mono- and di($C_{1-6}$-alkyl) amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkyl-sulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$), In further embodiments $R^{4*}$ and $R^{2*}$ together designate a biradical selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —$CH_2$—O—$CH_2$—O—, —$CH_2$—NH—O—, —$CH_2$—N($CH_3$)—O—, —$CH_2$—O—$CH_2$—, —CH($CH_3$)—O—, —CH($CH_2$—O—$CH_3$)—O—.

For all chiral centers, asymmetric groups may be found in either R or S orientation.

Preferably, the LNA monomer used in the oligomers of the invention comprises at least one LNA monomer according to any of the formulas

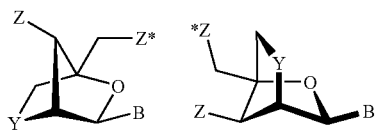

wherein Y is —O—, —O—$CH_2$—, —S—, —NH—, or N($R^H$); Z and Z* are independently selected among an internucleoside linkage, a terminal group or a protecting group; B constitutes an unmodified base moiety or a modified base moiety that either occurs naturally in nucleic acids or does not occur naturally in nucleic acids, and $R^H$ is selected from hydrogen and $C_{1-4}$-alkyl.

Specifically preferred LNA monomers are shown in Scheme 2:

Scheme 2

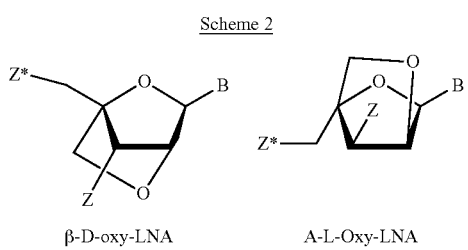

β-D-oxy-LNA      A-L-Oxy-LNA

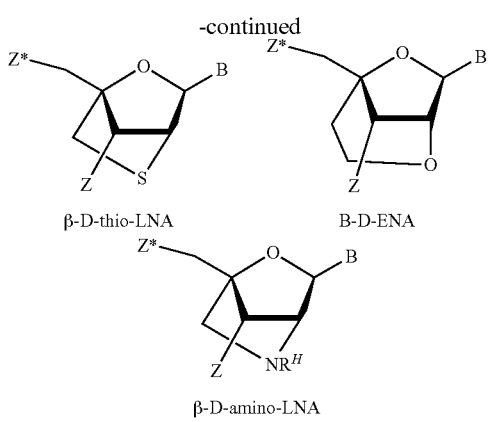

β-D-thio-LNA      B-D-ENA

β-D-amino-LNA

The term "thio-LNA" refers to an LNA monomer in which Y in the general formula above is selected from S or —$CH_2$—S—. Thio-LNA can be in either the beta-D or the alpha-L-configuration.

The term "amino-LNA" refers to an LNA monomer in which Y in the general formula above is selected from —N(H)—, N(R)—, $CH_2$—N(H)—, and —$CH_2$—N(R)— where R is selected from hydrogen and $C_{1-4}$-alkyl. Amino-LNA can be in either the beta-D or the alpha-L-configuration.

The term "oxy-LNA" refers to an LNA monomer in which Y in the general formula above represents —O— or —$CH_2$—O—. Oxy-LNA can be in either the beta-D or the alpha-L-configuration.

The term "ENA" refers to an LNA monomer in which Y in the general formula above is —$CH_2$—O— (where the oxygen atom of —$CH_2$—O— is attached to the 2'-position relative to the base B).

In a preferred embodiment the LNA monomer is selected from a beta-D-oxy-LNA monomer, an alpha-L-oxy-LNA monomer, a beta-D-amino-LNA monomer and a beta-D-thio-LNA monomer, in particular a beta-D-oxy-LNA monomer.

In the present context, the term "$C_{1-4}$-alkyl" means a linear or branched saturated hydrocarbon chain wherein the chain has from one to four carbon atoms, such as methyl, ethyl, n-propyl, isopropyl, n-butyl, isobutyl, sec-butyl and tert-butyl.

RNAse H Recruitment

In some embodiments, an oligomer functions via non-RNase-mediated degradation of a target mRNA, such as by steric hindrance of translation, or other mechanisms; however, in various embodiments, oligomers of the invention are capable of recruiting an endoribonuclease (RNase), such as RNase H.

Typically, the oligomer comprises a region of at least 6, such as at least 7 contiguous monomers, such as at least 8 or at least 9 contiguous monomers, including 7, 8, 9, 10, 11, 12, 13, 14, 15 or 16 contiguous monomers, which, when forming a duplex with the target region of the target RNA, is capable of recruiting RNase. The region of the oligomer which is capable of recruiting RNAse may be region B, as referred to in the context of a gapmer as described herein. In certain embodiments, the region of the oligomer which is capable of recruiting RNAse, such as region B, consists of 10, 11, 12, 13, 14, 15, 16, 17, 18, 19 or 20 monomers.

EP 1 222 309 provides in vitro methods for determining RNaseH activity, which may be used to determine the ability of the oligomers of the invention to recruit RNaseH. An oligomer is deemed capable of recruiting RNase H if, when contacted with the complementary target region of the RNA target, it has an initial rate, as measured in pmol/l/min, of at least 1%, such as at least 5%, such as at least 10% or less than 20% of an oligonucleotide having the same base sequence but containing only DNA monomers, with no 2' substitutions, with phosphorothioate linkage groups between all monomers in the oligonucleotide, using the methodology provided by Example 91-95 of EP 1 222 309, incorporated herein by reference.

In various embodiments, an oligomer is deemed essentially incapable of recruiting RNaseH if, when contacted with the complementary target region of the RNA target, and RNaseH, the RNaseH initial rate, as measured in pmol/l/min, is less than 1%, such as less than 5%, such as less than 10% or less than 20% of the initial rate determined using an oligonucleotide having the same base sequence, but containing only DNA monomers, with no 2' substitutions, with phosphorothioate linkage groups between all monomers in the oligonucleotide, using the methodology provided by Example 91-95 of EP 1 222 309.

In other embodiments, an oligomer is deemed capable of recruiting RNaseH if, when contacted with the complementary target region of the RNA target, and RNaseH, the RNaseH initial rate, as measured in pmol/l/min, is at least 20%, such as at least 40%, such as at least 60%, such as at least 80% of the initial rate determined using an oligonucleotide having the same base sequence, but containing only DNA monomers, with no 2' substitutions, with phosphorothioate linkage groups between all monomers in the oligonucleotide, using the methodology provided by Example 91-95 of EP 1 222 309.

Typically, the region of the oligomer that forms a duplex with the complementary target region of the target RNA and is capable of recruiting RNase contains DNA monomers and LNA monomers and forms a DNA/RNA like duplex with the target region. The LNA monomers are preferably in the alpha-L configuration, particularly preferred being alpha-L-oxy LNA.

In various embodiments, the oligomer of the invention comprises both nucleosides and nucleoside analogues, and is in the form of a gapmer as defined above, a headmer or a mixmer.

A "headmer" is defined as an oligomer that comprises a first region and a second region that is contiguous thereto, with the 5'-most monomer of the second region linked to the 3'-most monomer of the first region. The first region comprises a contiguous stretch of non-RNase-recruiting nucleoside analogues, and the second region comprises a contiguous stretch (such as at least 7 contiguous monomers) of DNA monomers or nucleoside analogue monomers recognizable and cleavable by the RNAse.

A "tailmer" is defined as an oligomer that comprises a first region and a second region that is contiguous thereto, with the 5'-most monomer of the second region linked to the 3'-most monomer of the first region. The first region comprises a contiguous stretch (such as at least 7 such monomers) of DNA monomers or nucleoside analogue monomers recognizable and cleavable by the RNase, and the second region comprises a contiguous stretch of non-RNase recruiting nucleoside analogue monomers.

Other "chimeric" oligomers, called "mixmers", consist of an alternating composition of (i) DNA monomers or nucleoside analogue monomers recognizable and cleavable by RNase, and (ii) non-RNase recruiting nucleoside analogue monomers.

In some embodiments, in addition to enhancing affinity of the oligomer for the target region, some nucleoside analogues also mediate RNase (e.g., RNase H) binding and cleavage. Since α-L-LNA monomers recruit RNase activity to a certain extent, in some embodiments, gap regions (e.g., region B as referred to herein below) of oligomers containing α-L-LNA monomers consist of fewer monomers recognizable and cleavable by the RNase, and more flexibility in the mixmer construction is introduced.

Conjugates

In the context of this disclosure, the term "conjugate" indicates a compound formed by the covalent attachment ("conjugation") of an oligomer, as described herein, to one or more moieties that are not themselves nucleic acids or monomers ("conjugated moiety"). Examples of such conjugated moieties include macromolecular compounds such as proteins, fatty acid chains, sugar residues, glycoproteins, polymers, or combinations thereof. Typically, proteins may be antibodies for a target protein. Typical polymers may be polyethylene glycol. WO 2007/031091 provides suitable moieties and conjugates, which are hereby incorporated by reference.

Accordingly, provided herein are conjugates comprising an oligomer as herein described, and at least one conjugated moiety that is not a nucleic acid or monomer, covalently attached to said oligomer. Therefore, in certain embodiments, where the oligomer of the invention consists of contiguous monomers having a specified sequence of bases, as herein disclosed, the conjugate may also comprise at least one conjugated moiety that is covalently attached to said oligomer.

In certain embodiments, the oligomer is conjugated to a moiety that increases the cellular uptake of oligomeric compounds.

In various embodiments, conjugates may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

In certain embodiments, the oligomers of the invention are conjugated to active drug substances, for example, aspirin, ibuprofen, a sulfa drug, an antidiabetic, an antibacterial or an antibiotic.

In certain embodiments, the conjugated moiety is a sterol, such as cholesterol.

In various embodiments, the conjugated moiety comprises or consists of a positively charged polymer, such as a positively charged peptide of, for example 1-50, such as 2-20 such as 3-10 amino acid residues in length, and/or polyalkylene oxide such as polyethylene glycol (PEG) or polypropylene glycol—see WO 2008/034123, hereby incorporated by reference. Suitably, the positively charged polymer, such as a polyalkylene oxide may be attached to the oligomer of the invention via a linker such as the releasable inker described in WO 2008/034123.

Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that in some embodiments is hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl.

In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis.

In some embodiments, the oligomers are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligomer via an ester group (—O—C(O)—$(CH_2)_w$NH).

In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)_w$SH). In some embodiments, sulfhydryl-activated oligonucleotides are conjugated with polymer moieties such as polyethylene glycol or peptides (via formation of a disulfide bond).

Activated oligomers covalently linked to at least one functional moiety can be synthesized by any method known in the art, and in particular by methods disclosed in U.S. Patent Publication No. 2004/0235773, which is incorporated herein by reference in its entirety, and in Zhao et al. (2007) J. Controlled Release 119:143-152; and Zhao et al. (2005) Bioconjugate Chem. 16:758-766.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention have amine-containing functional moieties on the nucleobase, including on the N6 purine amino groups, on the exocyclic N2 of guanine, or on the N4 or 5 positions of cytosine. In some embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Compositions

In various embodiments, the oligomer of the invention is used in pharmaceutical formulations and compositions. Suitably, such compositions comprise a pharmaceutically acceptable diluent, carrier, salt or adjuvant. WO2007/031091 provides suitable and preferred pharmaceutically acceptable diluents, carriers and adjuvants—which are hereby incorporated by reference. Suitable dosages, formulations, administration routes, compositions, dosage forms, combinations with other therapeutic agents, pro-drug formulations are also provided in WO2007/031091—which are also hereby incorporated by reference. Details on techniques for formulation and administration also may be found in the latest edition of "REMINGTON'S PHARMACEUTICAL SCIENCES" (Maack Publishing Co, Easton Pa.).

In some embodiments, an oligomer of the invention is covalently linked to a conjugated moiety to aid in delivery of the oligomer across cell membranes. An example of a conjugated moiety that aids in delivery of the oligomer across cell membranes is a lipophilic moiety, such as cholesterol. In various embodiments, an oligomer of the invention is formulated with lipid formulations that form liposomes, such as Lipofectamine 2000 or Lipofectamine RNAiMAX, both of which are commercially available from Invitrogen. In some embodiments, the oligomers of the invention are formulated with a mixture of one or more lipid-like non-naturally occurring small molecules ("lipidoids"). Libraries of lipidoids can be synthesized by conventional synthetic chemistry methods and various amounts and combinations of lipidoids can be assayed in order to develop a vehicle for effective delivery of an oligomer of a particular size to the targeted tissue by the chosen route of administration. Suitable lipidoid libraries and compositions can be found, for example in Akinc et al. (2008) Nature Biotechnol., available at http://www.nature.com/nbt/journal,vaop/ncurrent/abs/nbt1402.html, which is incorporated by reference herein.

As used herein, the term "pharmaceutically acceptable salts" refers to salts that retain the desired biological activity of the herein identified compounds and exhibit acceptable levels of undesired toxic effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N'-dibenzylethylenediamine, D-glucosamine, tetraethylammonium, or ethylenediamine; or (c) combinations of (a) and (b); e.g., a zinc tannate salt or the like.

Applications

The term "treatment" as used herein refers to both treatment of an existing disease (e.g., a disease or disorder as referred to herein below), or prevention of a disease, i.e., prophylaxis. It will therefore be recognised that, in certain embodiments, "treatment" includes prophylaxis.

In various embodiments, the oligomers of the invention may be utilized as research reagents for, for example, diagnostics, therapeutics and prophylaxis.

In some embodiments, such oligomers may be used for research purposes to specifically inhibit the expression of HER3 (and/or HER2 and/or EGFR) protein (typically, by degrading or inhibiting the HER3 (and/or HER2 and/or EGFR) mRNA and thereby preventing protein formation) in cells and experimental animals, thereby facilitating functional analysis of the target or an appraisal of its usefulness as a target for therapeutic intervention.

In certain embodiments, the oligomers may be used in diagnostics to detect and quantitate HER3 (and/or HER2 and/or EGFR) expression in cells and tissues by northern blotting, in-situ hybridisation or similar techniques.

In various therapeutic embodiments, a non-human animal or a human, suspected of having a disease or disorder, which can be treated by modulating the expression of HER3 (and optionally HER2 and/or EGFR) is treated by administering an effective amount of an oligomer (or conjugate thereof) in accordance with this invention. Further provided are methods of treating a mammal, such as treating a human, suspected of having or being prone to a disease or condition, associated with expression of HER3 (and/or HER2 and/or EGFR) by administering a therapeutically or prophylactically effective amount of one or more of the oligomers or compositions of the invention.

In certain embodiments, the invention also provides for the use of the compounds or conjugates of the invention as described for the manufacture of a medicament for the treatment of a disorder as referred to herein, or for a method of the treatment of a disorder as referred to herein.

In various embodiments, the invention also provides for a method for treating a disorder as referred to herein said method comprising administering a compound according to the invention as herein described, and/or a conjugate according to the invention, and/or a pharmaceutical composition according to the invention to a patient in need thereof.

In various embodiments, the invention relates to an oligomer, a composition or a conjugate thereof as described herein for use as a medicament.

In various embodiments, the invention provides for a method for treating a disorder as referred to herein, the method comprising administering an effective amount of a compound according to the invention as herein described, and/or an effective amount of a conjugate according to the invention, and/or a pharmaceutical composition according to the invention to a patient in need thereof.

In various embodiments, the oligomer, or conjugate thereof, induces a desired therapeutic effect in humans through, for example, hydrogen bonding to a target nucleic acid. The oligomer causes a decrease (e.g., inhibition) in the expression of a target via hydrogen bonding (e.g., hybridisation) to the mRNA of the target thereby resulting in a reduction in gene expression.

It is highly preferred that the compounds of the invention are capable of hybridising to the target nucleic acid, such as HER3 mRNA, by Watson-Crick base pairing.

Medical Indications

In certain therapeutic embodiments, the disorder to be treated is selected from the group consisting of a hyperproliferative disorder, such as cancer, such as a cancer selected from the group consisting of lymphomas and leukemias (e.g. non-Hodgkin's lymphoma, Hodgkin's lymphoma, acute leukemia such as acute lymphocytic leukemia, acute myelocytic leukemia, chronic myeloid leukemia, chronic lymphocytic leukemia, multiple myeloma), colon carcinoma, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumour, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma, heavy chain disease, metastases, or any disease or disorder characterized by uncontrolled or abnormal cell growth.

In certain embodiments, the disease is a cancer selected from the group consisting of breast cancer, lung cancer, ovarian cancer, prostate cancer, colon cancer, and brain cancer.

In certain other embodiments, the disease is a mammary carcinoma.

In various embodiments, the treatment of such a disease or condition according to the invention may be combined with one or more other anti-cancer treatments, such as radiotherapy, chemotherapy or immunotherapy.

In certain embodiments, the disease or disorder is associated with a mutation in the HER3 gene (and/or the HER2 gene and/or the EGFR gene) or a gene whose protein product is associated with or interacts with HER3. Therefore, in various embodiments, the target mRNA is a mutated form of the HER3 sequence; for example, it comprises one or more single point mutations, such as SNPs associated with cancer.

In certain embodiments, the disease or disorder is associated with abnormal levels of a mutated form of HER3. In certain embodiments, the disease or disorder is associated with abnormal levels of a wild-type form of HER3. One aspect of the invention is directed to a method of treating a mammal suffering from or susceptible to conditions associated with abnormal levels of HER3, comprising administering to the mammal a therapeutically effective amount of an oligomer of the invention targeted to HER3 or various conjugates thereof. In some embodiments, the oligomer comprises one or more LNA units.

In various embodiments, the invention is directed to a method of treating a mammal suffering from or susceptible to conditions associated with abnormal levels of a mutated form of HER2, or abnormal levels of a wild-type form of HER2, comprising administering to the mammal a therapeutically effective amount of an oligomer of the invention targeted to HER3 (and/or to HER2 and/or to EGFR) or various conjugates thereof. In some embodiments, the oligomer comprises one or more LNA units.

In still other embodiments, the invention is directed to a method of treating a mammal suffering from or susceptible to conditions associated with abnormal levels of a mutated EGFR, or abnormal levels of a wild-type EGFR, comprising administering to the mammal a therapeutically effective amount of an oligomer of the invention targeted to HER3 (and/or to HER2 and/or to EGFR). In some embodiments, the oligomer comprises one or more LNA units.

Suitable dosages, formulations, administration routes, compositions, dosage forms, combinations with other therapeutic agents, prodrug formulations are also provided in WO 2007/031091, which is hereby incorporated by reference. The invention also provides for a pharmaceutical composition comprising a compound or a conjugate as herein described or a conjugate and a pharmaceutically acceptable diluent, carrier or adjuvant. WO 2007/031091 provides suitable and preferred pharmaceutically acceptable diluents, carriers and adjuvants, which are hereby incorporated by reference.

In various embodiments, the invention described herein encompasses a method of preventing or treating a disease comprising administering a therapeutically effective amount of a HER3 modulating oligomer (and/or a HER2 modulating oligomer and/or an EGFR modulating oligomer) to a human in need of such therapy. The invention further encompasses the use of a short period of administration of a HER3 modulating oligonucleotide compound (oligomer or conjugate) (and/or a HER2 modulating oligomer and/or an EGFR modulating oligomer).

Combination with Other Antisense oligomers

In some embodiments, oligomers of the invention are targeted to HER3, HER2 and/or EGFR nucleic acids. Thus, in some embodiments, the invention relates to the use of more than one oligomer to target two or even all three target nucleic acids. In various embodiments, an oligomer which targets HER3 is administered with a second oligomer which targets either EGFR or HER2. In various other embodiments, an oligomer which targets HER3 is administered with a second oligomer which targets HER2 and a third oligomer that targets EGFR. Such oligomers can be administered concurrently, or sequentially.

In various embodiments the invention relates to a pharmaceutical composition that comprises an oligomer targeted to HER3, and a further therapeutic agent which targets and down-regulates HER2 expression, such as an antisense oligomer which targets HER2 mRNA.

In other embodiments, which may be the same or different, the invention relates to a pharmaceutical composition comprising an oligomer targeted to HER3, and a further therapeutic agent which targets and down-regulates EGFR expression, such as an antisense oligomer which target EGFR mRNA.

In some embodiments, oligomers that target HER2 and/or EGFR mRNA (or conjugates thereof), have the same designs (e.g., gapmers, headmers, tailmers) as oligomers that target HER3. In various embodiments, oligomers that target HER2 and/or EGFR mRNA (or conjugates thereof), have different designs from oligomers that target HER3.

Kits

The invention also provides a kit comprising a first component and a second component. In various embodiments, said first component comprises an oligomer of the invention that is capable of inhibiting (e.g., by down-regulating) expression of HER3, or a conjugate and/or pharmaceutical composition thereof. In other embodiments, the second component comprises a second active ingredient. In some embodiments, the second component is a therapeutic agent that is an oligonucleotide as described herein. In other embodiments, the therapeutic agent is other than an oligonucleotide (e.g., a small molecule therapeutic agent such as taxol). In some embodiments, kits of the invention are used in methods of treating a hyperproliferative disorder, such as cancer, which comprises administering to a patient in need thereof an effective amount of a first component and a second component of the kit. In various embodiments, the first and second components are administered simultaneously. In other embodiments, the first and second components are administered sequentially and in any order.

In some embodiments, the kit comprises a first component that comprises an oligomer of the invention that is capable of inhibiting (e.g., by down-regulating) expression of HER3, or a conjugate and/or pharmaceutical composition thereof, and a second component that is an antisense oligonucleotide capable of inhibiting (e.g., by down-regulating) the expression of HER2 and/or EGFR expression as described herein, or a conjugate and/or pharmaceutical composition thereof.

Further Embodiments

The following embodiments also relate to the description and summary of the invention, and may be combined with the embodiments of the invention referred to therein including the embodiments referred to in the claims:

1. An antisense oligonucleotide capable of binding to a target sequence of the HER3 gene of SEQ ID NO: 197 or allele thereof and down-regulating expression of HER3, said oligonucleotide comprising a sequence of 10-50 nucleobases corresponding to the target sequence.

2. The antisense oligonucleotide of embodiment 1, wherein the target sequence is selected from regions of the HER3 gene represented by SEQ ID NOS: 1-140 or an allelic variant thereof.

3. The oligonucleotide of embodiment 1 or embodiment 2 comprising a sequence of 10-16 nucleobases shown in SEQ ID NOS: 1, 16, 17, 18, 19, 34, 49, 50, 51, 52, 53, 54, 55, 56, 57, 58, 59, 74, 75, 76, 91, 92, 107, 122, 137, 138, 139 and 140 or an allelic variant thereof.

4. The oligonucleotide according to any one of embodiments 1-3 comprising any one of the sequences shown as SEQ ID NOS: 1-140.

5. The oligonucleotide of any one of the preceding embodiments represented by SEQ ID NOS: 141-196.

6. The oligonucleotide of embodiment 1, wherein said oligonucleotide is further capable of down-regulating expression of the HER2 gene of SEQ ID NO: 199, or an allelic variant thereof, and/or the EGFR gene of SEQ ID NO:198, or an allelic variant thereof.

7. The oligonucleotide of embodiment 6, wherein said oligonucleotide is capable of down-regulating the expression of the HER2 gene of SEQ ID NO: 199, or an allelic variant thereof, and wherein the oligonucleotide is represented by SEQ ID NO: 177 or 178.

8. The oligonucleotide of embodiment 6, wherein said oligonucleotide is capable of down-regulating the expression of the EGFR gene of SEQ ID NO: 198, or an allelic variant thereof, and wherein the oligonucleotide is represented by SEQ ID NO: 171 or 173.

9. The oligonucleotide of embodiment 6, wherein said oligonucleotide is capable of down-regulating expression of the HER2 gene of SEQ ID NO: 199, or an allelic variant thereof, and the EGFR gene of SEQ ID NO: 198, or an allelic variant thereof.

10. The oligonucleotide of embodiment 9, wherein said oligonucleotide is represented by any one of SEQ ID NOS: 169, 170, 172, 174, 175, 176 and 179.

11. The oligonucleotide according to any one of the preceding embodiments, wherein said nucleobase sequence comprises internucleobase linkages independently selected from phosphodiester, phosphorothioate and boranophosphate.

12. The oligonucleotide of any one of the preceding embodiments, wherein at least two of said nucleobases are nucleotide analogues.

13. The oligonucleotide according to embodiment 5, wherein said sequence of nucleobases comprises, in a 5' to 3' direction (i) region A: a stretch of 2-4 nucleotide analogues, followed by (ii) region B: a stretch of 6-11 nucleotides or nucleotide analogues different from those of region A, followed by (iii) region C: a stretch of 2-4 nucleotide analogues, and optionally followed by (iv) region D: one or two nucleotides.

14. The oligonucleotide according to embodiment 13, wherein the region A comprises at least one phosphodiester linkage between two nucleotide analogue units and/or or a nucleotide analogue unit and a nucleobase unit of Region B.

15. The oligonucleotide according to embodiment 13 or embodiment 14, wherein region C comprises at least one phosphodiester linkage between two nucleotide analogue units and/or a nucleotide analogue unit and a nucleobase unit of Region B.

16. The oligonucleotide according to any one of embodiments 1 to 11, wherein all the internucleobase linkages are phosphorothioate.

17. The oligonucleotide according to any one of embodiments 12 to 16, wherein said nucleotide analogue units are independently selected from 2'-O-alkyl-RNA, 2'-amino-DNA, 2'-fluoro-DNA, locked nucleic acid (LNA), arabino nucleic acid (ANA), 2'-fluoro-ANA, HNA, intercalating nucleic acid (INA) and 2'-MOE.

18. The oligonucleotide according to embodiment 17, wherein the nucleotide analogues are independently selected from 2'-MOE-RNA, 2'-fluoro-DNA, and LNA.

19. The oligonucleotide according to embodiment 18, wherein at least one of said nucleotide analogues is a locked nucleic acid (LNA).

20. The oligonucleotide according to embodiment 19, wherein all the nucleotide analogues are LNA.

21. The oligonucleotide according to any one of embodiments 17 to 20, wherein LNA is selected from beta-D-oxy-LNA, alpha-L-oxy-LNA, beta-D-amino-LNA and beta-D-thio-LNA.

22. A conjugate comprising an oligonucleotide of any one of the preceding embodiments and at least one non-nucleotide or non-polynucleotide moiety covalently attached to said oligonucleotide.

23. A conjugate according to embodiment 22, wherein said non-nucleotide or non-polynucleotide moiety consists of or comprises a sterol group, for example cholesterol.

24. A pharmaceutical composition comprising an oligonucleotide according to any one of the embodiments 1 to 21 or a conjugate according to embodiment 22 or embodiment 23, and a pharmaceutically acceptable diluent, carrier or adjuvant.

25. An oligonucleotide or a conjugate according to any one of embodiments 1 to 23 for use as a medicament.

26. Use of an oligonucleotide or a conjugate according to any one of embodiments 1 to 23 for the manufacture of a medicament for the treatment of abnormal levels of HER3 and/or HER2 and/or EGFR or a disease or condition for which down-regulation of HER3 and/or HER2 and/or EGFR expression is indicated.

27. The use according to embodiment 26, wherein said disease or condition is cancer.

28. A method of treating a subject suffering from cancer, the method comprising the step of administering a pharmaceutical composition, oligonucleotide or conjugate according to any one of embodiments 1 to 24 to the subject in need thereof.

29. The use or the method of embodiment 27 or 28, wherein the cancer is selected from breast cancer, lung cancer, ovarian cancer, prostate cancer, colon cancer and brain cancer.

30. A target sequence within the HER3 gene, wherein an antisense oligonucleotide corresponding to said target sequence is capable of down-regulating the expression of HER3.

31. The target sequence of embodiment 30, wherein the target sequence is selected from the regions of the HER3 gene complementary to SEQ ID NOs 1-140 or allelic variants thereof.

32. A method of down-regulating the expression of HER3 in a cell, comprising contacting the cell with an oligonucleotide according to any one of embodiments 1-21.

EXAMPLES

Example 1

Monomer Synthesis

The LNA monomer building blocks and derivatives thereof were prepared according to published procedures. See WO07/031,081 and the references cited therein.

Example 2

Oligonucleotide Synthesis

Oligonucleotides were synthesized according to the method described in WO07/031,081. Table 1 shows examples of antisense oligonucleotide motifs of the invention.

Example 3

Design of the Oligonucleotides

In accordance with the invention, a series of oligonucleotides were designed to target different regions of human EGFR (GenBank Accession number NM_005228, SEQ ID NO: 198) and human HER2 (GenBank Accession number NM_004448, SEQ ID NO: 199) in addition to human HER3 (GenBank Accession number NM_001982, SEQ ID NO: 197).

Of the sequences shown in Table 1, below, SEQ ID NOs: 1-50, 53, 139 and 140 were designed to target human EGFR and human HER2 in addition to human HER3. The percentage of sequence homology with HER3, EGFR and HER2 is indicated. The sequences of the oligomers contain 0-2 mismatches when compared to the sequences of the best-aligned target regions of EGFR, and 1-2 mismatches when compared to the sequences of the best-aligned target regions of HER2.

TABLE 1

Antisense Oligonucleotide Sequences

| SEQ ID NO | Sequence (5'-3') | Length (bases) | Target site HER3 | Compl EGFR | Compl HER2 |
|---|---|---|---|---|---|
| SEQ ID NO: 1 | GCTCCAGACATCACTC | 16 | 2866-2881 | 100% | 87.5% |
| SEQ ID NO: 2 | GCTCCAGACATCACT | 15 | | | |
| SEQ ID NO: 3 | CTCCAGACATCACTC | 15 | | | |
| SEQ ID NO: 4 | GCTCCAGACATCAC | 14 | | | |
| SEQ ID NO: 5 | CTCCAGACATCACT | 14 | | | |
| SEQ ID NO: 6 | TCCAGACATCACTC | 14 | | | |
| SEQ ID NO: 7 | GCTCCAGACATCA | 13 | | | |
| SEQ ID NO: 8 | CTCCAGACATCAC | 13 | | | |
| SEQ ID NO: 9 | TCCAGACATCACT | 13 | | | |
| SEQ ID NO: 10 | CCAGACATCACTC | 13 | | | |
| SEQ ID NO: 11 | GCTCCAGACATC | 12 | | | |
| SEQ ID NO: 12 | CTCCAGACATCA | 12 | | | |
| SEQ ID NO: 13 | TCCAGACATCAC | 12 | | | |
| SEQ ID NO: 14 | CCAGACATCACT | 12 | | | |
| SEQ ID NO: 15 | CAGACATCACTC | 12 | | | |
| SEQ ID NO: 16 | CTCCAGACATCACTCT | 16 | 2865-2880 | 100% | 93.8% |
| SEQ ID NO: 17 | CAGACATCACTCTGGT | 16 | 2862-2877 | 100% | 93.8% |
| SEQ ID NO: 18 | AGACATCACTCTGGTG | 16 | 2861-2876 | 100% | 93.8% |
| SEQ ID NO: 19 | ATAGCTCCAGACATCA | 16 | 2869-2884 | 93.8% | 87.5% |
| SEQ ID NO: 20 | ATAGCTCCAGACATC | 15 | | | |
| SEQ ID NO: 21 | TAGCTCCAGACATCA | 15 | | | |
| SEQ ID NO: 22 | ATAGCTCCAGACAT | 14 | | | |
| SEQ ID NO: 23 | TAGCTCCAGACATC | 14 | | | |
| SEQ ID NO: 24 | AGCTCCAGACATCA | 14 | | | |
| SEQ ID NO: 25 | ATAGCTCCAGACA | 13 | | | |
| SEQ ID NO: 26 | TAGCTCCAGACAT | 13 | | | |
| SEQ ID NO: 27 | AGCTCCAGACATC | 13 | | | |
| SEQ ID NO: 28 | GCTCCAGACATCA | 13 | | | |
| SEQ ID NO: 29 | ATAGCTCCAGAC | 12 | | | |
| SEQ ID NO: 30 | TAGCTCCAGACA | 12 | | | |
| SEQ ID NO: 31 | AGCTCCAGACAT | 12 | | | |

TABLE 1-continued

Antisense Oligonucleotide Sequences

| SEQ ID NO | Sequence (5'-3') | Length (bases) | Target site HER3 | Compl EGFR | Compl HER2 |
|---|---|---|---|---|---|
| SEQ ID NO: 32 | GCTCCAGACATC | 12 | | | |
| SEQ ID NO: 33 | CTCCAGACATCA | 12 | | | |
| SEQ ID NO: 34 | TCACACCATAGCTCCA | 16 | 2876-2891 | 87.5% | 93.8% |
| SEQ ID NO: 35 | TCACACCATAGCTCC | 15 | | | |
| SEQ ID NO: 36 | CACACCATAGCTCCA | 15 | | | |
| SEQ ID NO: 37 | TCACACCATAGCTC | 14 | | | |
| SEQ ID NO: 38 | CACACCATAGCTCC | 14 | | | |
| SEQ ID NO: 39 | ACACCATAGCTCCA | 14 | | | |
| SEQ ID NO: 40 | TCACACCATAGCT | 13 | | | |
| SEQ ID NO: 41 | CACACCATAGCTC | 13 | | | |
| SEQ ID NO: 42 | ACACCATAGCTCC | 13 | | | |
| SEQ ID NO: 43 | CACCATAGCTCCA | 13 | | | |
| SEQ ID NO: 44 | TCACACCATAGC | 12 | | | |
| SEQ ID NO: 45 | CACACCATAGCT | 12 | | | |
| SEQ ID NO: 46 | ACACCATAGCTC | 12 | | | |
| SEQ ID NO: 47 | CACCATAGCTCC | 12 | | | |
| SEQ ID NO: 48 | ACCATAGCTCCA | 12 | | | |
| SEQ ID NO: 49 | CATCCAACACTTGACC | 16 | 3025-3040 | 93.8% | 93.8% |
| SEQ ID NO: 50 | ATCCAACACTTGACCA | 16 | 3024-3039 | 93.8% | 93.8% |
| SEQ ID NO: 51 | CAATCATCCAACACTT | 16 | 3029-3044 | 87.5% | 93.8% |
| SEQ ID NO: 52 | TCAATCATCCAACACT | 16 | 3030-3045 | 87.5% | 93.8% |
| SEQ ID NO: 53 | CATGTAGACATCAATT | 16 | 3004-3019 | 87.5% | 93.8% |
| SEQ ID NO: 54 | TAGCCTGTCACTTCTC | 16 | 435-450 | 68.8% | 75% |
| SEQ ID NO: 228 | TAGCCTGTCACTTCT | 15 | | | |
| SEQ ID NO: 229 | AGCCTGTCACTTCTC | 15 | | | |
| SEQ ID NO: 230 | TAGCCTGTCACTTC | 14 | | | |
| SEQ ID NO: 231 | AGCCTGTCACTTCT | 14 | | | |
| SEQ ID NO: 232 | TAGCCTGTCACTT | 13 | | | |
| SEQ ID NO: 233 | TAGCCTGTCACT | 12 | | | |
| SEQ ID NO: 55 | AGATGGCAAACTTCCC | 16 | 530-545 | 68.8% | 68.8% |
| SEQ ID NO: 56 | CAAGGCTCACACATCT | 16 | 1146-1161 | 75% | 68.8% |
| SEQ ID NO: 57 | AAGTCCAGGTTGCCCA | 16 | 1266-1281 | 75% | 75% |
| SEQ ID NO: 58 | CATTCAAGTTCTTCAT | 16 | 1490-1505 | 75% | 68.8% |
| SEQ ID NO: 59 | CACTAATTTCCTTCAG | 16 | 1529-1544 | 81.3% | 68.8% |
| SEQ ID NO: 60 | CACTAATTTCCTTCA | 15 | | | |
| SEQ ID NO: 61 | ACTAATTTCCTTCAG | 15 | | | |
| SEQ ID NO: 62 | CACTAATTTCCTTC | 14 | | | |

TABLE 1-continued

Antisense Oligonucleotide Sequences

| SEQ ID NO | Sequence (5'-3') | Length (bases) | Target site HER3 | Compl EGFR | Compl HER2 |
|---|---|---|---|---|---|
| SEQ ID NO: 63 | ACTAATTTCCTTCA | 14 | | | |
| SEQ ID NO: 64 | CTAATTTCCTTCAG | 14 | | | |
| SEQ ID NO: 65 | CACTAATTTCCTT | 13 | | | |
| SEQ ID NO: 66 | ACTAATTTCCTTC | 13 | | | |
| SEQ ID NO: 67 | CTAATTTCCTTCA | 13 | | | |
| SEQ ID NO: 68 | TAATTTCCTTCAG | 13 | | | |
| SEQ ID NO: 69 | CACTAATTTCCT | 12 | | | |
| SEQ ID NO: 70 | ACTAATTTCCTT | 12 | | | |
| SEQ ID NO: 71 | CTAATTTCCTTC | 12 | | | |
| SEQ ID NO: 72 | TAATTTCCTTCA | 12 | | | |
| SEQ ID NO: 73 | AATTTCCTTCAG | 12 | | | |
| SEQ ID NO: 74 | GCCCAGCACTAATTTC | 16 | 1535-1550 | 75% | 68.8% |
| SEQ ID NO: 75 | CTTTGCCCTCTGCCAC | 16 | 1673-1688 | 75% | 75% |
| SEQ ID NO: 76 | CACACACTTTGCCCTC | 16 | 1679-1694 | 68.8% | 75% |
| SEQ ID NO: 77 | CACACACTTTGCCCT | 15 | | | |
| SEQ ID NO: 78 | ACACACTTTGCCCTC | 15 | | | |
| SEQ ID NO: 79 | CACACACTTTGCCC | 14 | | | |
| SEQ ID NO: 80 | ACACACTTTGCCCT | 14 | | | |
| SEQ ID NO: 81 | CACACTTTGCCCTC | 14 | | | |
| SEQ ID NO: 82 | CACACACTTTGCC | 13 | | | |
| SEQ ID NO: 83 | ACACACTTTGCCC | 13 | | | |
| SEQ ID NO: 84 | CACACTTTGCCCT | 13 | | | |
| SEQ ID NO: 85 | ACACTTTGCCCTC | 13 | | | |
| SEQ ID NO: 86 | CACACACTTTGC | 12 | | | |
| SEQ ID NO: 87 | ACACACTTTGCC | 12 | | | |
| SEQ ID NO: 88 | CACACTTTGCCC | 12 | | | |
| SEQ ID NO: 89 | ACACTTTGCCCT | 12 | | | |
| SEQ ID NO: 90 | CACTTTGCCCTC | 12 | | | |
| SEQ ID NO: 91 | CAGTTCCAAAGACACC | 16 | 2345-2360 | 75% | 68.8% |
| SEQ ID NO: 92 | TGGCAATTTGTACTCC | 16 | 2636-2651 | 75% | 68.8% |
| SEQ ID NO: 93 | TGGCAATTTGTACTC | 15 | | | |
| SEQ ID NO: 94 | GGCAATTTGTACTCC | 15 | | | |
| SEQ ID NO: 95 | TGGCAATTTGTACT | 14 | | | |
| SEQ ID NO: 96 | GGCAATTTGTACTC | 14 | | | |
| SEQ ID NO: 97 | GCAATTTGTACTCC | 14 | | | |
| SEQ ID NO: 98 | TGGCAATTTGTAC | 13 | | | |
| SEQ ID NO: 99 | GGCAATTTGTACT | 13 | | | |
| SEQ ID NO: 100 | GCAATTTGTACTC | 13 | | | |

TABLE 1-continued

Antisense Oligonucleotide Sequences

| SEQ ID NO | Sequence (5'-3') | Length (bases) | Target site HER3 | Compl EGFR | Compl HER2 |
|---|---|---|---|---|---|
| SEQ ID NO: 101 | CAATTTGTACTCC | 13 | | | |
| SEQ ID NO: 102 | TGGCAATTTGTA | 12 | | | |
| SEQ ID NO: 103 | GGCAATTTGTAC | 12 | | | |
| SEQ ID NO: 104 | GCAATTTGTACT | 12 | | | |
| SEQ ID NO: 105 | CAATTTGTACTC | 12 | | | |
| SEQ ID NO: 106 | AATTTGTACTCC | 12 | | | |
| SEQ ID NO: 107 | GTGTGTGTATTTCCCA | 16 | 2848-2863 | 75% | 68.8% |
| SEQ ID NO: 108 | GTGTGTGTATTTCCC | 15 | | | |
| SEQ ID NO: 109 | TGTGTGTATTTCCCA | 15 | | | |
| SEQ ID NO: 110 | GTGTGTGTATTTCC | 14 | | | |
| SEQ ID NO: 111 | TGTGTGTATTTCCC | 14 | | | |
| SEQ ID NO: 112 | GTGTGTATTTCCCA | 14 | | | |
| SEQ ID NO: 113 | GTGTGTGTATTTC | 13 | | | |
| SEQ ID NO: 114 | TGTGTGTATTTCC | 13 | | | |
| SEQ ID NO: 115 | GTGTGTATTTCCC | 13 | | | |
| SEQ ID NO: 116 | TGTGTATTTCCCA | 13 | | | |
| SEQ ID NO: 117 | GTGTGTGTATTT | 12 | | | |
| SEQ ID NO: 118 | TGTGTGTATTTC | 12 | | | |
| SEQ ID NO: 119 | GTGTGTATTTCC | 12 | | | |
| SEQ ID NO: 120 | TGTGTATTTCCC | 12 | | | |
| SEQ ID NO: 121 | GTGTATTTCCCA | 12 | | | |
| SEQ ID NO: 122 | CCCTCTGATGACTCTG | 16 | 3474-3489 | 68.8% | 68.8% |
| SEQ ID NO: 123 | CCCTCTGATGACTCT | 15 | | | |
| SEQ ID NO: 124 | CCTCTGATGACTCTG | 15 | | | |
| SEQ ID NO: 125 | CCCTCTGATGACTC | 14 | | | |
| SEQ ID NO: 126 | CCTCTGATGACTCT | 14 | | | |
| SEQ ID NO: 127 | CTCTGATGACTCTG | 14 | | | |
| SEQ ID NO: 128 | CCCTCTGATGACT | 13 | | | |
| SEQ ID NO: 129 | CCTCTGATGACTC | 13 | | | |
| SEQ ID NO: 130 | CTCTGATGACTCT | 13 | | | |
| SEQ ID NO: 131 | TCTGATGACTCTG | 13 | | | |
| SEQ ID NO: 132 | CCCTCTGATGAC | 12 | | | |
| SEQ ID NO: 133 | CCTCTGATGACT | 12 | | | |
| SEQ ID NO: 134 | CTCTGATGACTC | 12 | | | |
| SEQ ID NO: 135 | TCTGATGACTCT | 12 | | | |
| SEQ ID NO: 136 | CTGATGACTCTG | 12 | | | |
| SEQ ID NO: 137 | CATACTCCTCATCTTC | 16 | 3770-3785 | 81.3% | 81.3% |

TABLE 1-continued

Antisense Oligonucleotide Sequences

| SEQ ID NO | Sequence (5'-3') | Length (bases) | Target site HER3 | Compl EGFR | Compl HER2 |
|---|---|---|---|---|---|
| SEQ ID NO: 138 | CCACCACAAAGTTATG | 16 | 1067-1082 | 81.3% | 68.8% |
| SEQ ID NO: 139 | CATCACTCTGGTGTGT | 16 | 2858-2873 | 93.8% | 93.8% |
| SEQ ID NO: 140 | GACATCACTCTGGTGT | 16 | 2860-2875 | 93.8% | 87.5% |

In Table 2, bold letters represent shorter sequences shown in Table 1.

TABLE 2

HER3 24mer Sequences

| 16mer SEQ IDs | Corresponding 24mer sequence comprising 16mer | 24mer SEQ ID |
|---|---|---|
| SEQ ID NO: 1 | catagctccagacatcactctggt | SEQ ID NO: 200 |
| SEQ ID NO: 16 | atagctccagacatcactctggtg | SEQ ID NO: 201 |
| SEQ ID NO: 17 | gctccagacatcactctggtgtgt | SEQ ID NO: 202 |
| SEQ ID NO: 18 | ctccagacatcactctggtgtgtg | SEQ ID NO: 203 |
| SEQ ID NO: 19 | caccatagctccagacatcactct | SEQ ID NO: 204 |
| SEQ ID NO: 34 | actgtcacaccatagctccagaca | SEQ ID NO: 205 |
| SEQ ID NO: 49 | caatcatccaacacttgaccatca | SEQ ID NO: 206 |
| SEQ ID NO: 50 | aatcatccaacacttgaccatcac | SEQ ID NO: 207 |
| SEQ ID NO: 51 | tcatcaatcatccaacacttgacc | SEQ ID NO: 208 |
| SEQ ID NO: 52 | ctcatcaatcatccaacacttgac | SEQ ID NO: 209 |
| SEQ ID NO: 53 | tcaccatgtagacatcaattgtgc | SEQ ID NO: 210 |
| SEQ ID NO: 54 | gacatagcctgtcacttctcgaat | SEQ ID NO: 211 |
| SEQ ID NO: 55 | acgaagatggcaaacttcccatcg | SEQ ID NO: 212 |
| SEQ ID NO: 56 | cccacaaggctcacacatcttgag | SEQ ID NO: 213 |
| SEQ ID NO: 57 | cagaaagtccaggttgcccaggat | SEQ ID NO: 214 |
| SEQ ID NO: 58 | gtgacattcaagttcttcatgatc | SEQ ID NO: 215 |
| SEQ ID NO: 59 | ccagcactaatttccttcagggat | SEQ ID NO: 216 |
| SEQ ID NO: 74 | atacgcccagcactaatttccttc | SEQ ID NO: 217 |
| SEQ ID NO: 75 | cacactttgccctctgccacgcag | SEQ ID NO: 218 |
| SEQ ID NO: 76 | gggtcacacactttgccctctgcc | SEQ ID NO: 219 |
| SEQ ID NO: 91 | tgcacagttccaaagacacccgag | SEQ ID NO: 220 |
| SEQ ID NO: 92 | cccttggcaatttgtactccccag | SEQ ID NO: 221 |
| SEQ ID NO: 107 | tctggtgtgtgtatttcccaaagt | SEQ ID NO: 222 |
| SEQ ID NO: 122 | atgcccctctgatgactctgatgc | SEQ ID NO: 223 |
| SEQ ID NO: 137 | tattcatactcctcatcttcatct | SEQ ID NO: 224 |
| SEQ ID NO: 138 | tgatccaccacaaagttatgggga | SEQ ID NO: 225 |
| SEQ ID NO: 139 | cagacatcactctggtgtgtgtat | SEQ ID NO: 226 |
| SEQ ID NO: 140 | tccagacatcactctggtgtgtgt | SEQ ID NO: 227 |

In SEQ ID NOs: 141-168 shown in Table 3, uppercase letters indicate nucleoside analogue monomers and the subscript "s" represents a phosphorothioate linkage. Lowercase letters represent DNA monomers. The absence of "s" between monomers (if any) indicates a phosphodiester linkage.

TABLE 3

| Oligonucleotide gapmers | |
|---|---|
| SEQ ID NO | Sequence (5'-3') |
| SEQ ID NO: 141 | $G_sC_sT_sc_sc_sa_sg_sa_sc_sa_st_sc_sa_sC_sT_sC$ |
| SEQ ID NO: 142 | $C_sT_sC_sc_sa_sg_sa_sc_sa_st_sc_sa_sc_sT_sC_sT$ |
| SEQ ID NO: 143 | $C_sA_sG_sa_sc_sa_st_sc_sa_sc_st_sc_st_sG_sG_sT$ |
| SEQ ID NO: 144 | $A_sG_sA_sc_sa_st_sc_sa_sc_st_sc_st_sg_sG_sT_sG$ |
| SEQ ID NO: 145 | $A_sT_sA_sg_sc_st_sc_sc_sa_sg_sa_sc_sa_sT_sC_sA$ |
| SEQ ID NO: 146 | $T_sC_sA_sc_sa_sc_sc_sa_st_sa_sg_sc_st_sC_sC_sA$ |
| SEQ ID NO: 147 | $C_sA_sT_sc_sc_sa_sa_sc_sa_sc_st_st_sg_sA_sC_sC$ |
| SEQ ID NO: 148 | $A_sT_sC_sc_sa_sa_sc_sa_sc_st_st_sg_sa_sC_sC_sA$ |
| SEQ ID NO: 149 | $C_sA_sA_st_sc_sa_st_sc_sc_sa_sa_sc_sa_sC_sT_sT$ |
| SEQ ID NO: 150 | $T_sC_sA_sa_st_sc_sa_st_sc_sc_sa_sa_sc_sA_sC_sT$ |
| SEQ ID NO: 151 | $C_sA_sT_sg_st_sa_sg_sa_sc_sa_st_sc_sa_sA_sT_sT$ |
| SEQ ID NO: 152 | $T_sA_sG_sc_sc_st_sg_st_sc_sa_sc_st_st_sC_sT_sC$ |
| SEQ ID NO: 153 | $A_sG_sA_st_sg_sg_sc_sa_sa_sa_sc_st_st_sC_sC_sC$ |
| SEQ ID NO: 154 | $C_sA_sA_sg_sg_sc_st_sc_sa_sc_sa_sc_sa_sT_sC_sT$ |
| SEQ ID NO: 155 | $A_sA_sG_st_sc_sc_sa_sg_sg_st_st_sg_sc_sC_sC_sA$ |
| SEQ ID NO: 156 | $C_sA_sT_st_sc_sa_sa_sg_st_st_sc_st_st_sC_sA_sT$ |
| SEQ ID NO: 157 | $C_sA_sC_st_sa_sa_st_st_st_sc_sc_st_st_sC_sA_sG$ |
| SEQ ID NO: 158 | $G_sC_sC_sc_sa_sg_sc_sa_sc_st_sa_sa_st_sT_sT_sC$ |
| SEQ ID NO: 159 | $C_sT_sT_st_sg_sc_sc_sc_st_sc_st_sg_sc_sC_sA_sC$ |
| SEQ ID NO: 160 | $C_sA_sC_sa_sc_sa_sc_st_st_sg_sc_sc_sC_sT_sC$ |
| SEQ ID NO: 161 | $C_sA_sG_st_st_sc_sc_sa_sa_sa_sg_sa_sc_sA_sC_sC$ |
| SEQ ID NO: 162 | $T_sG_sG_sc_sa_sa_st_st_sg_st_sa_sc_sT_sC_sC$ |

TABLE 3-continued

| Oligonucleotide gapmers | |
|---|---|
| SEQ ID NO | Sequence (5'-3') |
| SEQ ID NO: 163 | $G_sT_sG_st_sg_st_sg_st_sa_st_st_sc_sC_sC_sA$ |
| SEQ ID NO: 164 | $C_sC_sC_st_sc_st_sg_sa_st_sg_sa_sc_st_sC_sT_sG$ |
| SEQ ID NO: 165 | $C_sA_sT_sa_sc_st_sc_sc_st_sc_sa_st_sc_sT_sT_sC$ |
| SEQ ID NO: 166 | $C_sC_sA_sc_sc_sa_sc_sa_sa_sa_sg_st_st_sA_sT_sG$ |
| SEQ ID NO: 167 | $C_sA_sT_sc_sa_sc_st_sc_st_sg_sg_st_sg_sT_sG_sT$ |
| SEQ ID NO: 168 | $G_sA_sC_sa_st_sc_sa_sc_st_sc_st_sg_sg_sT_sG_sT$ |

Example 4

In Vitro Model: Cell Culture

The effect of antisense oligonucleotides on target nucleic acid expression can be tested in any of a variety of cell types provided that the target nucleic acid is present at measurable levels. The target can be expressed endogenously or by transient or stable transfection of a nucleic acid encoding said target. The expression level of target nucleic acid can be routinely determined using, for example, Northern blot analysis, Real-Time PCR, or ribonuclease protection assays. The following cell types are provided for illustrative purposes, but other cell types can be routinely used, provided that the target is expressed in the chosen cell type.

Cells were cultured in the appropriate medium as described below and maintained at 37° C. at 95-98% humidity and 5% $CO_2$. Cells were routinely passaged 2-3 times weekly.

15PC3: The human prostate cancer cell line 15PC3 was cultured in DMEM (Sigma)+10% fetal bovine serum (FBS)+2 mM Glutamax I+gentamicin (25 µg/ml).

HUH7: The human hepatocarcinoma cell line was cultured in DMEM (Sigma)+10% fetal bovine serum (FBS)+2 mM Glutamax I+gentamicin (25 µg/ml)+1×Non Essential Amino Acids.

Example 5

In Vitro Model: Treatment with Antisense Oligonucleotides

The cells were treated with oligonucleotides using the cationic liposome formulation LipofectAMINE 2000 (Gibco) as transfection vehicle. Cells were seeded in 6-well cell culture plates (NUNC) and treated when 80-90% confluent. Oligomer concentrations ranged from 1 nM to 25 nM final concentration. Formulation of oligomer-lipid complexes was carried out essentially as described by the manufacturer using serum-free OptiMEM (Gibco) and a final lipid concentration of 5 µg/mL LipofectAMINE 2000. Cells were incubated at 37° C. for 4 hours and treatment was stopped by removal of oligomer-containing culture medium. Cells were washed and serum-containing medium was added. After oligomer treatment, cells were allowed to recover for 20 hours before they were harvested for RNA analysis.

Example 6

In Vitro Model: Extraction of RNA and cDNA Synthesis

Total RNA was extracted from cells transfected as described above and using the Qiagen RNeasy kit (Qiagen cat. no. 74104) according to the manufacturer's instructions. First strand synthesis was performed using Reverse Transcriptase reagents from Ambion according to the manufacturer's instructions.

For each sample 0.5 μg total RNA was adjusted to (10.8 μl) with RNase free $H_2O$ and mixed with 2 μl random decamers (50 μM) and 4 μl dNTP mix (2.5 mM each dNTP) and heated to 70° C. for 3 min after which the samples were rapidly cooled on ice. After cooling the samples on ice, 2 μl 10× Buffer RT, 1 μl MMLV Reverse Transcriptase (100 U/μl) and 0.25 μl RNase inhibitor (10 U/μl) was added to each sample, followed by incubation at 42° C. for 60 min, heat inactivation of the enzyme at 95° C. for 10 min, and then cooling the sample to 4° C.

Example 7

In Vitro Model: Analysis of Oligonucleotide Inhibition of HER3, EGFR and HER2 Expression by Real-Time PCR Antisense modulation of HER3, EGFR and HER2 expression can be assayed in a variety of ways known in the art. For example, HER3, EGFR and HER2 mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA.

Methods of RNA isolation and RNA analysis, such as Northern blot analysis, are routine in the art and are taught in, for example, Current Protocols in Molecular Biology, John Wiley and Sons.

Real-time quantitative (PCR) can be conveniently accomplished using the commercially available Multi-Color Real Time PCR Detection System, available from Applied Biosystem.

Real-Time Quantitative PCR Analysis of HER3, EGFR and HER2 mRNA Levels

The sample content of human HER3, EGFR and HER2 mRNA was quantified using the human HER3, EGFR and HER2 ABI Prism Pre-Developed TaqMan Assay Reagents (Applied Biosystems cat. no. Hs00951444_m1 (HER3), Hs00193306_m1 (EGFR) and Hs00170433_m1 (HER2) according to the manufacturer's instructions.

Glyceraldehyde-3-phosphate dehydrogenase (GAPDH) mRNA quantity was used as an endogenous control for normalizing any variance in sample preparation. The sample content of human GAPDH mRNA was quantified using the human GAPDH ABI Prism Pre-Developed TaqMan Assay Reagent (Applied Biosystems cat. no. 4310884E) according to the manufacturer's instructions.

Real-time Quantitative PCR is a technique well known in the art and is taught in for example in Heid et al. Real time quantitative PCR, Genome Research (1996), 6: 986-994.

Real Time PCR

The cDNA from the first strand synthesis performed as described in Example 5 was diluted 2-20 times, and analyzed by real time quantitative PCR using Taqman 7500 FAST or 7900 FAST from Applied Biosystems. The primers and probe were mixed with 2×Taqman Fast Universal PCR master mix (2×) (Applied Biosystems Cat.#436-4103) and added to 4 μl cDNA to a final volume of 10 μl. Each sample was analysed in duplicate. Assaying 2-fold dilutions of a cDNA that had been prepared on material purified from a cell line expressing the RNA of interest generated standard curves for the assays. Sterile $H_2O$ was used instead of cDNA for the no-template control. PCR program: 95° C. for 30 seconds, followed by 40 cycles of 95° C., 3 seconds, 60° C., 20-30 seconds. Relative quantities of target mRNA sequence were determined from the calculated Threshold cycle using the Applied Biosystems Fast System SDS Software Version 1.3.1.21. or SDS Software Version 2.3.

Example 8

In Vitro Analysis: Antisense Inhibition of Human HER3, EGFR and HER2 Expression by Oligonucleotide Compounds Oligonucleotides presented in Table 4 were evaluated for their potential to down-regulate HER3, EGFR and HER2 mRNA at concentrations of 1, 5 and 25 nM in 15PC3 cells (or HUH-7 as indicated by *) (see FIGS. 2, 3, 4 and 5). SEQ ID NOs: 235 and 236 were used as scrambled controls.

The data in Table 4 are presented as percentage down-regulation of mRNA relative to mock transfected cells at 25 nM. Lower-case letters represent DNA monomers, bold, upper-case letters represent β-D-oxy-LNA monomers. All cytosines in LNA monomers are 5-methylcytosines. Subscript "s" represents a phosphorothioate linkage.

TABLE 4

Inhibition of human HER3, EGFR and HER2 expressed by antisense oligonucleotides

| Test substance | Sequence (5'-3') | HER3 | EGFR | HER2 |
|---|---|---|---|---|
| SEQ ID NO: 169 | G$_s$C$_s$T$_s$c$_s$c$_s$a$_s$g$_s$a$_s$c$_s$a$_s$t$_s$c$_s$a$_s$C$_s$T$_s$C | 93.4% | 95.2% | 75.8% |
| SEQ ID NO: 170 | C$_s$T$_s$C$_s$c$_s$a$_s$g$_s$a$_s$c$_s$a$_s$t$_s$c$_s$a$_s$c$_s$T$_s$C$_s$T | 85.8% | 91.5% | 65.8% |
| SEQ ID NO: 171 | C$_s$A$_s$G$_s$a$_s$c$_s$a$_s$t$_s$c$_s$a$_s$c$_s$t$_s$c$_s$t$_s$G$_s$G$_s$T | 70.6% | 84.2% | 2.8% |
| SEQ ID NO: 172 | A$_s$G$_s$A$_s$c$_s$a$_s$t$_s$c$_s$a$_s$c$_s$t$_s$c$_s$t$_s$g$_s$G$_s$T$_s$G | 84.2% | 86.2% | 61% |

TABLE 4-continued

Inhibition of human HER3, EGFR and HER2 expressed by antisense oligonucleotides

| Test substance | Sequence (5'-3') | HER3 | EGFR | HER2 |
|---|---|---|---|---|
| SEQ ID NO: 173 | A$_s$T$_s$A$_s$g$_s$c$_s$t$_s$c$_s$c$_s$a$_s$g$_s$a$_s$c$_s$a$_s$T$_s$C$_s$A | 94.5% | 96.4% | 39.2% |
| SEQ ID NO: 174 | T$_s$C$_s$A$_s$c$_s$a$_s$c$_s$c$_s$a$_s$t$_s$a$_s$g$_s$c$_s$t$_s$C$_s$C$_s$A | 88.8% | 86.4% | 94.8% |
| SEQ ID NO: 175 | C$_s$A$_s$T$_s$c$_s$c$_s$a$_s$a$_s$c$_s$a$_s$c$_s$t$_s$t$_s$g$_s$A$_s$C$_s$C | 65.5% | 86.1% | 76.9% |
| SEQ ID NO: 176 | A$_s$T$_s$C$_s$c$_s$a$_s$a$_s$c$_s$a$_s$c$_s$t$_s$t$_s$g$_s$a$_s$C$_s$C$_s$A | 61.6% | 79.4% | 74.8% |
| SEQ ID NO: 177 | C$_s$A$_s$A$_s$t$_s$c$_s$a$_s$t$_s$c$_s$c$_s$a$_s$a$_s$c$_s$a$_s$C$_s$T$_s$T | 51.1% | 0% | 63.4% |
| SEQ ID NO: 178 | T$_s$C$_s$A$_s$a$_s$t$_s$c$_s$a$_s$t$_s$c$_s$c$_s$a$_s$a$_s$c$_s$A$_s$C$_s$T | 76.7% | 0% | 88.6% |
| SEQ ID NO: 179 | C$_s$A$_s$T$_s$g$_s$t$_s$a$_s$g$_s$a$_s$c$_s$a$_s$t$_s$c$_s$a$_s$A$_s$T$_s$T | 70.5% | 52.6% | 75.6% |
| SEQ ID NO: 180 | T$_s$A$_s$G$_s$c$_s$c$_s$t$_s$g$_s$t$_s$c$_s$a$_s$c$_s$t$_s$t$_s$C$_s$T$_s$C | 92.8% | N.D. | N.D. |
| SEQ ID NO: 181 | A$_s$G$_s$A$_s$t$_s$g$_s$g$_s$c$_s$a$_s$a$_s$a$_s$c$_s$t$_s$t$_s$C$_s$C$_s$C | 90.6% | N.D. | N.D. |
| SEQ ID NO: 182 | C$_s$A$_s$A$_s$g$_s$g$_s$c$_s$t$_s$c$_s$a$_s$c$_s$a$_s$c$_s$a$_s$T$_s$C$_s$T | 74.6% | N.D. | N.D. |
| SEQ ID NO: 183 | A$_s$A$_s$G$_s$t$_s$c$_s$c$_s$a$_s$g$_s$g$_s$t$_s$t$_s$g$_s$c$_s$C$_s$C$_s$A | 85.9% | N.D. | N.D. |
| SEQ ID NO: 184 | C$_s$A$_s$T$_s$t$_s$c$_s$a$_s$a$_s$g$_s$t$_s$t$_s$c$_s$t$_s$t$_s$C$_s$A$_s$T | 81.1% | N.D. | N.D. |
| SEQ ID NO: 185 | C$_s$A$_s$C$_s$t$_s$a$_s$a$_s$t$_s$t$_s$t$_s$c$_s$c$_s$t$_s$t$_s$C$_s$A$_s$G | 89.1% | N.D. | N.D. |
| SEQ ID NO: 186 | G$_s$C$_s$C$_s$c$_s$a$_s$g$_s$c$_s$a$_s$c$_s$t$_s$a$_s$a$_s$t$_s$T$_s$T$_s$C | 79.9% | N.D. | N.D. |
| SEQ ID NO: 187 | C$_s$T$_s$T$_s$t$_s$g$_s$c$_s$c$_s$c$_s$t$_s$c$_s$t$_s$g$_s$c$_s$C$_s$A$_s$C | 90.4% | N.D. | N.D. |
| SEQ ID NO: 188 | C$_s$A$_s$C$_s$a$_s$c$_s$a$_s$c$_s$t$_s$t$_s$t$_s$g$_s$c$_s$c$_s$C$_s$T$_s$C | 96.1% | N.D. | N.D. |
| SEQ ID NO: 189 | C$_s$A$_s$G$_s$t$_s$t$_s$c$_s$c$_s$a$_s$a$_s$a$_s$g$_s$a$_s$c$_s$A$_s$C$_s$C | 88.9% | N.D. | N.D. |
| SEQ ID NO: 190 | T$_s$G$_s$G$_s$c$_s$a$_s$a$_s$t$_s$t$_s$t$_s$g$_s$t$_s$a$_s$c$_s$T$_s$C$_s$C | 95.7% | N.D. | N.D. |
| SEQ ID NO: 191 | G$_s$T$_s$G$_s$t$_s$g$_s$t$_s$g$_s$t$_s$a$_s$t$_s$t$_s$t$_s$c$_s$C$_s$C$_s$A | 97.7% | N.D. | N.D. |
| SEQ ID NO: 192 | C$_s$C$_s$C$_s$t$_s$c$_s$t$_s$g$_s$a$_s$t$_s$g$_s$a$_s$c$_s$t$_s$C$_s$T$_s$G | 92.3% | N.D. | N.D |
| SEQ ID NO: 193 | C$_s$A$_s$T$_s$a$_s$c$_s$t$_s$c$_s$c$_s$t$_s$c$_s$a$_s$t$_s$c$_s$T$_s$T$_s$C | 64% | N.D. | N.D. |
| SEQ ID NO: 194 | C$_s$C$_s$A$_s$c$_s$c$_s$a$_s$c$_s$a$_s$a$_s$a$_s$g$_s$t$_s$t$_s$A$_s$T$_s$G | 87.5% | N.D. | N.D. |
| SEQ ID NO: 195 | C$_s$A$_s$T$_s$c$_s$a$_s$c$_s$t$_s$c$_s$t$_s$g$_s$g$_s$t$_s$g$_s$T$_s$G$_s$T | 64.4%* | N.D. | N.D. |
| SEQ ID NO: 196 | G$_s$A$_s$C$_s$a$_s$t$_s$c$_s$a$_s$c$_s$t$_s$c$_s$t$_s$g$_s$g$_s$T$_s$G$_s$T | 77.0%* | N.D. | N.D. |
| SEQ ID NO: 234 | T$_s$A$_s$g$_s$c$_s$c$_s$t$_s$g$_s$t$_s$c$_s$a$_s$C$_s$T$_s$T | | | |
| SEQ ID NO: 235 | C$_s$G$_s$T$_s$c$_s$a$_s$g$_s$t$_s$a$_s$t$_s$g$_s$c$_s$g$_s$A$_s$A$_s$T$_s$c | | | |
| SEQ ID NO: 236 | C$_s$G$_s$C$_s$A$_s$g$_s$a$_s$t$_s$t$_s$a$_s$g$_s$a$_s$a$_s$A$_s$C$_s$C$_s$t | | | |
| SEQ ID NO: 249 | T$_s$A$_s$G$_s$c$_s$c$_s$t$_s$t$_s$t$_s$g$_s$a$_s$c$_s$c$_s$t$_s$C$_s$T$_s$C | | | |

As shown in Table 4, oligonucleotides having the sequences shown in SEQ ID NOs: 169, 170, 173, 174, 180, 181, 183, 185, 187, 188, 189, 190, 191, 192 and 194 demonstrated about 85% or greater inhibition of HER3 mRNA expression at 25 nM in 15PC3 cells in these experiments, and are therefore preferred.

Also preferred are oligonucleotides based on the illustrated antisense oligomer sequences, for example varying the length (shorter or longer) and/or monomer content (e.g., the type and/or proportion of nucleoside analogue monomers), which also provide good inhibition of HER3 expression.

Example 9

Apoptosis Induction by LNA Oligonucleotides

HUH7 cells were seeded in 6-well culture plates (NUNC) the day before transfection at a density of $2.5 \times 10^5$ cells/well. The cells were treated with oligonucleotides using the cationic liposome formulation LipofectAMINE 2000 (Gibco) as transfection vehicle when 75-90% confluent. The oligomer concentrations used were 5 nM and 25 nM (final concentration in well). Formulation of oligomer-lipid complexes was carried out essentially as described by the manufacturer using serum-free OptiMEM (Gibco) and a final lipid concentration of 5 µg/mL LipofectAMINE 2000. Cells were incubated at 37° C. for 4 hours and treatment was stopped by removal of oligomer-containing culture medium. After washing with Optimem, 300 µl of trypsin was added to each well until the cells detached from the wells. The trypsin was inactivated by adding 3 ml HUH7 culture medium to the well and a single cell suspension was made by gently pipetting the cell suspension up and down. The scrambled oligomer SEQ ID NO: 235 was used as control.

Following this, 100 µl of the cell suspension was added to each well of a white 96-well plate from Nunc (cat #136101) (four plates were prepared, for measurement at different time points). The plates were then incubated at 37° C., 95% humidity and 5% $CO_2$ until the assays were performed.

Figure 6:
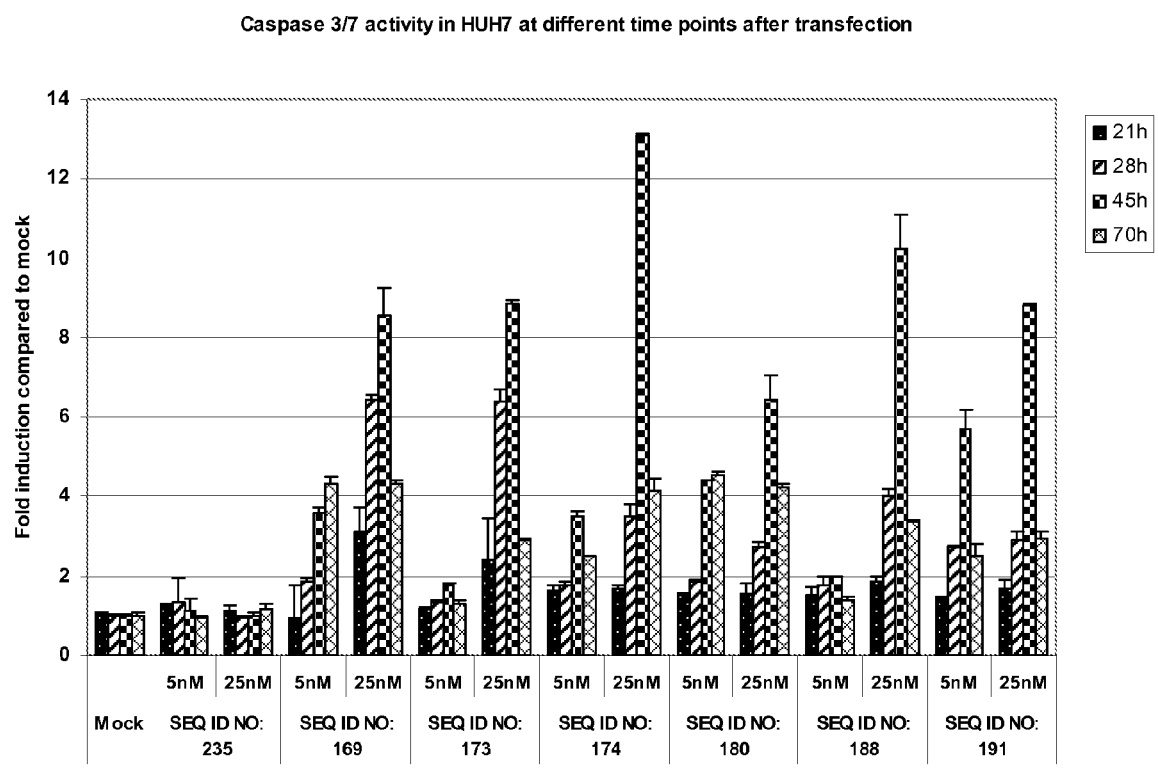
FIG. 6: Data show apoptosis induction measured as activated Caspase 3/7 at different time points in HUH7 cells transfected with oligonucleotides at 5 and 25 nM concentrations. Results are plotted relative to cells mock treated with a scrambled control oligonucleotide having SEQ ID NO: 235.

Caspase assay: The activities of apoptosis-specific caspases 3 and 7 were measured using a luminogenic Caspase-Glo 3/7-substrate assay (Cat#G8091 from Promega). The plate to be analyzed was equilibrated to room temperature for 15 min. The Caspase-Glo® 3/7 buffer was mixed with the Caspase-Glo® 3/7 substrate to form a Caspase-Glo® working solution which was equilibrated to room temperature. Then, 100 µl of the Caspase-Glo® working solution was carefully added to the medium in each well of the 96-well plate (avoiding bubbles and contamination between wells). The plate was carefully shaken for 1 min, after which it was incubated at room temperature for 1 h, protected from light. The caspase activity was measured as Relative Light Units per second (RLU/s) in a Luminoscan Ascent instrument (Thermo Labsystems). Data were correlated and plotted relative to an average value of the mock samples, which was set to 1. See FIG. 6.

Example 10

In Vitro Inhibition of Proliferation Using LNA Oligonucleotides

HUH7 cells were transfected and harvested into a single cell suspension as described in Example 9. SEQ ID NO: 235 served as a scrambled control. Following harvesting, 100 µl of the cell suspension was added to each well of a 96-well plate ("Orange Scientific") for MTS assay (four plates were prepared, for measurement at different time points). The plates were then incubated at 37° C., 95% humidity and 5% $CO_2$ until the assays were performed.

Measurement of Proliferating Viable Cells (MTS Assay)

Figure 7:
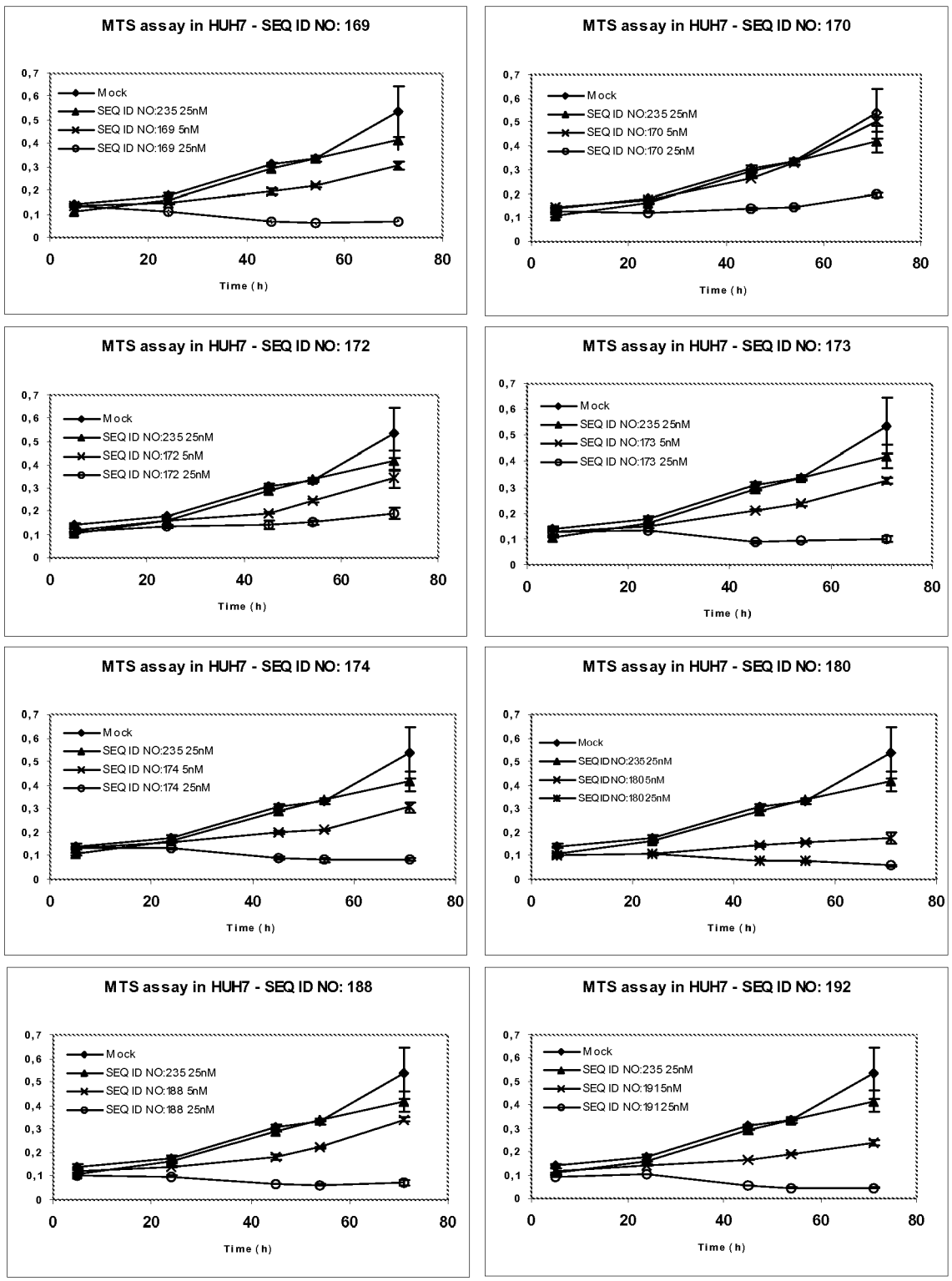
FIG. 7: Data show viable cells measured as OD490 using MTS assay at different time points in HUH-7 cells transfected with oligonucleotides at 5 and 25 nM concentrations. SEQ ID NO: 235 is a scrambled control oligonucleotide.

For the proliferation assay, 10 µl CellTiter 96® AQueous One Solution Cell Proliferation Assay (Promega, G3582) were added to the medium of each well of the 96-well plate, the plate was carefully shaken, and incubated at 37° C., 95% humidity and 5% $CO_2$ for 1 h before measurement. The absorbance was measured at 490 nm in a spectrophotometer and background for the assay was subtracted from wells containing only medium. The absorbance at 490 nm is proportional to the number of viable cells and was plotted over time for the mock transfected cells and for cells transfected with oligomers. See FIG. 7.

Example 11

Evaluation of Target mRNA Knockdown In Vivo

To evaluate the knockdown efficacy of the HER3 oligomeric compounds in vivo, the female nude mice bearing 15PC3 xenografts developed by subcutaneous injection of $5\times10^6$ cells/mouse into the right axillary flank, were injected intravenously with the oligomers at various doses and injection schedules (i.e. single dose, qd, q3d, q4d). Scrambled oligomer SEQ ID NO: 236 served as a negative control. 24 hours after the last injection, the mice were euthanized and liver and tumour tissues were collected in RNA later solution (Ambion). Total RNA was purified from the tissues and the levels of HER3 mRNA were determined by quantitative reverse transcription-real time PCR (qRT-PCR) using the QuantiTect Probe RT-PCR kit (Cat#: 204443; Qiagen). GAPDH mRNA served as an internal control.

Mouse HER3: probe: cca cac ctg gtc ata gcg gtg a, primer-1: ctg ttt agg cca agc aga gg, primer-2: att ctg aat cct gcg tcc ac.

Human HER3: probe: cat tgc cca acc tcc gcg tg, primer-1: tgc agt gga ttc gag aag tg, primer-2: ggc aaa ctt ccc atc gta ga.

Human GAPDH: probe: act ggc gct gcc aag gct gt, primer-1: cca ccc aga aga ctg tgg at, primer-2: ttc agc tca ggg atg acc tt.

Mouse GAPDH: probe: agc tgt ggc gtg atg gcc gt, primer-1: aac ttt ggc att gtg gaa gg, primer-2: gga tgc agg gat gat gtt ct 200 ng of total RNA was used in the PCR reaction. The data analyses were performed by using the ABI-7500 PCR Fast System included software. See Table 5.

Data in Table 5 are presented as % HER3 mRNA levels relative to saline treated controls in liver and tumour samples after i.v. dosing of animals on 5 consecutive days with oligonucleotides in the doses indicated.

TABLE 5

Inhibition of HER3 mRNA in mouse liver and tumour

| LNA ID | Dosage (mg/kg, i.v., qd × 5) | HER3 mRNA | |
|---|---|---|---|
| | | Liver (% or Sal ctrl) | Tumour (%) |
| SEQ ID NO: 236 | 76.3 | 78 ± 17 | 100 ± 10.5 |
| | 60 | 86.5 ± 9.9 | 95.5 ± 12.7 |
| | 30 | 87.6 ± 19 | 101.2 ± 21.1 |
| | 22.9 | 81.4 ± 6.5 | 119.3 ± 24.9 |
| SEQ ID NO: 180 | 85.3 | 1 ± 0.3 | 25.8 ± 4.1 |
| | 66 | 6 ± 5.3 | 32.3 ± 9.7 |
| | 31.3 | 1.6 ± 0.3 | 37 ± 5.8 |
| | 25.6 | 3 ± 0.3 | 65 ± 20.2 |
| | 19.8 | 1.7 ± 0.6 | 83.1 ± 19.5 |
| SEQ ID NO: 169 | 37.7 | 20.7 ± 9.8 | 77 ± 10 |
| | 11.3 | 10.2 ± 5.5 | ND |
| SEQ ID NO: 172 | 32.4 | 7.4 ± 5.2 | 78.1 ± 15.3 |
| | 9.7 | 12.2 ± 5.9 | ND |

Example 12

Evaluation of Tumour Growth Inhibition

Figure 8A:
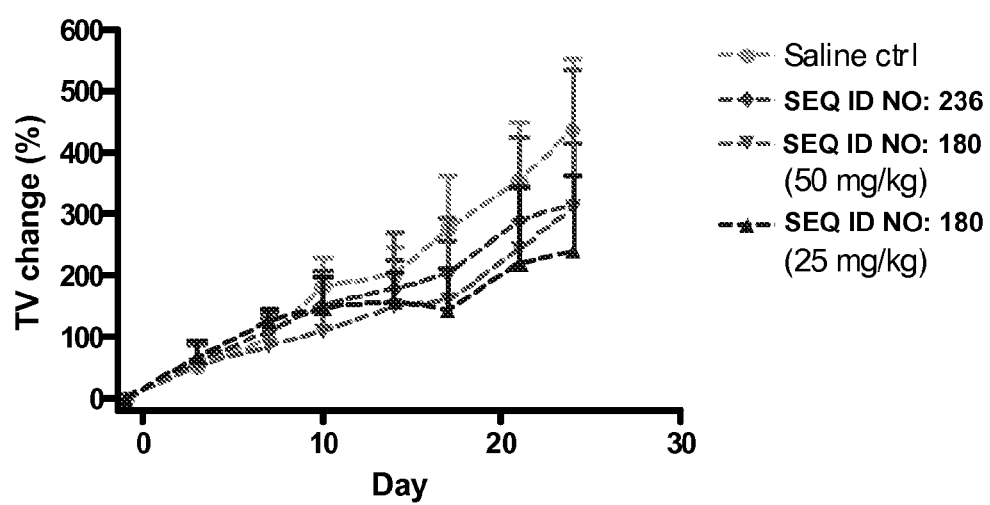
FIG. 8A: Data show percent change in tumour volume in 15PC3 xenograft tumours transplanted onto female nude mice treated with SEQ ID NO: 180 i.v. at 25 and 50 mg/kg q3dx10. Saline treated mice were used as control.
Figure 8B:
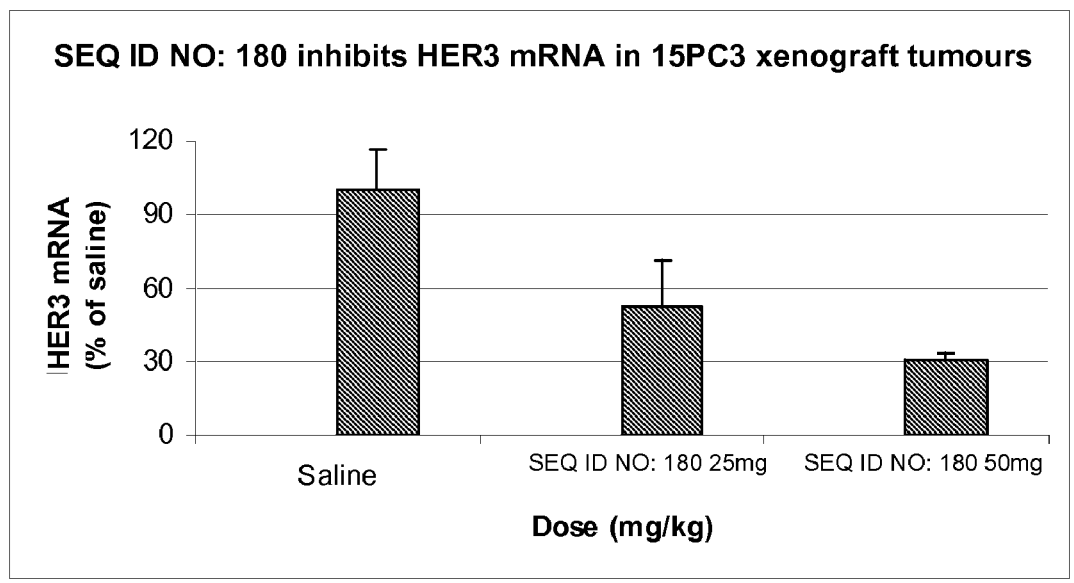
FIG. 8B: Data show HER3 mRNA expression in 15PC3 xenograft tumours transplanted onto female nude mice treated with SEQ ID NO: 180 i.v. at 25 and 50 mg/kg q3dx10. Results are normalised to GAPDH and presented as % of saline treated controls.

The ability of the HER3 specific LNAs to inhibit tumour growth in vivo was evaluated in nude female mice bearing 15PC3 xenografts. 15PC3 human prostate tumour model was developed by subcutaneously injection of $5 \times 10^6$ cells/mouse into the right axillary flank. The tumour volume was determined by measuring two dimensions with callipers and calculated using the formula: tumour volume=(length×width$^2$)/2). When the tumours reached an average volume of 70-100 mm$^3$, the mice bearing tumours were divided into treatment and control groups. The mice were injected intravenously with 25 and 50 mg/kg of SEQ ID NO: 180 respectively, with a q3d×10 schedule. Saline or scrambled oligonucleotide having SEQ ID NO: 236 served as a control. The body weights and tumour sizes of the mice were measured twice weekly. The toxicity was estimated by clinical observation, clinical chemistry and histopathological examination. Tumour HER3 mRNA was measured by QPCR as described in Example 11. See FIGS. 8A and 8B.

Example 13

Inhibition of HER3 mRNA in Mouse Liver

Figure 9:
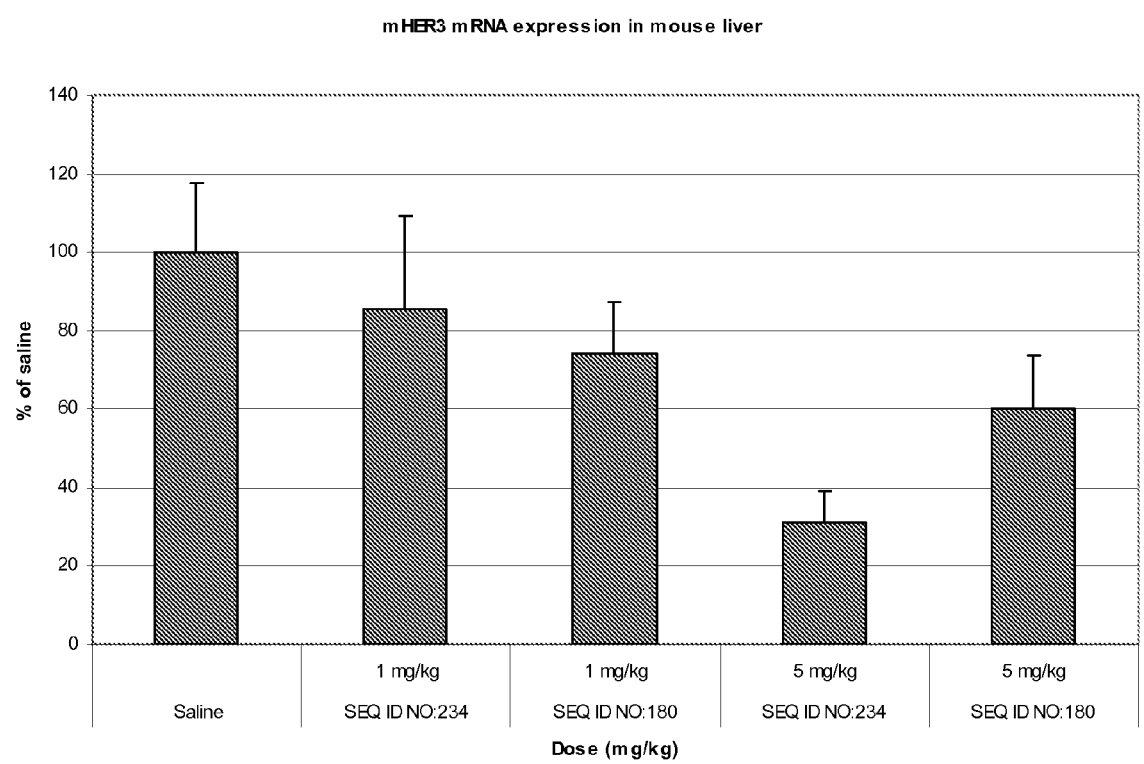
FIG. 9: Data show HER3 mRNA expression in mouse liver after treatment i.v. with 1 or 5 mg/kg oligonucleotides on three consecutive days having sequences shown in SEQ ID NO: 180 or SEQ ID NO: 234. Results are normalised to GAPDH and presented as % of saline treated controls.

NMRI mice were dosed i.v. with 1 or 5 mg/kg oligonucleotides on three consecutive days (group size of 5 mice). The antisense oligonucleotides (SEQ ID NO: 180 and SEQ ID NO: 234) were dissolved in 0.9% saline (NaCl). Animals were sacrificed 24 h after last dosing and liver tissue was sampled and stored in RNA later (Ambion) until RNA extraction and QPCR analysis. Total RNA was extracted and HER3 mRNA expression in liver samples was measured by QPCR as described in Example 7 using a mouse HER3QPCR assay (cat. no. Mm01159999_m1, Applied Biosystems). Results were normalised to mouse GAPDH (cat. no. 4352339E, Applied Biosystems) and plotted relative to saline treated controls (see FIG. 9).

Example 14

Preparation of Conjugates of Oligomers with Polyethylene Glycol

The oligomers having sequences shown as SEQ ID NO: 141 or SEQ ID NO: 152 are functionalized on the 5' terminus by attaching an aminoalkyl group, such as hexan-1-amine blocked with a blocking group such as Fmoc to the 5' phosphate groups of the oligomers using routine phosphoramidite chemistry, oxidizing the resultant compounds, deprotecting them and purifying them to achieve the functionalized oligomers, respectively, having the formulas (IA) and (IB):

wherein the bold uppercase letters represent nucleoside analogue monomers, lowercase letters represent DNA monomers, and the subscript "s" represents a phosphorothioate linkage.

A solution of activated PEG, such as the one shown in formula (II):

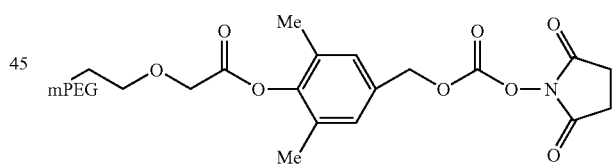

wherein the PEG moiety has an average molecular weight of 12,000, and each of the compounds of formulas (IA) and (IB) in PBS buffer are stirred in separate vessels at room temperature for 12 hours. The reaction solutions are extracted three times with methylene chloride and the combined organic layers are dried over magnesium sulphate and filtered and the solvent is evaporated under reduced pressure. The resulting residues are dissolved in double distilled water and loaded onto an anion exchange column. Unreacted PEG linker is eluted with water and the products are eluted with NH$_4$HCO$_3$ solution. Fractions containing pure products are pooled and lypophilized to yield the conjugates SEQ ID NOs: 141 and 152, respectively as show in formulas (IIIA) and (IIIB):

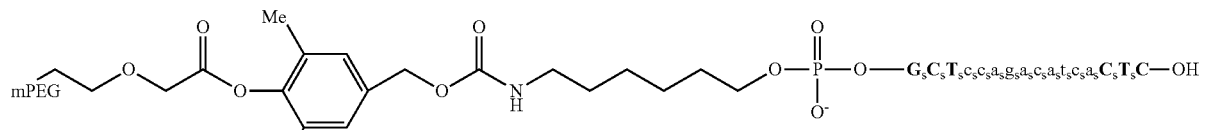

(IIIA)

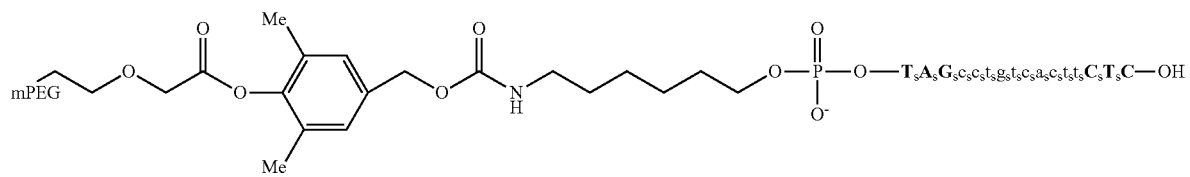

(IIIB)

wherein each of the oligomers of SEQ ID NOs: 141 and 152 is attached to a PEG polymer having average molecular weight of 12,000 via a releasable linker. Chemical structures of PEG polymer conjugates that can be made with oligomers having sequences shown in SEQ ID NOs: 169, 180 and 234 using the process described above are respectively shown in formulas (IVA), (IVB) and (IVC):

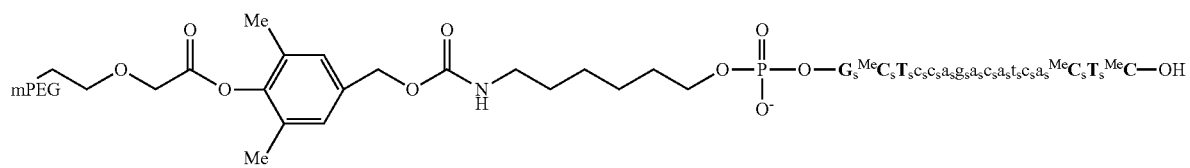

(IVA)

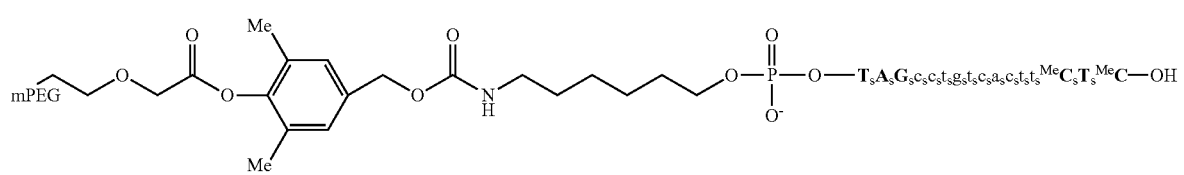

(IVB)

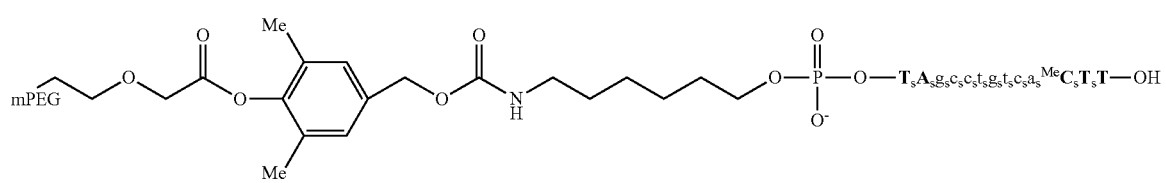

(IVC)

wherein bold uppercase letters represent beta-D-oxy-LNA monomers, lowercase letters represent DNA monomers, the subscript "s" represents a phosphorothioate linkage and MeC represent 5-methylcytosine. Activated oligomers that can be used in this process to respectively make the conjugates shown in formulas (IVA), (IVB) and (IVC) have the chemical structures shown in formulas (VA), (VB) and (VC):

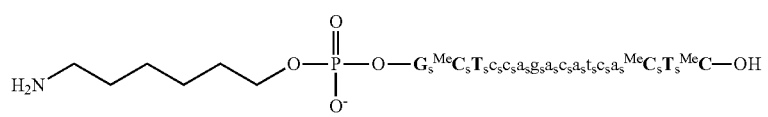

(VA)

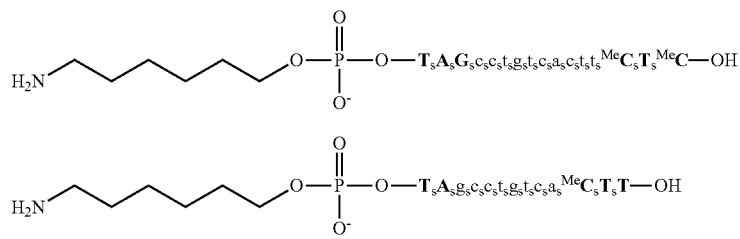

Example 15

Evaluation of Target mRNA Knockdown In Vivo with Different Dosing Cycle

The knockdown efficacy of oligomers was evaluated in vivo in nude mice bearing xenograft tumours derived from 15PC3 cells or A549 cells (NSCLC) or N87 cells (gastric carcinoma) using a similar protocol to the one described above in Example 11. Oligomers were administered by injection every third day in 2-4 doses. Tissues were harvested 3 or 4 days after the last injection.

Data in Tables 6 and 7 are presented as % HER3 mRNA or HIF-1alpha mRNA relative to saline treated controls in liver and tumour samples after i.v. dosing of animals with the indicated oligomers.

TABLE 6

Inhibition of ErbB3 mRNA in mouse liver and xenograft tumor derived from 15PC3 cell (3-5 mice/group)

| Treatment | Dosage (mg/kg) | Tumour HER3 (%) | Tumour Hif1A (%) | Liver HER3 (%) |
|---|---|---|---|---|
| Saline | 0 × 4 | 100 ± 10 | 100 ± 8 | 100 ± 18 |
| SEQ ID No: 236 | 76.3 × 4 | 106 ± 6.6 | 101 ± 13.8 | 115.9 ± 26.3 |
| SEQ ID No: 169 | 37.7 × 4 | 81.6 ± 12.7 | 94.6 ± 19.6 | 39 ± 4.6 |
| SEQ ID No: 172 | 32.4 × 4 | 107.3 ± 17 | 100.3 ± 7.5 | 44.3 ± 10.6 |
| SEQ ID No: 180 | 60.2 × 2 or 3 | 47.1 ± 2.2 | 101 ± 7.3 | 6.9 ± 3.6 |
|  | 60.2 × 4 | 54.2 ± 9.1 | ND | 31.8 ± 5 |

The observed knockdown effects of the oligomers having the sequences of SEQ ID NO: 169 and SEQ ID NO: 180 are not unique to 15PC3 tumour cells, since similar effects were observed in the tumours derived from A549 (NSCLC) and N87 (gastric carcinoma) cells. See Table 7, below.

TABLE 7

Inhibition of ErbB3 mRNA in mouse liver and xenograft tumor derived from N87 cell (3 mice/group)

| Xenograft model | Treatment | Dosage mg/kg | HER3 (% saline control) Tumor | HER3 (% saline control) Liver |
|---|---|---|---|---|
| A549 | Saline | 0 × 3 | 100 ± 20.9 | 100 ± 4.8 |
|  | SEQ ID No: 236 | 35, q4 d × 3 | 87.6 ± 11.9 | 97.5 ± 21.2 |
|  | SEQ ID No: 180 | 35, q4 d × 3 | 54.6 ± 15.2 | 31.8 ± 5.7 |
| N87 | Saline | 0 × 5 | 100 ± 8.2 | 100 ± 9.4 |
|  | SEQ ID No: 249 | 25, q3 d × 5 | 99.0 ± 8.9 | 123 ± 4.5 |
|  | SEQ ID No: 180 | 25, q3 d × 5 | 46.6 ± 13.4 | 24.7 ± 3.1 |

SPECIFIC EMBODIMENTS, CITATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein; the disclosure of each such reference is hereby incorporated herein by reference in its entirety.

---

The invention claimed is:

1. An oligomer consisting of:

5'-$T_s A_s G_s c_s c_s t_s g_s t_s c_s a_s c_s t_s t_s{}^{Me}C_s T_s{}^{Me}C$-3' (SEQ ID NO: 180), wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methylcytosine base.

2. The oligomer according to claim 1, which inhibits the expression of a human HER3 gene or mRNA in a cell that expresses HER3.

3. A conjugate comprising an oligomer according to claim 1 covalently attached to at least one moiety that is not a nucleic acid or a monomer.

4. A pharmaceutical composition comprising the oligomer according to claim 1, and a pharmaceutically acceptable diluent, carrier, salt or adjuvant.

5. A method of inhibiting the expression of HER3 in a cell, comprising contacting said cell with an effective amount of an oligomer consisting of:

5'-$T_s A_s G_s c_s c_s t_s g_s t_s c_s a_s c_s t_s t_s{}^{Me}C_s T_s{}^{Me}C$-3" (SEQ ID NO: 180), wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methylcytosine base.

6. A method of inhibiting the expression of HER3 in a cell, comprising contacting said cell with an effective amount of a conjugate according to claim 5.

7. A method of inhibiting the expression of HER3 in a tissue of a mammal, comprising contacting said tissue with an effective amount of an oligomer consisting of:

5'-$T_s A_s G_s c_s c_s t_s g_s t_s c_s a_s c_s t_s t_s{}^{Me}C_s T_s{}^{Me}C$-3' (SEQ ID NO: 180), wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methylcytosine base.

8. A method of inhibiting the expression of HER3 in a tissue of a mammal comprising contacting said tissue with an effective amount of a conjugate according to claim 4.

9. A method of treating cancer in a mammal, comprising administering to said mammal an effective amount of an oligomer consisting of:

5'-$T_s A_s G_s c_s c_s t_s g_s t_s c_s a_s c_s t_s t_s{}^{Me}C_s T_s{}^{Me}C$-3' (SEQ ID NO: 180).

wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methylcytosine base.

10. The method of claim 9, wherein the cancer is selected from non-Hodgkin's lymphoma, Hodgkin's lymphoma, acute leukemia such as acute lymphocytic leukemia, acute myelocytic leukemia, chronic myeloid leukemia, chronic lymphocytic leukemia, multiple myeloma, colon carcinoma, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumour, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma.

11. A pharmaceutical composition comprising the conjugate according to claim 3, and a pharmaceutically acceptable diluent, carrier, salt or adjuvant.

* * * * *

UNITED STATES PATENT AND TRADEMARK OFFICE
CERTIFICATE OF CORRECTION

| | |
|---|---|
| PATENT NO. | : 8,268,793 B2 |
| APPLICATION NO. | : 12/118271 |
| DATED | : September 18, 2012 |
| INVENTOR(S) | : Hedtjarn |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 448 days.

Signed and Sealed this
Twenty-eighth Day of May, 2013

Teresa Stanek Rea
*Acting Director of the United States Patent and Trademark Office*